United States Patent
Irvine et al.

(10) Patent No.: US 11,224,648 B2
(45) Date of Patent: Jan. 18, 2022

(54) ANTIGEN-ADJUVANT COUPLING REAGENTS AND METHODS OF USE

(71) Applicants: Massachusetts Institute of Technology, Cambridge, MA (US); The Scripps Research Institute, La Jolla, CA (US)

(72) Inventors: Darrell J. Irvine, Arlington, MA (US); Tyson Moyer, Boston, MA (US); William R. Schief, Encinitas, CA (US)

(73) Assignees: Massachusetts Institute of Technology, Cambridge, MA (US); The Scripps Research Institute, La Jolla, CA (US)

( * ) Notice: Subject to any disclaimer, the term of this patent is extended or adjusted under 35 U.S.C. 154(b) by 129 days.

(21) Appl. No.: 16/226,376

(22) Filed: Dec. 19, 2018

(65) Prior Publication Data

US 2019/0358312 A1    Nov. 28, 2019

Related U.S. Application Data

(60) Provisional application No. 62/607,691, filed on Dec. 19, 2017.

(51) Int. Cl.
| | |
|---|---|
| *A61K 45/06* | (2006.01) |
| *C07K 16/28* | (2006.01) |
| *A61K 39/00* | (2006.01) |
| *A61K 39/395* | (2006.01) |
| *C07K 16/30* | (2006.01) |
| *A61K 39/12* | (2006.01) |
| *A61K 39/39* | (2006.01) |

(52) U.S. Cl.
CPC .............. *A61K 39/12* (2013.01); *A61K 39/39* (2013.01); *A61K 2039/55505* (2013.01); *A61K 2039/55555* (2013.01); *A61K 2039/70* (2013.01)

(58) Field of Classification Search
CPC ..... A61K 2300/00; A61K 45/06; A61P 35/00; A61P 43/00; Y02A 50/30
See application file for complete search history.

(56) References Cited

U.S. PATENT DOCUMENTS 6,086,881 A * 7/2000 Frey .................. A61K 39/385
424/194.1
2012/0177681 A1   7/2012 Singh et al.

FOREIGN PATENT DOCUMENTS

| WO | 2004/097000 A2 | 11/2004 |
| WO | WO2004097000 | * 11/2004 |
| WO | 2017/181128 A1 | 10/2017 |
| WO | 2019126371 A1 | 6/2019 |

OTHER PUBLICATIONS

U.S. Appl. No. 16/857,999, filed Apr. 24, 2020, Darrell J. Irvine.
International Search Report and Written Opinion, PCT/US2018/066576, dated Mar. 29, 2019, 17 pages.
Weissburg R. et al., "Characterization of the MN gp120 HIV-1 vaccine: antigen binding to alum," Pharmaceutical Res., vol. 12(10):1439-1446(1995).
Aznar, M. Angela, et al. "Intratumoral delivery of immunotherapy—act locally, think globally." The Journal of Immunology 198.1: 31-39 (2017).
Buchbinder, Elizabeth I., et al. "Therapy with high-dose Interleukin-2 (HD IL-2) in metastatic melanoma and renal cell carcinoma following PD1 or PDL1 inhibition." Journal for immunotherapy of cancer 7.1: 49 (2019).
Castro, Flávia, et al. "Interferon-gamma at the crossroads of tumor immune surveillance or evasion." Frontiers in immunology 9: 847 (2018).
Cerofolini, L. et al., "Structural characterization of a protein adsorbed on aluminum hydroxide adjuvant in vaccine formulation," NPJ Vaccines,vol. 4, article 20 (2019).
Flarend, Richard E., et al. "In vivo absorption of aluminium-containing vaccine adjuvants using 26Al." Vaccine 15.12-13 (1997): 1314-1318.
Hodi, F. Stephen, et al. "Improved survival with ipilimumab in patients with metastatic melanoma." New England Journal of Medicine 363.8 (2010): 711-723.
HogenEsch, H. et al., "Optimizing the utilization of aluminum adjuvants in vaccines: you might just get what you want." npj Vaccines 3.1 (2018): 51.
International Preliminary Report on Patentability, PCT/US2018/066576, dated Jun. 23, 2020, 8 pages.
International Search Report and Written Opinion, PCT/US2020/029852, dated Aug. 7, 2020, 19 pages.
Iyer, S. et al., "Effect of the degree of phosphate substitution in aluminum hydroxide adjuvant on the adsorption of phosphorylated proteins," Pharmaceutical Development and Technology,vol. 8(1):81-86 (2003).
Jacobson, Lee S., et al. "Cathepsin-mediated necrosis controls the adaptive immune response by Th2 (T helper type 2)-associated adjuvants." Journal of Biological Chemistry 288.11 (2013): 7481-7491.

(Continued)

*Primary Examiner* — Barry A Chestnut

(74) *Attorney, Agent, or Firm* — McDonnell Boehnen Hulbert & Berghoff

(57) ABSTRACT

The present disclosure relates to compositions and methods for coupling an antigen to an adjuvant, immunogenic compositions and vaccines. The methods of the invention can be used to increase an immune response, or to treat cancer or an infectious disease.

26 Claims, 22 Drawing Sheets
(19 of 22 Drawing Sheet(s) Filed in Color)
Specification includes a Sequence Listing.

(56) References Cited

OTHER PUBLICATIONS

Jully, Vanessa, et al. "Mechanisms of antigen adsorption onto an aluminum-hydroxide adjuvant evaluated by high-throughput screening." Journal of pharmaceutical sciences 105.6 (2016): 1829-1836.

Milling, L. et al., "Delivering safer immunotherapies for cancer." Advanced drug delivery reviews 114 (2017): 79-101.

Morefield, G.L. et al., "Effect of phosphorylation of ovalbumin on adsorption by aluminum-containing adjuvants and elution upon exposure to interstitial fluid," Vaccine, vol. 23 (12):1502-1506 (2005).

Moyer, T. et al., "Engineered immunogen binding to alum adjuvant enhances humoral immunity," Nature Medicine, vol. 26(3):430-440 (2020).

Moynihan, Kelly D., Opel, Cary F. et al. "Eradication of large established tumors in mice by combination immunotherapy that engages innate and adaptive immune responses." Nature medicine 22.12 (2016): 1402.

Ribas, Antoni, and Jedd D. Wolchok. "Cancer immunotherapy using checkpoint blockade." Science 359.6382 (2018): 1350-1355.

Riley, Rachel S., et al. "Delivery technologies for cancer immunotherapy." Nature Reviews Drug Discovery vol. 18: 175-196 (2019).

Tagliabracci, Vincent S., et al. "A single kinase generates the majority of the secreted phosphoproteome." Cell 161.7 (2015): 1619-1632.

Tagliabracci, Vincent S., et al. "Secreted kinase phosphorylates extracellular proteins that regulate biomineralization." Science 336. 6085 (2012): 1150-1153.

Ishikawa, H. et al., "Four-jointed is a Golgi kinase that phosphorylates a subset of cadherin domains," Science, vol. 321(5887):401-404 (2008).

Zheng, Y. et al., "Structural changes of protein antigens due to adsorption onto and release from aluminium hydroxide using FTIR-ATR," Spectroscopy, vol. 21: 211-226 (2007).

Zhu, E. et al., "Synergistic Innate and Adaptive Immune Response to Combination Immunotherapy with Anti-Tumor Antigen Antibodies and Extended Serum Half-Life IL-2," Cancer Cell, vol. 27(4): 489-501 (2015).

Bordoli, M. et al., "A Secreted Tyrosine Kinase Acts in the Extracellular Environment," Cell, vol. 158 (Issue 5): 1033-1044 (2014).

* cited by examiner

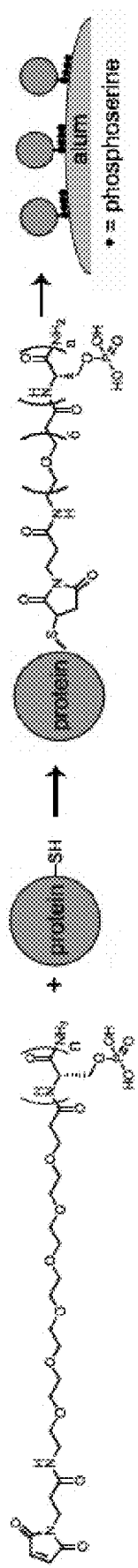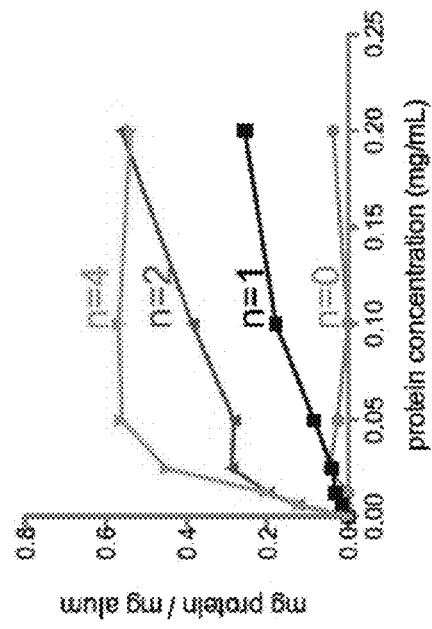
FIG. 1A  FIG. 1B  FIG. 1C  FIG. 1D

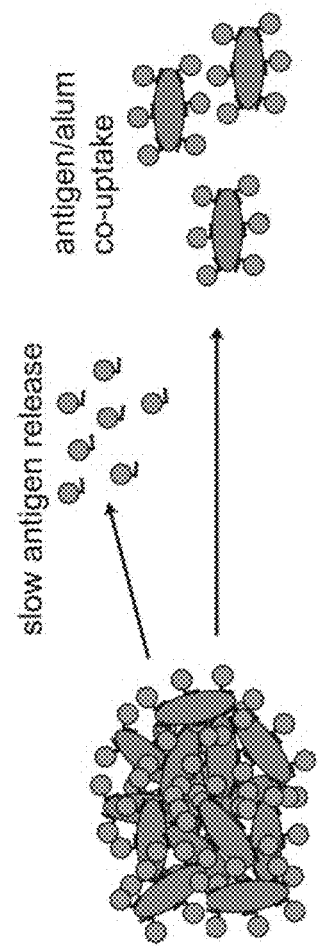
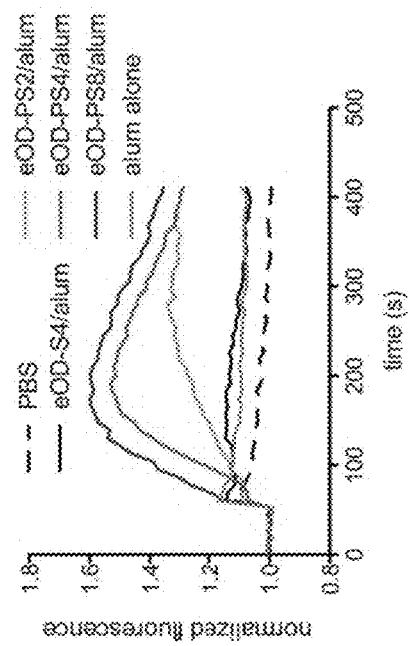
FIG. 6A
FIG. 6B
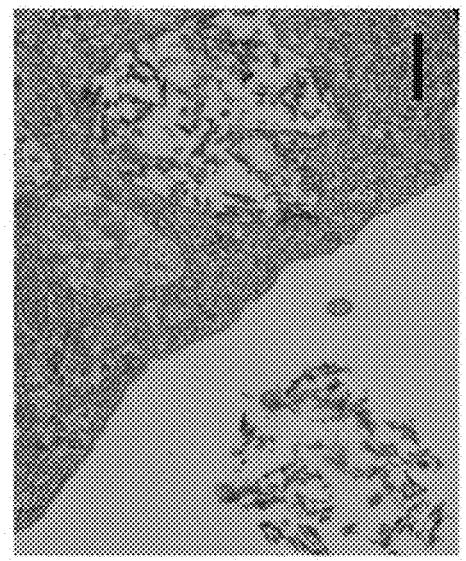
FIG. 6E
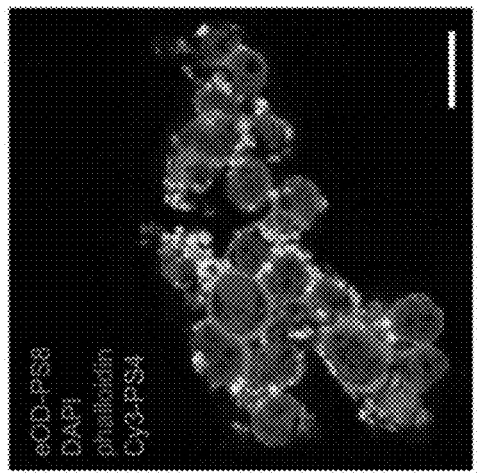
FIG. 6D
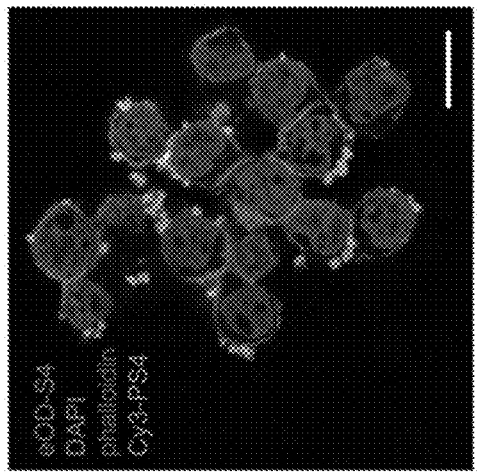
FIG. 6C

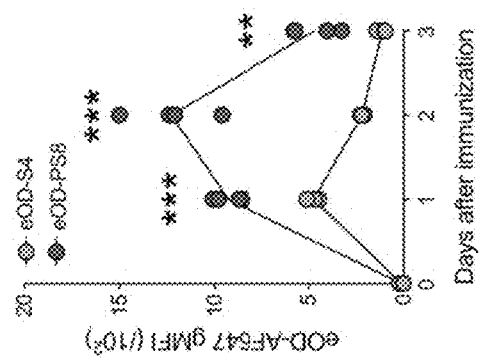
FIG. 11A
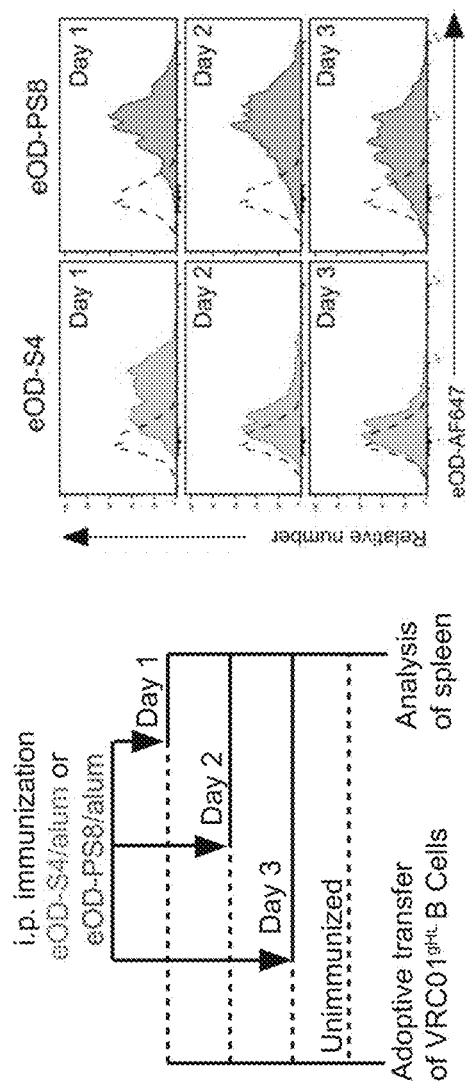
FIG. 11B
FIG. 11D
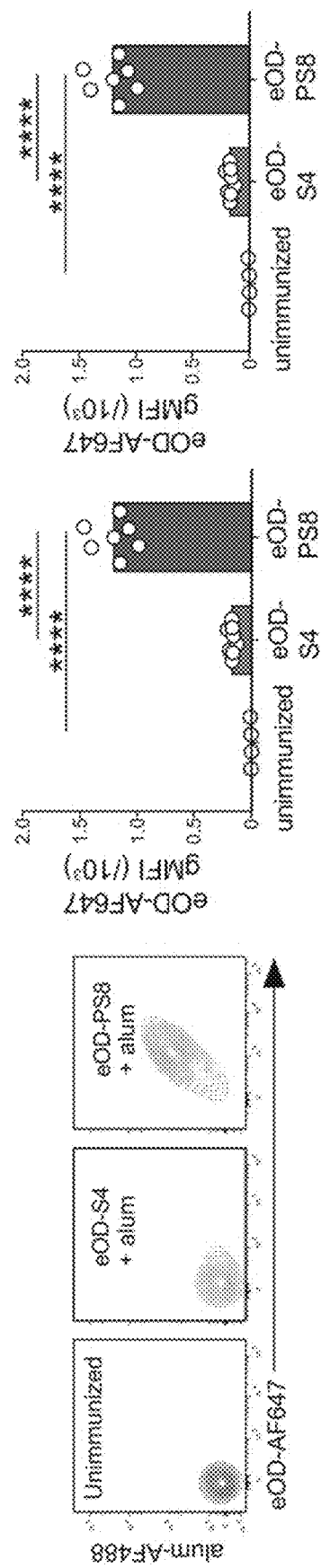
FIG. 11C
FIG. 11E
FIG. 11F

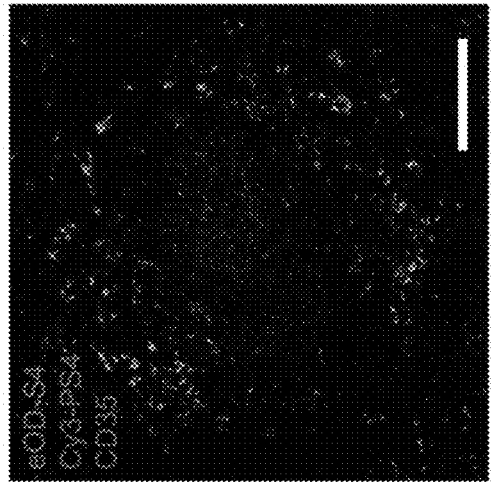
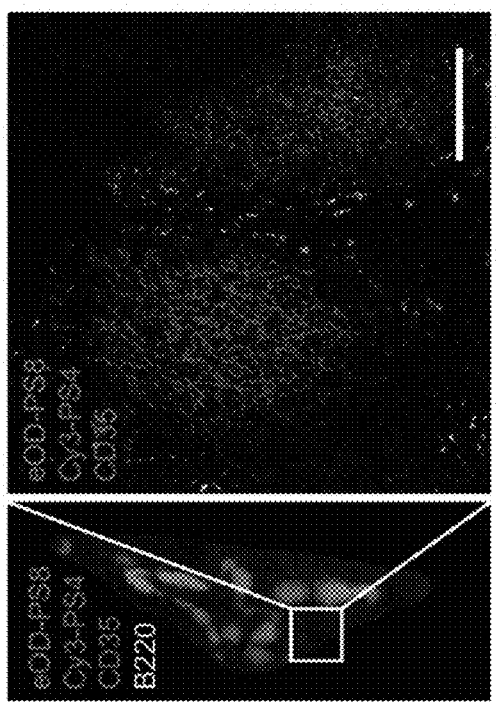
FIG. 12A
FIG. 12B
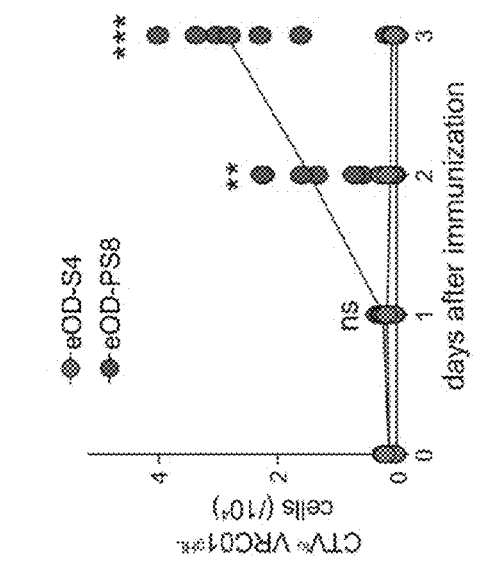
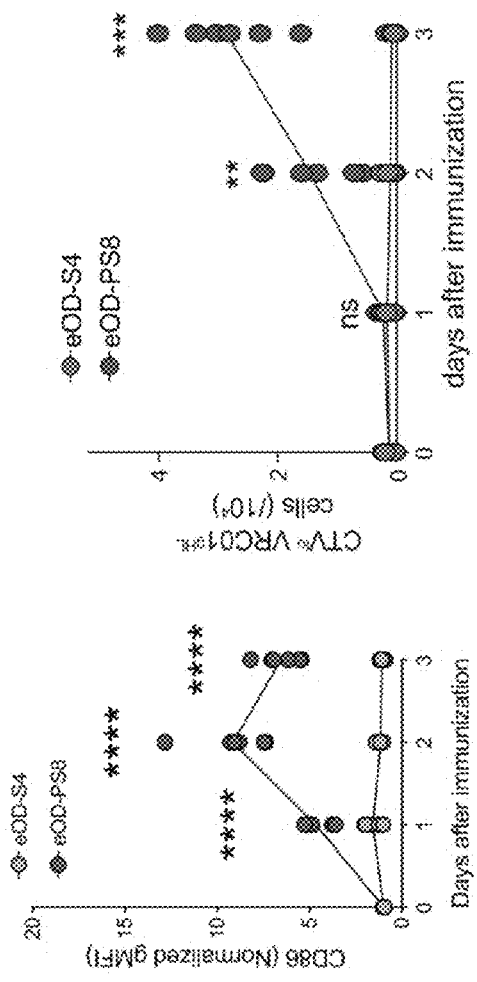
FIG. 12C
FIG. 12D

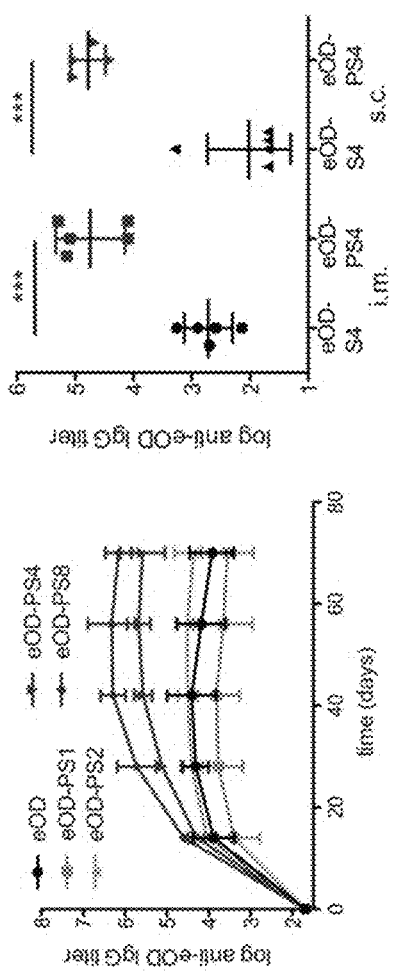
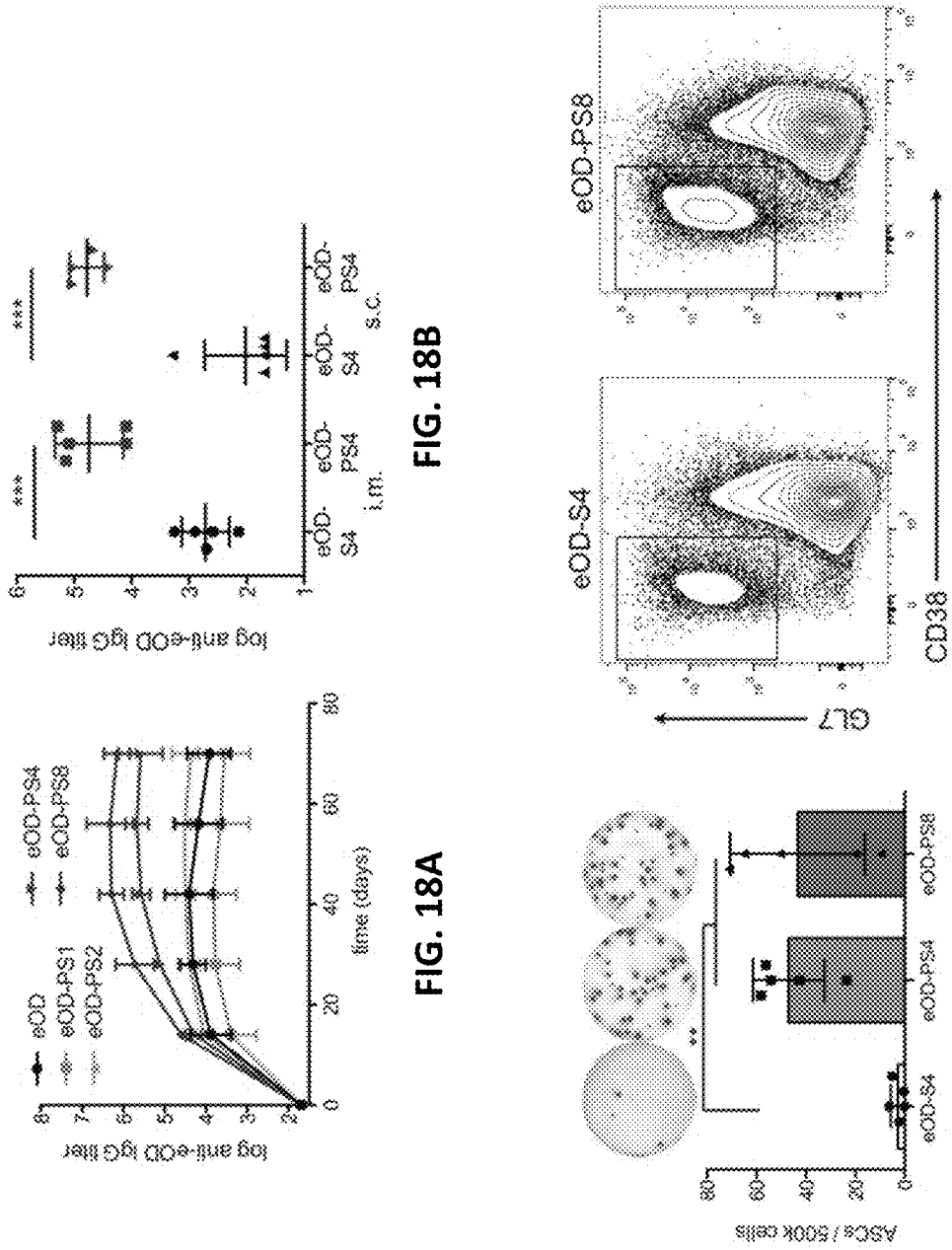
FIG. 18A
FIG. 18B
FIG. 18C
FIG. 18D

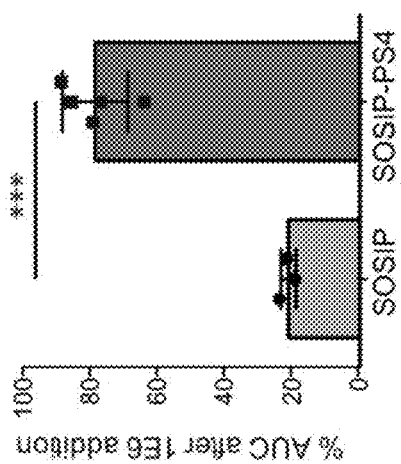
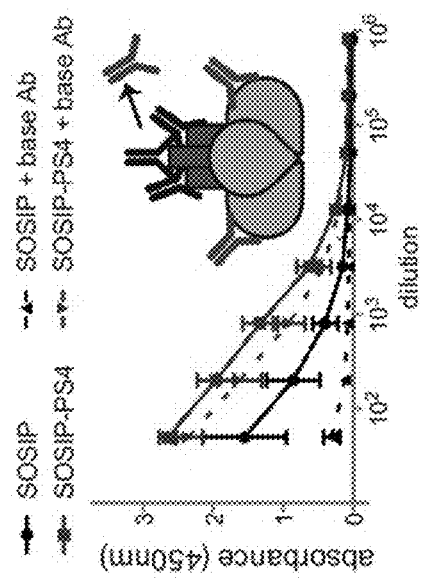
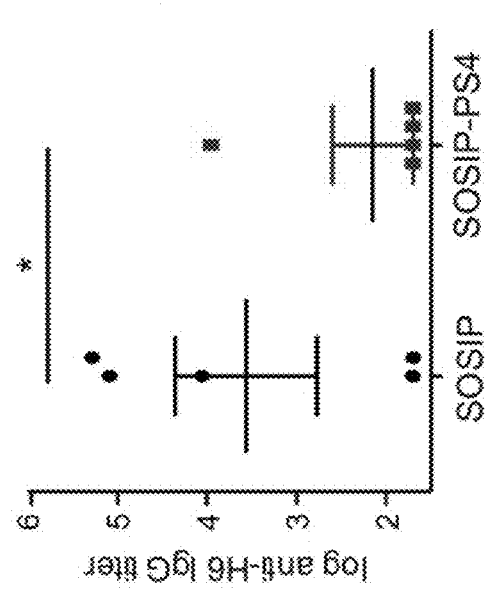
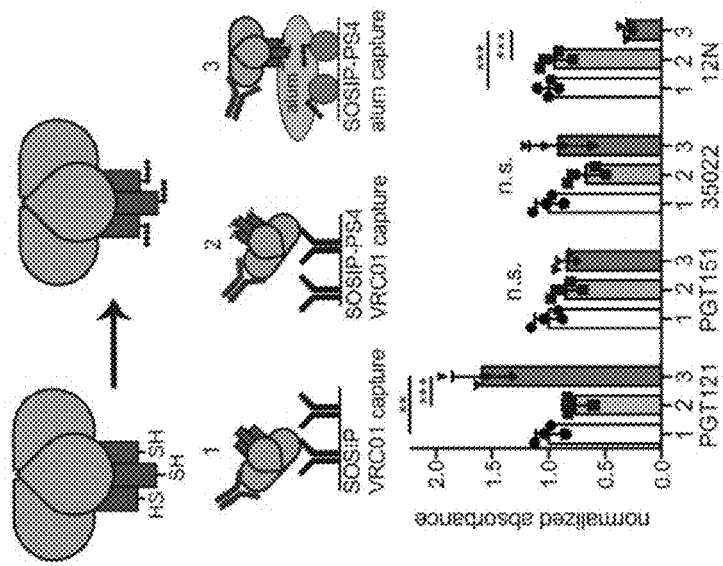
FIG. 21A
FIG. 21B
FIG. 21C
FIG. 21D
FIG. 21E

SEQUENCE LISTING

```
<160> NUMBER OF SEQ ID NOS: 14

<210> SEQ ID NO 1
<211> LENGTH: 198
<212> TYPE: PRT
<213> ORGANISM: Artificial Sequence
<220> FEATURE:
<223> OTHER INFORMATION: Synthetic: amino acid sequence of eOD

<400> SEQUENCE: 1

Thr Gly Cys His His His His His Gly Gly Asp Thr Ile Thr Leu
1               5                   10                  15

Pro Cys Arg Pro Ala Pro Pro His Cys Ser Ser Asn Ile Thr Gly
            20                  25                  30

Leu Ile Leu Thr Arg Gln Gly Gly Tyr Ser Asn Asp Asn Thr Val Ile
        35                  40                  45

Phe Arg Pro Ser Gly Gly Asp Trp Arg Asp Ile Ala Arg Cys Gln Ile
    50                  55                  60

Ala Gly Thr Val Val Ser Thr Gln Leu Phe Leu Asn Gly Ser Leu Ala
65                  70                  75                  80

Glu Glu Glu Val Val Ile Arg Ser Glu Asp Trp Arg Asp Asn Ala Lys
                85                  90                  95

Ser Ile Cys Val Gln Leu Asn Thr Ser Val Glu Ile Asn Cys Thr Gly
            100                 105                 110

Ala Gly His Cys Asn Ile Ser Arg Ala Lys Trp Asn Asn Thr Leu Lys
        115                 120                 125

Gln Ile Ala Ser Lys Leu Arg Glu Gln Tyr Gly Asn Lys Thr Ile Ile
    130                 135                 140

Phe Lys Pro Ser Ser Gly Gly Asp Pro Glu Phe Val Asn His Ser Phe
145                 150                 155                 160

Asn Cys Gly Gly Glu Phe Phe Tyr Cys Asp Ser Thr Gln Leu Phe Asn
                165                 170                 175

Ser Thr Trp Phe Asn Ser Thr Gly Ser Ala Phe Lys Val Ala Ala Trp
            180                 185                 190

Thr Leu Lys Ala Ala Ala
        195
```

<210> SEQ ID NO 2
<211> LENGTH: 646
<212> TYPE: PRT
<213> ORGANISM: Artificial Sequence
<220> FEATURE:
<223> OTHER INFORMATION: Synthetic: amino acid sequence of the cysteine-modified SOSIP

<400> SEQUENCE: 2

```
Thr Gly Ala Glu Asn Leu Trp Val Thr Val Tyr Tyr Gly Val Pro Val
1               5                   10                  15

Trp Lys Asp Ala Glu Thr Thr Leu Phe Cys Ala Ser Asp Ala Lys Ala
            20                  25                  30

Tyr Glu Thr Glu Lys His Asn Val Trp Ala Thr His Ala Cys Val Pro
        35                  40                  45

Thr Asp Pro Asn Pro Gln Glu Ile His Leu Glu Asn Val Thr Glu Glu
    50                  55                  60

Phe Asn Met Trp Lys Asn Asn Met Val Glu Gln Met His Thr Asp Ile
65                  70                  75                  80

Ile Ser Leu Trp Asp Gln Ser Leu Lys Pro Cys Val Lys Leu Thr Pro
                85                  90                  95

Leu Cys Val Thr Leu Gln Cys Thr Asn Val Thr Asn Asn Ile Thr Asp
            100                 105                 110

Asp Met Arg Gly Glu Leu Lys Asn Cys Ser Phe Asn Met Thr Thr Glu
        115                 120                 125

Leu Arg Asp Lys Lys Gln Lys Val Tyr Ser Leu Phe Tyr Arg Leu Asp
    130                 135                 140

Val Val Gln Ile Asn Glu Asn Gln Gly Asn Arg Ser Asn Asn Ser Asn
145                 150                 155                 160

Lys Glu Tyr Arg Leu Ile Asn Cys Asn Thr Ser Ala Ile Thr Gln Ala
                165                 170                 175

Cys Pro Lys Val Ser Phe Glu Pro Ile Pro Ile His Tyr Cys Ala Pro
            180                 185                 190

Ala Gly Phe Ala Ile Leu Lys Cys Lys Asp Lys Lys Phe Asn Gly Thr
        195                 200                 205

Gly Pro Cys Pro Ser Val Ser Thr Val Gln Cys Thr His Gly Ile Lys
    210                 215                 220

Pro Val Val Ser Thr Gln Leu Leu Asn Gly Ser Leu Ala Glu Glu
225                 230                 235                 240

Glu Val Met Ile Arg Ser Glu Asn Ile Thr Asn Asn Ala Lys Asn Ile
                245                 250                 255

Leu Val Gln Phe Asn Thr Pro Val Gln Ile Asn Cys Thr Arg Pro Asn
            260                 265                 270

Asn Asn Thr Arg Lys Ser Ile Arg Ile Gly Pro Gly Gln Ala Phe Tyr
        275                 280                 285

Ala Thr Gly Asp Ile Ile Gly Asp Ile Arg Gln Ala His Cys Asn Val
    290                 295                 300

Ser Lys Ala Thr Trp Asn Glu Thr Leu Gly Lys Val Val Lys Gln Leu
305                 310                 315                 320

Arg Lys His Phe Gly Asn Asn Thr Ile Ile Arg Phe Ala Asn Ser Ser
                325                 330                 335

Gly Gly Asp Leu Glu Val Thr Thr His Ser Phe Asn Cys Gly Gly Glu
            340                 345                 350

Phe Phe Tyr Cys Asn Thr Ser Gly Leu Phe Asn Ser Thr Trp Ile Ser
        355                 360                 365
```

```
Asn Thr Ser Val Gln Gly Ser Asn Ser Thr Gly Ser Asn Asp Ser Ile
    370                 375                 380
Thr Leu Pro Cys Arg Ile Lys Gln Ile Ile Asn Met Trp Gln Arg Ile
385                 390                 395                 400
Gly Gln Ala Met Tyr Ala Pro Pro Ile Gln Gly Val Ile Arg Cys Val
                405                 410                 415
Ser Asn Ile Thr Gly Leu Ile Leu Thr Arg Asp Gly Gly Ser Thr Asn
            420                 425                 430
Ser Thr Thr Glu Thr Phe Arg Pro Gly Gly Gly Asp Met Arg Asp Asn
        435                 440                 445
Trp Arg Ser Glu Leu Tyr Lys Tyr Lys Val Val Lys Ile Glu Pro Leu
450                 455                 460
Gly Val Ala Pro Thr Arg Cys Lys Arg Arg Val Val Gly Arg Arg Arg
465                 470                 475                 480
Arg Arg Arg Ala Val Gly Ile Gly Ala Val Phe Leu Gly Phe Leu Gly
                485                 490                 495
Ala Ala Gly Ser Thr Met Gly Ala Ala Ser Met Thr Leu Thr Val Gln
            500                 505                 510
Ala Arg Asn Leu Leu Ser Gly Ile Val Gln Gln Gln Ser Asn Leu Leu
        515                 520                 525
Arg Ala Pro Glu Ala Gln Gln His Leu Leu Lys Leu Thr Val Trp Gly
    530                 535                 540
Ile Lys Gln Leu Gln Ala Arg Val Leu Ala Val Glu Arg Tyr Leu Arg
545                 550                 555                 560
Asp Gln Gln Leu Leu Gly Ile Trp Gly Cys Ser Gly Lys Leu Ile Cys
                565                 570                 575
Cys Thr Asn Val Pro Trp Asn Ser Ser Trp Ser Asn Arg Asn Leu Ser
            580                 585                 590
Glu Ile Trp Asp Asn Met Thr Trp Leu Gln Trp Asp Lys Glu Ile Ser
        595                 600                 605
Asn Tyr Thr Gln Ile Ile Tyr Gly Leu Leu Glu Ser Gln Asn Gln
    610                 615                 620
Gln Glu Lys Asn Glu Gln Asp Leu Leu Ala Leu Asp Gly Thr Lys His
625                 630                 635                 640
His His His His Cys
                645

<210> SEQ ID NO 3
<211> LENGTH: 25
<212> TYPE: PRT
<213> ORGANISM: Artificial Sequence
<220> FEATURE:
<223> OTHER INFORMATION: Synthetic linker
<220> FEATURE:
<221> NAME/KEY: misc_feature
<222> LOCATION: (6)..(25)
<223> OTHER INFORMATION: Any "Gly Gly Gly Ser" group may be present or
      absent

<400> SEQUENCE: 3

Gly Gly Gly Gly Ser Gly Gly Gly Ser Gly Gly Gly Gly Ser Gly
1               5                   10                  15

Gly Gly Ser Gly Gly Gly Gly Ser
            20                  25

<210> SEQ ID NO 4
<211> LENGTH: 5
<212> TYPE: PRT
```

```
<213> ORGANISM: Artificial Sequence
<220> FEATURE:
<223> OTHER INFORMATION: Synthetic linker

<400> SEQUENCE: 4

Gly Gly Gly Gly Ser
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic linker

<400> SEQUENCE: 5

Gly Gly Gly Gly Ser Gly Gly Gly Gly Ser
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: Synthetic linker

<400> SEQUENCE: 7

Gly Gly Gly Gly Ser Gly Gly Gly Gly Ser Gly Gly Gly Gly Ser Gly
1               5                   10                  15

Gly Gly Gly Ser
            20

<210> SEQ ID NO 8
<211> LENGTH: 25
<212> TYPE: PRT
<213> ORGANISM: Artificial Sequence
<220> FEATURE:
<223> OTHER INFORMATION: Synthetic linker

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic linker
<220> FEATURE:
<221> NAME/KEY: misc_feature
<222> LOCATION: (12)..(26)
<223> OTHER INFORMATION: Any "Glu Ala Ala Ala Lys" group may be present
      or absent
```

<400> SEQUENCE: 9

Ala Glu Ala Ala Ala Lys Glu Ala Ala Lys Glu Ala Ala Lys
1               5                   10                  15

Glu Ala Ala Ala Lys Glu Ala Ala Ala Lys Ala
            20                  25

<210> SEQ ID NO 10
<211> LENGTH: 50
<212> TYPE: PRT
<213> ORGANISM: Artificial Sequence
<220> FEATURE:
<223> OTHER INFORMATION: Synthetic linker

<400> SEQUENCE: 10

Leu Glu Ala Glu Ala Ala Ala Lys Glu Ala Ala Lys Glu Ala Ala
1               5                   10                  15

Ala Lys Glu Ala Ala Lys Ala Leu Glu Ala Glu Ala Ala Ala Lys
                20                  25                  30

Glu Ala Ala Lys Glu Ala Ala Lys Glu Ala Ala Lys Ala
        35                  40                  45

Leu Glu
    50

<210> SEQ ID NO 11
<211> LENGTH: 4
<212> TYPE: PRT
<213> ORGANISM: Artificial Sequence
<220> FEATURE:
<223> OTHER INFORMATION: Synthetic linker

<400> SEQUENCE: 11

Gly Gly Ser Gly
1

<210> SEQ ID NO 12
<211> LENGTH: 20
<212> TYPE: PRT
<213> ORGANISM: Artificial Sequence
<220> FEATURE:
<223> OTHER INFORMATION: Synthetic linker
<220> FEATURE:
<221> NAME/KEY: misc_feature
<222> LOCATION: (5)..(20)
<223> OTHER INFORMATION: Any "Gly Gly Ser Gly" group may be present or
      absent

<400> SEQUENCE: 12

Gly Gly Ser Gly Gly Gly Ser Gly Gly Gly Ser Gly Gly Gly Ser Gly
1               5                   10                  15

Gly Gly Ser Gly
            20

<210> SEQ ID NO 13
<211> LENGTH: 4
<212> TYPE: PRT
<213> ORGANISM: Artificial Sequence
<220> FEATURE:
<223> OTHER INFORMATION: Synthetic linker

<400> SEQUENCE: 13

Gly Ser Ala Thr
1

```
<210> SEQ ID NO 14
<211> LENGTH: 30
<212> TYPE: PRT
<213> ORGANISM: Artificial Sequence
<220> FEATURE:
<223> OTHER INFORMATION: Synthetic linker
<220> FEATURE:
<221> NAME/KEY: misc_feature
<222> LOCATION: (7)..(30)
<223> OTHER INFORMATION: Any "Gly Gly Ser Gly Gly Ser" group may be
      present or absent

<400> SEQUENCE: 14

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30
```

ANTIGEN-ADJUVANT COUPLING REAGENTS AND METHODS OF USE

RELATED APPLICATION

This application claims the benefit of U.S. Provisional Patent Application Ser. No. 62/607,691. The entire contents of which is incorporated by reference herein.

GOVERNMENT FUNDING

This invention was made with Government support under Grant Nos. R01 AI125068 and UM1 AI100663 awarded by the National Institutes of Health. The Government has certain rights in the invention.

SEQUENCE LISTING

The instant application contains a Sequence Listing which has been submitted electronically in ASCII format via EFS-Web and is hereby incorporated by reference in its entirety. Said ASCII copy, created Aug. 12, 2019, is named "MITN-044_Sequence-Listing.txt" and is 11,649 Kilobytes in size.

BACKGROUND

Vaccination is a medical treatment intended to induce an immune response against antigens present in the vaccine. Vaccines have saved millions of lives over the past century, in addition to reducing to near eradication many infectious diseases that once caused high levels of morbidity and mortality worldwide.

One factor that limits the activity of current vaccines is insufficient retention of the antigen in the host: resulting in poor targeting to lymph nodes—where immune responses are primed, and insufficient response to the antigen to protect against the disease. Among strategies that promote antigen immunogenicity are those that render vaccine antigens particulate, those that polymerize or emulsify vaccine antigens, methods of encapsulating vaccine antigens, ways of increasing host immune responses, and methods that target vaccine antigens to antigen presenting cells (Nossal, 1999, In: Fundamental Immunology. Paul (Ed.), Lippincott-Raven Publishers, Philadelphia, Pa.; Vogel and Powell, 1995, In: Vaccine Design. The Subunit and Adjuvant Approach. Powell and Newman (Eds.), Plenum Press, NY, N.Y. p. 141). Among these strategies, the use of adjuvants in vaccines is well known. Conventional adjuvants, well-known in the art, are diverse in nature.

Adjuvant use is also linked to a risk of adverse events such as toxicity or local inflammation at the site of injection. In order to limit such an adverse reaction, surfactants and other components in the immunogenic composition or vaccine may be reduced; however, the reduction may then result in a decrease in the effectiveness of the vaccine. There is, therefore, a need for novel vaccine compositions that provide sufficient exposure to the antigen for an effective immune response and for compositions that increase safety and stability of the vaccine.

SUMMARY OF THE INVENTION

The present disclosure, is based, at least in part on a surprising discovery that by site-specific engineering of the interaction between antigens and aluminum hydroxide (alum), an immune response to the antigenis enhanced. Accordingly, the present disclosure provides immunogenic compositions for eliciting enhanced humoral immunity to antigens of interest, thereby providing improved vaccines. In one aspect, the disclosure provides an antigen-adjuvant complex comprising: (a) an antigen covalently linked to an antigen-reactive moiety that is coupled, optionally via at least one linker, to a multivalent adjuvant-reactive moiety comprising two or more hydroxyl-replacement groups; and (b) a metal hydroxide adjuvant (e.g., alum), wherein the antigen is conjugated to the metal hydroxide adjuvant via the hydroxyl replacement groups of the multivalent adjuvant-reactive moiety, thereby forming an antigen-adjuvant complex. In some aspects, the antigen is conjugated to a metal hydroxide adjuvant (e.g., alum) via one or more phosphorylated amino acid residues, such as one or more phosphoserine (PS) residues.

Accordingly, in some aspects, the disclosure provides a method to increase an immune response to an antigen in a subject, wherein the antigen is modified to provide site-specific and/or tight binding to a metal hydroxide adjuvant (e.g., alum) via one or more PS residues. In some aspects, the disclosure provides methods and compositions comprising antigens modified to provide tight binding to a metal hydroxide adjuvant (e.g., alum) through a site-specific introduction of multivalent PS peptide-polymer affinity linkers, which undergo ligand exchange reactions with the surface of alum to anchor antigens in an site-specific and/or surface oriented manner on the metal hydroxide adjuvant, such as alum. As a result of such linkage, it was discovered that a PS-linked antigen-adjuvant complex persisted for over 3 weeks at an injection site, while unmodified antigen is cleared form the injection site within days. The antigen-adjuvant complexes of the present disclosure provide an advantage over previous approaches that relied upon non-specific adsorption of antigen to adjuvant. The random crosslinking of antigen to alum particles also results in unpredictable effects on the immune response, and rapid desorption of antigen from alum particles despite the fact that alum itself is retained at the injection sites for weeks.

While in no way being bound by theory, it is believed that the antigen-adjuvant complexes of the disclosure may impact antigen immunogenicity in two ways: First, by virtue of their tight binding to alum via PS linkages, antigens-adjuvant complexes of the disclosure are trafficked with alum particles in vivo, thereby extending the kinetics of vaccine clearance in vivo from a few days to ~3 weeks following immunization. Second, antigens arrive in lymph nodes still bound to alum particles, such that B cells internalize, and are stimulated in vivo by a multivalent array of immobilized antigens presented on alum nanoparticles. Alum is generally believed to act primarily as a depot that remains at the injection site, and phagocytes are known to be capable of internalizing alum particles in vitro. The present disclosure demonstrates that post-immunization, antigen-adjuvant complexes of the disclosure, in particulate form, are detectable in lymph nodes at the whole tissue and single-cell level. Uptake of antigen-displaying alum particles has multiple implications for the B cell response beyond enhanced B cell receptor crosslinking, as this mode of antigen acquisition would increase the amount of antigen acquired compared to uptake of vaccine compositions comprising free protein and alum. Thus, responding B cells may be more competent to receive help from follicular helper T cells and exhibit enhanced intracellular signaling. Accordingly, the disclosure provides compositions and methods to enhance multiple facets of the immune response by changing the kinetics of vaccine accumulation in lymph nodes and alterations in antigen presentation to immune cells. In another aspect, the disclosure provides antigen-adjuvant complexes that are cleared in vivo more slowly than unmodified antigens adsorbed to adjuvants. Without being bound by theory, it is believed that the tightly-bound antigen-adjuvant complex forms multivalent particulate that may be presented and acquired by B cells in vivo.

As described in the working examples herein, administration of antigen-adjuvant complexes of the disclosure resulted in an unexpectedly enhanced germinal center response by over 20-fold, an increased antibody titer by 63-fold, and an increased in long-lived plasma cells in the bone marrow.

It has also been discovered that site-specific conjugation of an antigen (e.g., an HIV antigen) to alum via one or more phosphorylated amino acid residues, such as one or more PS residues, results in an orientation and display of neutralizing epitopes on the alum particles to thereby enhance antigen-specific immune responses to the neutralizing epitope. This discovery thus provides a strategy to overcome the challenge of eliciting sufficient protective or broadly neutralizing immunity against viral entry receptors. A problem with current vaccine approaches is they contain a soluble form of env protein antigen, which exposes non-natural surfaces of the env protein. As a non-limiting example, the trimer base of the HIV Env protein is an irrelevant target for eliciting protective or neutralizing immunity. Upon immunization with soluble env protein vaccine compositions, immunodominant base-directed antibody responses interfere with the induction of protective, neutralizing antibodies. The antigen-adjuvant complexes of the disclosure provide a method for overcoming this challenge by site-specific introduction of alum-binding PS modification on the antigen. The directed orientation of antigen ensures that neutralizing epitopes are exposed to immune cells, thereby providing a strategy for eliciting broadly neutralizing antibodies while masking non-neutralizing immunodominant surfaces on the antigen.

In addition, oriented anchoring of an HIV trimer on alum particles altered the immunodominance pattern of the humoral response by blocking the immunogenic base of the trimer. The present disclosure, thus provides a universally-applicable strategy to enhance multiple facets of humoral immunity to subunit vaccines.

Accordingly, in one aspect, the disclosure provides an antigen-adjuvant complex comprising an antigen and a metal hydroxide adjuvant. The antigen is covalently linked to an antigen-reactive moiety that is coupled, optionally by at least one linker, to a multivalent adjuvant-reactive moiety comprising two or more hydroxyl-replacement groups. The antigen-adjuvant complex is formed when the hydroxyl replacement groups of the multivalent adjuvant-reactive moiety is conjugated to the metal hydroxide adjuvant.

In another aspect, the antigen-reactive moiety comprising of the antigen-adjuvant complex is a sulfhydryl-reactive moiety. In another aspect, the sulfhydryl-reactive moiety of the antigen-adjuvant complex is maleimide. In another aspect, the multivalent adjuvant-reactive moiety of the antigen-adjuvant complex comprises 3, 4, 5, 6, 7, 8, 9, 10, 11, 12, 13, 14, 15, 16, 17, 18, 19, 20 or more hydroxyl-replacement groups. In another aspect, the hydroxyl-replacement group of the multivalent antigen is selected from the group consisting of a fluoride group, a citrate group, a phosphate group, a carbonate group, and a sulfate group. In another embodiment, the hydroxyl-replacement group is a phosphate group. In another embodiment the hydroxyl-replacement group comprises at least one phosphorylated amino acid residue. In yet another embodiment, the phosphorylated amino acid residue is phosphoserine, phosphotyrosine, or phosphothreonine.

In another aspect the antigen-adjuvant complex comprises an antigen covalently linked to an antigen-reactive moiety that is coupled by at least one linker to a multivalent adjuvant-reactive moiety comprising two or more phosphoserine, whereupon antigen-adjuvant complex is formed by the antigen conjugated to the metal hydroxide adjuvant via the phosphoserine residues of the multivalent adjuvant-reactive moiety.

In yet another embodiment, the metal hydroxide adjuvant that forms the antigen-adjuvant complex is aluminum hydroxide, aluminum phosphate, calcium hydroxide, calcium phosphate, iron hydroxide, magnesium hydroxide, barium hydroxide, calcium hydroxide, zinc hydroxide, or zirconium hydroxide.

In yet another embodiment, the antigen-adjuvant complex comprises an antigen having at least one linker comprising 2-12 phosphoserine residues, and the antigen is conjugated to the alum through the phosphoserine residues to alum. In yet another embodiment, the antigen comprises at least one linker comprising 2-8 phosphoserine conjugated to the alum. In another embodiment, the antigen comprises at least one linker comprising 2-4 phosphoserine conjugated to the alum.

In another aspect, the antigen forming the antigen-adjuvant complex is selected from a cancer antigen, a viral antigen, a bacterial antigen, a parasite antigen, or a fungal antigen. In another aspect, the antigen is a viral antigen. In yet another embodiment, the viral antigen is an HIV antigen, an engineered HIV antigen, or an engineered HIV envelope protein or fragment thereof.

In another aspect, the disclosure provides an immunogenic composition comprising the antigen-adjuvant complex disclosed and an additional adjuvant.

In another aspect, the disclosure provides a method for increasing the retention of an antigen at a site of administration by administering to a subject an immunogenic composition that contains the conjugated antigen-adjuvant complex.

In another embodiment, the antigen of the conjugated antigen-adjuvant complex persists at the site of injection for at least one week. In another embodiment, the antigen persists at the site of injection for at least three weeks.

In yet another embodiment, the disclosure provides a method to ensure the continuous release of an antigen to the draining lymph nodes of a subject by administering to the subject the immunogenic composition comprising the conjugated antigen-adjuvant complex disclosed herein.

In another aspect of the disclosure, the antigen-adjuvant complex forms multivalent particulate aggregates. In yet another aspect, the multivalent particulate aggregates are nanoparticles or nanocrystals.

In yet another aspect, the administration of the antigen-adjuvant complex results in uptake of the antigen-adjuvant complex by immune cells in vivo.

In another embodiment, the immune cells taking up the antigen-adjuvant complex are antigen-specific B cells. In another aspect of this disclosure, the administration of the antigen-adjuvant complex results in an enhanced immune response to the antigen. In another aspect, the immune response is enhanced by an increased antibody titer. In another embodiment, the antibody titer is enhanced by at least 20-fold compared to the antibody titer from an administration of an unconjugated antigen-adjuvant composition. In yet another embodiment, enhanced of the immune response is measured by an increase in neutralizing antibody titer. In another aspect of the invention, the administration of the antigen-adjuvant complex results in an enhanced immune response measured by an increase in the number of antibody secreting B cells. In another aspect, the B cells increased in numbers are bone marrow plasma cells. In another embodiment, the administration of the conjugated antigen-adjuvant complex results in a 16-fold increase of the number of antibody secreting B cells compared to the number of antibody-secreting B cells from an administration of an unconjugated antigen-adjuvant composition. In another embodiment, the administration of conjugated antigen-adjuvant complex results in an increase in the number of antigen-specific germinal center B cells.

In another embodiment, the antigen-adjuvant complex comprises an HIV envelope protein or fragment thereof, conjugated to alum via at least one linker comprising 2-12 phosphoserine residues. In another aspect, the HIV envelope antigen-adjuvant complex is conjugated to alum via at least one linker comprising 2-10 phosphoserine residues, 2-6 phosphoserine residues, or 2-4 phosphoserine residues. In yet another aspect, the HIV envelop antigen-adjuvant complex comprises an HIV envelop protein immobilized by site-specific conjugation to the adjuvant surface, and this immobilization is able to selectively present HIV envelop epitopes to immune cells.

In another aspect, the disclosure provides a method of directing the specificity of an immune response in a subject by administering to a subject an immunogenic composition comprising the antigen-adjuvant complex, wherein one or more epitopes of the antigen is masked by site-specific conjugation of the antigen to the adjuvant surface via the hydroxyl replacement groups on the multivalent adjuvant reactive moiety.

In another embodiment, administration of the antigen-adjuvant complex having the masked epitopes results in the immune response to be directed to an unmasked epitope on the antigen, and thus eliciting one or more protective neutralizing antibodies. In yet another embodiment, the administration of antigen-adjuvant complex in which the HIV envelope trimer base is masked by site-specific conjugation of the HIV trimer on alum particles results in directing the immune response away from eliciting non-neutralizing antibodies.

The present disclosure also provides a reagent useful for the adsorption of an antigen to an adjuvant, wherein the reagent provides a multivalent adjuvant-reactive moiety comprising a plurality of hydroxyl-replacement groups. In addition, the present disclosure is based, at least in part, on the discovery that an immunogenic composition comprising an antigen absorbed to an adjuvant via a multivalent adjuvant-reactive moiety may be used to enhance the immunogenicity of an antigen.

Accordingly, in one aspect, the disclosure provides an antigen-adjuvant coupling reagent, wherein the antigen-adjuvant coupling reagent comprises an antigen-reactive moiety, a multivalent adjuvant-reactive moiety comprising two or more hydroxyl-replacement groups, and optionally with at least one linker, wherein the antigen-reactive moiety is operatively linked, optionally by the at least one linker, to the multivalent adjuvant-reactive moiety, wherein the antigen-reactive moiety covalently binds to a reactive group present on an antigen, and wherein the multivalent adjuvant-reactive moiety interacts with two or more hydroxyl groups present in an adjuvant, thereby coupling the antigen to the adjuvant.

In some embodiments, the antigen-reactive moiety comprises a sulfhydryl-reactive moiety. In some embodiments, the sulfhydryl-reactive moiety is a maleimide.

In some embodiments, the reactive group is a sulfhydryl group.

In some embodiments, the multivalent adjuvant-reactive moiety comprises 3-4, 3-5, 4-6, 5-7, 6-8, 7-9, 8-10, 9-11, 10-12, 11-13, 12-14, 13-15, 14-17, 15-18, 16-20, or more hydroxyl-replacement groups. In some embodiments, the multivalent adjuvant-reactive moiety comprises 3, 4, 5, 6, 7, 8, 9, 10, 11, 12, 13, 14, 15, 16, 17, 18, 19, 20 or more hydroxyl-replacement groups. In some embodiments, the multivalent adjuvant-reactive moiety comprises about 3-10, about 3-15, or about 3-20 hydroxyl-replacement groups. In some embodiments, the multivalent adjuvant-reactive moiety comprises 3 hydroxyl-replacement groups. In some embodiments, the multivalent adjuvant-reactive moiety comprises 4 hydroxyl-replacement groups. In some embodiments, the multivalent adjuvant-reactive moiety comprises 5 hydroxyl-replacement groups.

In some embodiments, the hydroxyl-replacement group is selected from the group consisting of a fluoride group, a citrate group, a phosphate group, a carbonate group, and a sulfate group. In some embodiments, the hydroxyl-replacement group is a phosphate group. In some embodiments, the hydroxyl-replacement group comprises phosphorylated amino acid residues. In some embodiments, the phosphorylated amino acid residue is selected from phosphoserine, phosphotyrosine, and phosphothreonine. In some embodiments, the phosphorylated amino acid residue is phosphoserine.

In some embodiments, the antigen-adjuvant coupling reagent comprises at least one linker. In some embodiments, the at least one linker is polyethylene glycol.

In some embodiments, the adjuvant is a metal hydroxide adjuvant. In some embodiments, the metal hydroxide adjuvant is selected from aluminum hydroxide, aluminum phosphate, calcium hydroxide, calcium phosphate, iron hydroxide, magnesium hydroxide, barium hydroxide, calcium hydroxide, zinc hydroxide, and zirconium hydroxide.

In another aspect, the disclosure provides an immunogenic composition comprising an antigen-adjuvant coupling reagent, an antigen, and optionally a metal hydroxide adjuvant, wherein the reagent is covalently linked to the antigen, and wherein the antigen is coupled to the metal hydroxide adjuvant, when present, via the reagent, thereby forming an antigen-adjuvant complex. In some embodiments, the antigen is adsorbed to the surface of the metal hydroxide adjuvant via the reagent, thereby forming an antigen-adjuvant complex. In some embodiments, adjuvant is aluminum hydroxide or aluminum phosphate.

In some embodiments, the antigen is selected from a cancer antigen, a viral antigen, a bacterial antigen, a parasite antigen, and a fungal antigen. In some embodiments, the antigen is a viral antigen. In some embodiments, the viral antigen an HIV antigen. In some embodiments, the HIV antigen is gp120 or gp140. In some embodiments, the viral antigen is an engineered HIV antigen. In some embodiments, the engineered HIV antigen is eOD. In some embodiments, the engineered HIV antigen is SOSIP.

In some embodiments, the antigen is oriented relative to the surface of the adjuvant, and wherein the orientation of the antigen blocks or inhibits recognition of one or more epitopes by the immune system. In some embodiments, the orientation of the antigen relative to the adjuvant increases broadly neutralizing antibody titers.

In another aspect, the disclosure provides a vaccine comprising an immunogenic composition described herein and optionally, a second or additional adjuvant.

In some aspects, the antigen-adjuvant complexes of the disclosure are delivered in a particulate form. The complexes and methods of the disclosure are broadly applicable to diverse subunit vaccines and provide particulate vaccine formulations. Current strategies formulate antigens in a multivalent, submicron particulate form to enhance B cell receptor crosslinking. However, particulate formulations of vaccine candidates often take the form of virus-like particles, which must be custom-designed for each antigen. Accordingly, the present disclosure provides improved compositions and methods of formulating an antigen-adjuvant complex in a multivalent, particulate form. In another aspect, the disclosure, provides a method to obtain submicron, multivalent particulate vaccine.

In another aspect, the disclosure provides a multivalent-particulate vaccine comprising an antigen-adjuvant complex bound via PS linkages that is presented to and internalized by immune cells. In some embodiments, the antigen-adjuvant complex comprises multivalent particulate aggregates that are nanoparticles or nanocrystals.

In another aspect, the disclosure provides a method for increasing the retention of an antigen in a subject at a site of administration, the method comprising administering a vaccine described herein. In another aspect, the disclosure provides a method for the continuous release of an antigen to the draining lymph nodes of a subject, the method comprising administering a vaccine described herein. In one embodiment, the antigen-adjuvant is presented to B cells as multivalent, particulate aggregates. In another embodiment, the retention of an antigen-adjuvant in the site of administration persisted over weeks. In another aspect, the disclosure provides a method for treating cancer or an infectious disease in a subject in need thereof, the method comprising administering a vaccine described herein, thereby treating the subject. In another aspect, the disclosure provides a method for increasing an immune response in a subject, the method comprising administering a vaccine described herein. In another aspect, the disclosure provides a method for increasing antigen-specific antibody secreting B cells in a subject, the method comprising administering a vaccine described herein. In another aspect, the disclosure provides a method for increasing bone marrow plasma cells. In yet another aspect, the disclosure provides a method for increasing germinal center B cells.

In another aspect, the disclosure provides a nucleic acid molecule encoding an antigen described herein. In another aspect, the disclosure provides a recombinant expression vector comprising a nucleic acid molecule encoding an antigen described herein. In another aspect, the disclosure provides a host cell transformed with a recombinant expression vector comprising a nucleic acid molecule encoding an antigen described herein.

In another aspect, the disclosure provides a method of making an immunogenic composition described herein the method comprising: providing a host cell comprising a nucleic acid sequence that encodes an antigen; maintaining the host cell under conditions in which the antigen is expressed; obtaining the antigen; contacting the antigen with an antigen-adjuvant coupling reagent under conditions wherein the reagent covalently links to the antigen; obtaining the antigen covalently linked to the reagent; optionally coupling or adsorbing the antigen to an adjuvant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A provides a schematic depicting the chemical structure of maleimide-phosphoserine coupling reagents comprising phosphoserines and a schematic of a protein antigen comprising a solvent-exposed, free sulfhydryl group (—SH). FIG. 1B provides a schematic depicting the chemical structure of maleimide-phosphoserine coupling reagents, wherein the maleimide moiety is covalently linked to a thiol group comprising a protein antigen via a thioether linkage. FIG. 1C provides a schematic generally depicting the binding and orientation of the coupling reagent-antigen conjugate when coupled or adsorbed to alum. FIG. 1D provides a line graph showing the adsorption of a model protein, cytochrome c, onto alum as a function of protein concentration as determined by protein UV-absorbance at 280 nm.

FIG. 6A provides a schematic of potential release of free antigen vs. release of antigen-displayed alum particles at the injection site. FIG. 6B provides a line graph of calcium signaling measurement by a fluorescence reporter in glVRC01-expressing human B cells at ~50 sec following incubation with eOD (50 nM) in the presence or absence of alum (10 µg/mL). FIG. 6C provides a fluorescent image of glVRC01-expressing B cells that were incubated with fluorescent Ser4-eOD (50 nM) and fluorophore-tagged alum for 1 hour, and then imaged by confocal microscopy. (scale bars=10 µm). FIG. 6D provides a fluorescent image of glVRC01-expressing B cells that were incubated with fluorescent PS8-eOD (50 nM) and fluorophore-tagged alum for 1 hour, and then imaged by confocal microscopy. (scale bars=10 µm). FIG. 6E provides a TEM section of a Ramos B cells following 1 hour incubation with alum and PS8-eOD (scale bar 200 nm).

FIG. 11A provides a timeline of an adoptive transfer experiment. C57BL/6 mice (n=5-6/group) were adoptively transferred with 1×10⁶ GFP⁺ CTV⁺ VRC01$^{gHL}$ B cells, and then were immunized intraperitoneally with 5 μg AF$^{647}$-labelled Ser4-eOD5 or PS8-eOD5 together with 100 μg alum. FIG. 11B provides flow cytometry analysis of VRC01$^{gHL}$ B cells from the spleen showing uptake of AF$^{647}$-labeled eOD-GT5. Dotted lines indicate background signal in unimmunized controls. FIG. 11C provides a line graph reflecting quantification of eOD-AF$^{647}$ fluorescence on VRC01$^{gHL}$ cells. FIG. 11D provides flow cytometric analysis of VRC0$^{gHL}$ cell activation as assessed by CD86 expression. FIG. 11E provides a bar graph reflecting eOD-AF$^{647}$ fluorescence intensity of VRC01$^{gHL}$ cells. Pooled results (or representative data) from two independent experiments. FIG. 11F provides bar graphs reflecting alum-AF$^{488}$ fluorescence intensity of VRC01$^{gHL}$ cells. Pooled results (or representative data) from two independent experiments. FIG. 12A provides fluorescent analysis of spleen sections from mice immunized intraperitoneally with 10 μg of AF647-labeled PS8-eOD-GT8 and 100 μg Cy3-PS4-labeled alum (left scale bar=1 mm, middle and right scale bars=100 μm). FIG. 12B provides fluorescent analysis of spleen sections from mice immunized intraperitoneally with 10 μg of AF647-labeled Ser4-eOD-GT8 and 100 μg Cy3-PS4-labeled alum (left scale bar=1 mm, middle and right scale bars=100 μm). FIG. 12C provides a line graph of CD86 expression from C57BL/6 mice (n=4-8/group) adoptively transferred with 1×10⁶ CTV⁺ VRC10$^{gHL}$ cells and immunized with 5 μg AF$^{647}$-labeled Ser4-eOD-GT8 or PS8-eOD-GT8 and 100 μg alum. FIG. 12D provides a line graph of divided CTV$^{lo}$ VRC01$^{gHL}$ cells from C57BL/6 mice (n=4-8/group) adoptively transferred with 1×10⁶ CTV⁺ VRC01$^{gHL}$ cells and immunized with 5 μg AF$^{647}$-labeled Ser4-eOD-GT8 or PS8-eOD-GT8 and 100 μg alum.

FIG. 18A provides IgG titers were analyzed over time from BALB/c mice (n=5/group) were immunized with 5 μg eOD (with or without PS linker), 50 μg alum, and 5 μg saponin adjuvant. FIG. 18B provides serum IgG titers collected at 6 weeks from BALB/c mice (n=5/group) that were immunized with 50 µg alum and 5 µg eOD by subcutaneous or intramuscular routes. FIG. 18C provides representative ELISPOT wells and bar graphs three months after immunization as in FIG. 18A, eOD-specific antibody-secreting cells from bone marrow were assayed by ELISPOT. FIG. 18D provides flow cytometric analysis of germinal center responses of dLN on day 9 after BALB/c mice (n=5/group) were immunized with 5 µg eOD and 50 µg alum by subcutaneous route. Shown are representative flow cytometry plots.

FIG. 21A provides illustration of antigenicity analysis of SOSIP trimer captured on VRC01-coated ELISA plates (1), SOSIP-PS4 captured on VRC01-coated ELISA plates (2), or SOSIP-PS4 captured on alum-coated ELISA plates (3). Shown are raw ELISA absorbances for binding of indicated monoclonal antibodies added at 0.1 µg/mL. BALB/c mice were immunized with 2 µg SOSIP or SOSIP-PS4 mixed with 50 µg alum on days 0 and 21. FIG. 21B provides raw ELISA dilution curves for day 63 SOSIP-specific IgG assessed in the presence or absence of 20 µg/mL competing base-binding monoclonal Ab. FIG. 21C provides a bar graph of area under the curve of ELISA signal in the presence of base-blocking Ab (normalized to AUC in the absence of base blocking Ab. FIG. 21D provides dot plot analysis of His tag-specific IgG titers assessed by ELISA at day 63. *, $p<0.05$; , $p<0.01$; *, $p<0.001$ by Student's t-test. FIG. 21E provides dot plot analysis of SOSIP gp120-specific IgG titers assessed by ELISA at day 63. *, $p<0.05$; , $p<0.01$; *, $p<0.001$ by Student's t-test.

DETAILED DESCRIPTION OF THE INVENTION

Figure 2A:
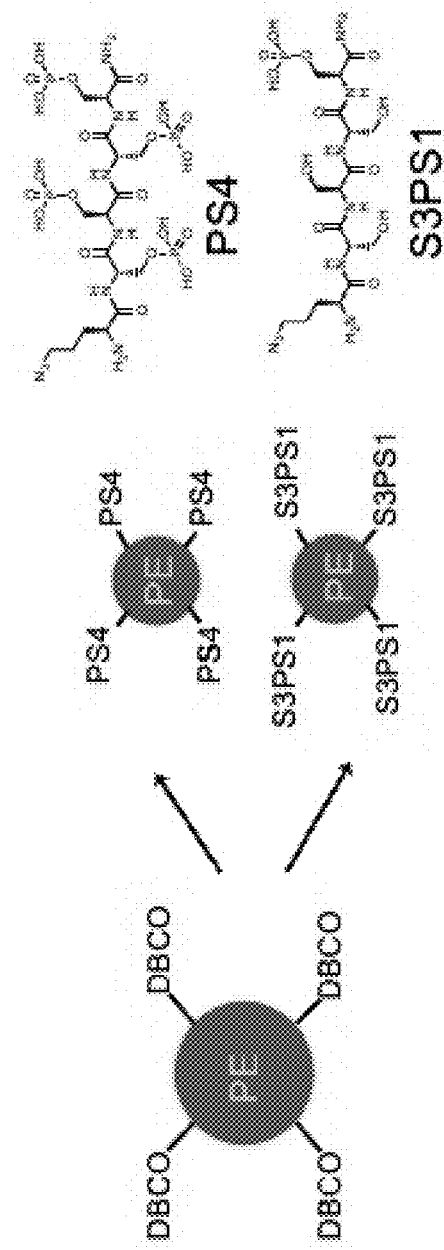
FIG. 2A provides a depiction of peptide linkers of equivalent peptide length, comprising an azide functional group linked to either 4 phosphoserines, or 3 serines and 1 phosphoserine.

The present disclosure provides immunogenic compositions for eliciting enhanced humoral immunity to antigens of interest, thereby providing improved vaccines. In one aspect, the disclosure provides an antigen-adjuvant complex comprising: (a) an antigen covalently linked to an antigen-reactive moiety that is coupled, optionally via at least one linker, to a multivalent adjuvant-reactive moiety comprising two or more hydroxyl-replacement groups; and (b) a metal hydroxide adjuvant (e.g., alum), wherein the antigen is conjugated to the metal hydroxide adjuvant via the hydroxyl replacement groups of the multivalent adjuvant-reactive moiety, thereby forming an antigen-adjuvant complex. In some aspects, the antigen is conjugated to a metal hydroxide adjuvant (e.g., alum) via one or more phosphorylated amino acid residues, such as one or more phosphoserine (PS) residues.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "adjuvant" refers to any substance that acts to augment and/or direct antigen-specific immune responses when used in combination with specific antigens. When combined with a vaccine antigen, adjuvant increases the immune response to the vaccine antigen as compared to the response induced by the vaccine antigen alone. Adjuvants help drive immunological mechanisms and shape the output immune response to vaccine antigens.

As used herein, the term "adjuvant-antigen complex" is used to refer to an antigen covalently linked to an antigen-adjuvant coupling reagent, wherein the antigen linked to the coupling reagent is adsorbed to a metal hydroxide adjuvant by ligand exchange to form a complex.

As used herein, the term "mask" refers to the blocking affected by immobilizing an antigen to an adjuvant surface. In some embodiments, during site-directed conjugation of antigen to adjuvant, PS-linkers are added to defined residues on the antigen and thus control the orientation of the antigen relative to the alum particle. Consequently, epitopes situated in apposition to the alum particle surface are obscured by their proximity to alum. Masked epitopes are thus not displayed to the immune system and would not elicit an immune response.

Methods for determining whether an epitope is masked are known to those of skill in the art. For example, such methods include, but are not limited to, testing serum obtained from an immunization regimen in competitive ELISA with an antibody that binds the epitope of interest, or a plasmon resonance assay such as Biacore, or evaluating binding of a sample to mutant antigens that lack the epitope of interest compared to binding to a wild-type antigen.

As used herein, the term "nanocrystal" refer to submicron crystalline particles less than 100 nm in dimension. In some embodiments, when nanocrystals form aggregates, the size of the aggregates may exceed 100 nm.

As used herein, the term "nanoparticle" refers to submicron particles less 100 nm in dimension. In some embodiments, when nanoparticles form aggregates, the size of the aggregates may exceed 100 nm.

As used herein, the term "aggregate" refers to non-amorphous cluster or collection of particles, as is determinable by electron microscopy.

As used herein, the term "alanine scanning" refers to a technique used to determine the contribution of a specific wild-type residue to the stability or function(s) (e.g., binding affinity) of given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., cancer, including prophylaxis, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "antagonist" refers to any molecule that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides, antisense oligonucleotides, small organic molecules, etc. In some embodiments, inhibition in the presence of the antagonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), Forte Bio© systems, and radioimmunoassay (RIA). These assays determine the ability of an antagonist to bind the polypeptide of interest (e.g., a receptor or ligand) and therefore indicate the ability of the antagonist to inhibit, neutralize or block the activity of the polypeptide. Efficacy of an antagonist can also be determined using functional assays, such as the ability of an antagonist to inhibit the function of the polypeptide or an agonist. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antigenic formulation" or "antigenic composition" or "immunogenic composition" refers to a preparation which, when administered to a vertebrate, especially a mammal, will induce an immune response.

The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "antigen-reactive moiety" refers to a chemical moiety comprising a reactive or functional group that targets by reacting directly with, either spontaneously or after activation through contact with a catalyst or stimulus (e.g., light), an accessible reactive or functional group of a polypeptide comprising an antigen or a reactive or functional group comprising a pendant (e.g. oligosaccharide) attached to a polypeptide comprising an antigen, to produce a covalent linkage.

As used herein, the term "cancer-specific immune response" refers to the immune response induced by the presence of tumors, cancer cells, or cancer antigens. In certain embodiments, the response includes the proliferation of cancer antigen specific lymphocytes. In certain embodiments, the response includes expression and upregulation of antibodies and T-cell receptors and the formation and release of lymphokines, chemokines, and cytokines. Both innate and acquired immune systems interact to initiate antigenic responses against the tumors, cancer cells, or cancer antigens. In certain embodiments, the cancer-specific immune response is a T cell response.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The anti-CD137 antibodies and tumor antigen-targeting antibodies described herein can be used to treat patients who have, who are suspected of having, or who may be at high risk for developing any type of cancer, including renal carcinoma or melanoma. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

As used herein the term "compete", when used in the context of antigen-binding proteins (e.g., immunoglobulins, antibodies, or antigen-binding fragments thereof) that compete for binding to the same epitope, refers to a interaction between antigen-binding proteins as determined by an assay (e.g., a competitive binding assay; a cross-blocking assay), wherein a test antigen-binding protein (e.g., a test antibody) inhibits (e.g., reduces or blocks) specific binding of a reference antigen-binding protein (e.g., a reference antibody) to a common antigen.

As used herein, the term "crosslinking" refers to the process of chemically joining or linking two or more molecules involving a reaction in which a covalent bond is formed.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in SEQ ID NO: 1 or SEQ ID NO: 2. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in SEQ ID NO: 1 or SEQ ID NO: 2In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in SEQ ID NO: 1 or SEQ ID NO: 2 In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence.

In certain embodiments, the antigens of the disclosure are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like.

It will also be understood by one of ordinary skill in the art that the antigens suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The antigens suitable for use in the methods disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term antigen "cross-presentation" refers to presentation of exogenous protein antigens to T cells via MHC class I and class II molecules on APCs.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a determinant or site on an antigen to which an antigen-binding protein (e.g., an immunoglobulin, antibody, or antigen-binding fragment) specifically binds. The epitopes of protein antigens can be demarcated into "linear epitopes" and "conformational epitopes". As used herein, the term "linear epitope" refers to an epitope formed from a contiguous, linear sequence of linked amino acids. Linear epitopes of protein antigens are typically retained upon exposure to chemical denaturants (e.g., acids, bases, solvents, cross-linking reagents, chaotropic agents, disulfide bond reducing agents) or physical denaturants (e.g. thermal heat, radioactivity, or mechanical shear or stress). In some embodiments, an epitope is non-linear, also referred to as an interrupted epitope. As used herein, the term "conformational epitope" refers to an epitope formed from noncontiguous amino acids juxtaposed by tertiary folding of a polypeptide. Conformational epitopes are typically lost upon treatment with denaturants. A epitope typically includes at least 3, 4, 5, 6, 7, 8, 9, 10, 11, 12, 13, 14 or 15 amino acids in a unique spatial conformation. Generally, an antibody, or antigen-binding fragment thereof, specific for a particular target molecule will preferentially recognize and bind to a specific epitope on the target molecule within a complex mixture of proteins and/or macromolecules.

As used herein, the term "epitope mapping" refers to a process or method of identifying the binding site, or epitope, of an antibody, or antigen binding fragment thereof, on its target protein antigen. Epitope mapping methods and techniques are provided herein.

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (See, e.g., Lonberg et al., (1994) *Nature* 368(6474): 856-859); Lonberg, (1994) *Handbook of Experimental Pharmacology* 113: 49-101; Lonberg & Huszar, (1995) *Intern. Rev. Immunol.* 13:65-93, and Harding & Lonberg, (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e. humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, the term "hydroxyl-replacement moiety" or "hydroxyl-replacing moiety" refers to a chemical moiety or group that is effective to substitute for a surface hydroxyl group comprising a metal hydroxide adjuvant.

The terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an vaccine).

The term "in vitro" refers to processes that occur in an artificial environment, e.g., in a test tube or reaction vessel, in cell culture, in a Petri dish, etc., rather than within an organism (e.g., animal, plant, or microbe). The term "in vivo" refers to processes that occur in a living organism.

As used herein, the term "isolated antibody" is intended to refer to an antibody which is substantially free of other antibodies having different antigenic specificities. An isolated antibody that specifically binds to an epitope may, however, have cross-reactivity to other proteins or antigens of interest from different species. However, the antibody continues to display specific binding to an antigen of interest in a specific binding assay as described herein. In addition, an isolated antibody is typically substantially free of other cellular material and/or chemicals.

As used herein the term "KD" or "K$_D$" refers to the equilibrium dissociation constant of a binding reaction between an antibody and an antigen. The value of K$_D$ is a numeric representation of the ratio of the antibody off-rate constant (kd) to the antibody on-rate constant (ka). The value of K$_D$ is inversely related to the binding affinity of an antibody to an antigen. The smaller the K$_D$ value the greater the affinity of the antibody for its antigen. Affinity is the strength of binding of a single molecule to its ligand and is typically measured and reported by the equilibrium dissociation constant (K$_D$), which is used to evaluate and rank order strengths of bimolecular interactions.

As used herein, the term "kd" or "k$_d$" (alternatively "koff" or "k$_{off}$") is intended to refer to the off-rate constant for the dissociation of an antibody from an antibody/antigen complex. The value of kd is a numeric representation of the fraction of complexes that decay or dissociate per second, and is expressed in units $sec^{-1}$.

As used herein, the term "ka" or "k$_a$" (alternatively "kon" or "k$_{on}$") is intended to refer to the on-rate constant for the association of an antibody with an antigen. The value of ka is a numeric representation of the number of antibody/antigen complexes formed per second in a 1 molar (1M) solution of antibody and antigen, and is expressed in units $M^{-1}sec^{-1}$.

As used herein, the terms "linked," "fused", or "fusion", are used interchangeably. These terms refer to the joining together of two more elements, groups, components, domains, or moieties by whatever means including chemical conjugation or recombinant means. Relatedly, as used herein, the term "linker" refers to a chemical group or domain that joins two or more elements, groups, components, domains, or moieties. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

As used herein, the term "multivalent adjuvant-reactive moiety" refers to a reactive moiety comprising a plurality of hydroxyl-replacement groups, wherein each of the hydroxyl-replacement groups is effective to substitute for surface hydroxyl groups of a metal hydroxide adjuvant, thereby binding to an adjuvant in a multivalent fashion.

As used herein, the term "monoclonal antibody" refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In some embodiments, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "neoantigen" refers to an antigen that has at least one alteration that makes it distinct from the corresponding wild-type, parental antigen, e.g., via mutation in a tumor cells or post-translational modification specific to a tumor cell. A neoantigen can include a polypeptide sequence or a nucleotide sequence. A mutation can include a frameshift or non-frameshift deletion, missense or nonsense substitution, splice site alteration, genomic rearrangement or gene fusion, or any genomic or expression alternative giving rise to a neoantigen open reading frame. A mutation can also include a splice variant. Post-translational modifications specific to a tumor cell can include aberrant phosphorylation. Post-translational modifications specific to a tumor cell can also include a proteasome-generated splice antigen. See Liepe et al., A large fraction of HLA class I ligands are proteasome-generated spliced peptides, Science, 2016 Oct. 21; 354 (6310): 354-358. In some embodiments, the neoantigen is a "tumor neoantigen", which is a neoantigen present in a subject's tumor cell or tissue but not in a subject's corresponding normal cell or tissue.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "operably linked" refers to the linkage of a first element to a second element such that the first element and second element are placed in a functional relationship. For example, when a first reactive moiety or group is "operably linked" to a second reactive moiety or group, the function or reactivity of the first and second moieties are linked. For example, a nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

As used herein, the term "paratope", also "antigen-binding site" refers to a portion of an antibody, or antigen-binding fragment thereof, which recognizes and binds to an epitope on an antigen, comprising the set of complementarity determining regions (CDRs) located within variable heavy and light chains.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, "tumor antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, (xi) neoantigens and (xii) any other type of antigen or antigen-presenting cell or material that is associated with a cancer or a tumor.

As used herein, the term "tumor-associated antigen" or "TAA" refers an immunogenic molecule, such as a protein, that is generally expressed at a higher level in tumor cells than in non-tumor cells, in which it may not be expressed at all, or only at low levels. In some embodiments, tumor-associated structures which are recognized by the immune system of the tumor-harboring host are referred to as tumor-associated antigens. In some embodiments, a tumor-associated antigen is a universal tumor antigen if its broadly expressed by most tumors. In some embodiments, tumor-associated antigens are differentiation antigens, mutational antigens, overexpressed cellular antigens or viral antigens.

As used herein, the term "tumor specific antigen" or "TSA" refers to an immunogenic molecule, such as a protein, that is unique to a tumor cell. Tumor specific antigens are exclusively expressed in tumor cells.

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, "vaccine" refers to a formulation which contains an immunogenic composition as described herein, combined with an adjuvant, which is in a form that is capable of being administered to a vertebrate and which induces a protective immune response sufficient to induce immunity to prevent and/or ameliorate an infection or disease and/or to reduce at least one symptom of an infection or disease and/or to enhance the efficacy of another dose of the synthetic nanoparticle. Typically, the vaccine comprises a conventional saline or buffered aqueous solution medium in which a composition as described herein is suspended or dissolved. In this form, a composition as described herein is used to prevent, ameliorate, or otherwise treat an infection or disease. Upon introduction into a host, the vaccine provokes an immune response including, but not limited to, the production of antibodies and/or cytokines and/or the activation of cytotoxic T cells, antigen presenting cells, helper T cells, dendritic cells and/or other cellular responses.

As used herein, "protective" immune response refers to cell mediated and/or humoral (antibody) mediated immune response that will prevent or ameliorate a disease or infection. Protective humoral immune response or humoral immunity often involve the induction of broadly neutralizing antibodies that recognize specific epitopes on an antigen. For elicitation of protective humoral immunity by vaccination, B cells must be activated and enter germinal centers, where they proliferate and mutate their antibody genes toward enhanced recognition of an antigen. A portion of these cells must then differentiate into either long-lived plasma cells that secrete antibody constitutively or memory B cells that participate in a recall response on re-exposure to the pathogen.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Antigen-Reactive Moieties

In some embodiments provided by the disclosure, the antigen-reactive moiety comprises a reactive or functional group selected from the group consisting of an amine-reactive group, a carboxyl-to-amine reactive group, a sulfhydryl-reactive group, an aldehyde- or carbonyl-reactive group, a hydroxyl reactive group, an azide-reactive group, and a photo-reactive group.

In some embodiments, the antigen-reactive moiety comprises an amine-reactive group. Non-limiting examples of amine-reactive groups include isothiocyanate, isocyanate, sulfonyl chloride, aldehydes, carbodiimide, acyl azide, anhydride, fluorobenzene, carbonate, N-hydroxysuccinimide ester (NHS ester), imidoester, epoxide, and fluorophenyl ester. In some embodiments, the antigen-reactive moiety comprises an amine-reactive group selected from the group consisting of N-hydroxysuccinimide ester (NHS ester), sulfo-NHS ester, imidoester, pentafluorophenyl ester, and hydroxymethyl phosphine.

In some embodiments, the antigen-reactive moiety comprises a carboxyl-to-amine reactive group comprising a carbodiimide. In some embodiment, the carbodiimide is EDC. In other embodiments, the carbodiimide is DCC.

In some embodiments, the antigen-reactive moiety comprises a sulfhydryl-reactive group. Non-limiting examples of sulfhydryl-reactive groups include maleimide, haloacetyl (bromo- or iodo-), pyridyldisulfide, thiosulfonate, and vinylsulfone. In some embodiments, the antigen-reactive moiety comprises a sulfhydryl-reactive group comprising maleimide.

In some embodiments, the antigen-reactive moiety comprises an aldehyde- or carbonyl-reactive group. Examples of aldehyde- or carbonyl-reactive groups include, but are not limited to, hydrazide and alkoxyamine.

In some embodiments, the antigen-reactive moiety comprises a hydroxyl-reactive group. A non-limiting example of hydroxyl-reactive group is isocyanate.

In some embodiments, the antigen-reactive moiety comprises an azide-reactive group. A non-limiting example of an azide-reactive group is phosphine.

In some embodiments, the antigen-reactive moiety comprises a photo-reactive group. Examples of photo-reactive groups include, but are not limited to, phenyl azide, ortho-hydroxyphenyl azide, meta-hydroxyphenyl azide, tetrafluorophenyl azide, ortho-nitrophenyl azide, meta-nitrophenyl azide, diazirine, azido-methylcoumarin, and psoralen.

In some embodiments, the antigen-reactive moiety targets and reacts with a reactive or functional group selected from: a primary amine group (—NH2), a carboxyl group (—COOH), a sulfhydryl group (—SH), a carbonyl group (—CHO), an azide group (—N3).

In some embodiments provided by the disclosure, the antigen-reactive moiety may react with one or more reactive or functional groups comprising polypeptides of interest under conditions wherein the polypeptide is maintained in a folded state (e.g., physiological conditions). In some embodiments, the antigen-reactive moiety reacts with one or more reactive or functional groups of an antigen, such as a sidechain group of Lys, Cys, Ser, Thr, Tyr, His or Arg amino acid residues of the antigen. The antigen-reactive moiety may be amino-reactive, thiol-reactive, hydroxyl-reactive, imidazolyl-reactive or guanidinyl-reactive. Further exemplary reactive or functional groups suitable for the antigen-reactive moiety and methods of using the same are described in Hermanson "Bioconjugate Techniques" 3rd Edition, Academic Press, 2013, herein incorporated by reference in its entirety.

Linkers

In some embodiments, an antigen-adjuvant coupling reagent includes a linker. In some embodiments, an antigen-adjuvant coupling reagent includes a plurality of linkers. In some embodiments, the linker domain is a polypeptide linker, an ethylene glycol linker, or an oligonucleotide linker. In certain aspects, it is desirable to employ a linker to couple an antigen with an adjuvant to form an antigen-adjuvant complex. In some embodiments, the antigen is coupled to the adjuvant via phosphoserine residues linked or tagged to any of the linkers described herein. As used herein, linkers comprising phosphoserine residues are referred herein as "phosphoserine linkers" (PS-linkers). In some embodiment, the PS-linker comprises a polypeptide linker containing phosphoserine residues. In another embodiment the PS-linker comprises 1-12 consecutive PS residues followed by a short poly(ethylene glycol) spacer and N-terminal maleimide functional group. In another embodiment, the maleimide functional group at the N-terminal of the PS-linker is covalently via a thioether linkage to a thiol group on the antigen.

In yet another embodiment, the multiple PS-linkers are conjugated to an antigen protein via azide functional groups and coupled to a DBCO-modified antigen. The linkers of the invention may be employed, for instance, to ensure that an antigen is positioned relative to an adjuvant to ensure proper folding and formation of the antigen or to block or expose particular epitopes. Preferably, a linker compatible with the instant invention will be relatively non-immunogenic and not inhibit any non-covalent association among monomer subunits of a binding protein (e.g. an antibody). Exemplary linker domains are disclosed in U.S. Pat. No. 6,660,843, which is incorporated by reference herein.

In some embodiments, the linker may be a non-cleavable linker or a cleavable linker. A non-cleavable linker may include an amide bond or phosphate bond, and the cleavable linker may include a disulfide bond, acid-cleavable linkage, ester bond, anhydride bond, biodegradable bond, or enzyme-cleavable linkage.

Polypeptide Linkers

In some embodiments, an antigen-adjuvant coupling reagent provided by the disclosure comprises a polypeptide linker to join any antigen-reactive moiety to any multivalent adjuvant-reactive moiety comprising two or more hydroxyl-replacement groups described herein. For example, in some embodiments, a polypeptide linker can be used to covalently link an antigen-reactive moiety comprising a sulfhydryl-reactive moiety to an multivalent adjuvant-reactive moiety comprising two or more hydroxyl-replacement groups, wherein the hydroxyl-replacement group comprises a phosphate group.

In some embodiments, the polypeptide linker is synthetic. As used herein, the term "synthetic" with respect to a polypeptide linker includes peptides (or polypeptides) which comprise an amino acid sequence (which may or may not be naturally occurring) that is linked in a linear sequence of amino acids to a reactive moiety. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring).

In some embodiments, a polypeptide linker comprises or consists of a Gly-Ser linker. As used herein, the term "Gly-Ser linker" refers to a peptide that consists of glycine and serine residues. An exemplary Gly-Ser linker comprises an amino acid sequence of the formula $(Gly_4Ser)_n$ (SEQ ID NO: 3), wherein n is a positive integer (e.g., 1, 2, 3, 4, or 5). In certain embodiments the Gly-Ser linker is $(Gly_4Ser)_1$ (SEQ ID NO: 4). In certain embodiments the Gly-Ser linker is $(Gly_4Ser)_2$ (SEQ ID NO: 5). In certain embodiments the Gly-Ser linker is $(Gly_4Ser)_n$ (SEQ ID NO: 6). In certain embodiments the Gly-Ser linker is $(Gly_4Ser)_4$ (SEQ ID NO: 7). In certain embodiments the Gly-Ser linker is $(Gly_4Ser)_5$ (SEQ ID NO: 8). In certain embodiments, the gly-ser linker may be inserted between two other sequences of the polypeptide linker (e.g., any of the polypeptide linker sequences described herein). In other embodiments, a Gly-Ser linker is attached at one or both ends of another sequence of the polypeptide linker (e.g., any of the polypeptide linker sequences described herein). In yet other embodiments, two or more Gly-Ser linker are incorporated in series in a polypeptide linker.

Other linkers that are suitable for use in any of the antigen-adjuvant coupling reagents described herein are known in the art, for example, the serine-rich linkers disclosed in U.S. Pat. No. 5,525,491, the helix forming peptide linkers (e.g., A(EAAAK)nA (n=2-5) (SEQ ID NO: 9)) disclosed in Arai et al., *Protein Eng* 2001; 14:529-32, and the stable linkers disclosed in Chen et al., *Mol Pharm* 2011; 8:457-65, i.e., the dipeptide linker LE, a thrombin-sensitive disulfide cyclopeptide linker, and the alpha-helix forming linker LEA(EAAAK)$_4$ALEA(EAAAK)$_4$ALE (SEQ ID NO: 10).

Other exemplary linkers include GS linkers (i.e., (GS)n), GGSG (SEQ ID NO: 11) linkers (i.e., (GGSG)n (SEQ ID NO: 12)), GSAT (SEQ ID NO: 13) linkers, SEG linkers, and GGS linkers (i.e., (GGSGGS)n (SEQ ID NO: 14)), wherein n is a positive integer (e.g., 1, 2, 3, 4, or 5). Other suitable linkers for use in the antigen-adjuvant coupling reagents can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers of the invention are at least one amino acid in length and can be of varying lengths. In one embodiment, a polypeptide linker of the invention is from about 1 to about 50 amino acids in length. As used in this context, the term "about" indicates+/− two amino acid residues. Since linker length must be a positive integer, the length of from about 1 to about 50 amino acids in length, means a length of from 1 to 48-52 amino acids in length. In another embodiment, a polypeptide linker of the invention is from about 1-5 amino acids in length. In another embodiment, a polypeptide linker of the invention is from about 5-10 amino acids in length. In another embodiment, a polypeptide linker of the invention is from about 10-20 amino acids in length. In another embodiment, a polypeptide linker of the invention is from about 15 to about 50 amino acids in length.

In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Ethylene Glycol Linkers

In some embodiments, the linker is one or more ethylene glycol (EG) units, more preferably 2 or more EG units (i.e., polyethylene glycol (PEG)). In some embodiments, a linker comprises or consists of a polyethylene glycol (PEG) linker. Polyethylene glycol or PEG refers to a chemical compound composed of repeating ethylene glycol units. An exemplary "PEG linker" comprises a compound of the formula: H—(O—CH2-CH2)n-OH, wherein n is a positive integer (e.g., 1, 10, 20, 50, 100, 200, 300, 400, 500, 600). In some embodiments, the PEG linker is PEG1000. In some embodiments, the PEG linker is PEG2000. In some embodiments, the PEG linker is PEG3000.

In some embodiments, an antigen-adjuvant coupling reagent provided by the disclosure may comprise any polyethylene glycol (PEG) linker to join any antigen-reactive moiety to any multivalent adjuvant-reactive moiety comprising two or more hydroxyl-replacement groups described herein. For example, in some embodiments, a polyethylene glycol (PEG) linker can be used to covalently link an antigen-reactive moiety comprising a sulfhydryl-reactive moiety to an multivalent adjuvant-reactive moiety comprising two or more hydroxyl-replacement groups, wherein the hydroxyl-replacement group comprises a phosphate group.

In some embodiments, the precise number of ethylene glycol (EG) units comprising the antigen-adjuvant coupling reagent may range between about 1 and about 100, between about 20 and about 80, between about 30 and about 70, or between about 40 and about 60 EG units. In some embodiments, the ethylene glycol linker has between about 45 and 55 EG, units. For example, in one embodiment, the ethylene glycol linker has 45 EG units. For example, in one embodiment, the ethylene glycol linker has 48 EG units.

Oligonucleotide Linkers

In some embodiments, the linker is an oligonucleotide. The linker can be have any sequence, for example, the sequence of the oligonucleotide can be a random sequence, or a sequence specifically chosen for its molecular or biochemical properties. In some embodiments, the linker includes one or more series of consecutive adenine (A), cytosine (C), guanine (G), thymine (T), uracil (U), or analog thereof. In some embodiments, the linker consists of a series of consecutive adenine (A), cytosine (C), guanine (G), thymine (T), uracil (U), or analog thereof.

In one embodiment, the linker is one or more guanines, for example between 1-10 guanines. In some embodiments, the linker in an ABP conjugate can include 0, 1, or 2 guanines. In some embodiments, the oligonucleotide comprises phosphorothioate intersubunit linkages.

Hydroxyl-Replacement Groups

The present disclosure provides novel compositions and methods directed to enhancing the immune response resulting from the administration of an antigen to a vertebrate. In accordance with the disclosure, the immune response is enhanced by administering an antigen in a form whereby its presentation to the immune system potentiates a response. For example, changing the duration antigen is available to lymph nodes, or promoting internalization by antigen presenting cells such as, for example, dendritic cells. The invention arises from discoveries that antigens adsorbed to adjuvant particles by electrostatic and other secondary forces alone do not remain adsorbed to a high degree after delivery of the vaccine to a subcutaneous or intramuscular location; that antigens adsorbed to adjuvant particles by ligand exchange do remain adsorbed to a high degree after delivery; and that antigens that remain adsorbed to adjuvant particles following delivery are more readily retained at the site of injection and induce high anti-antigen antibody titers.

The multivalent adjuvant-reactive moiety comprising the coupling reagent provides at least two hydroxyl-replacement groups (e.g., phosphate groups) that are effective to substitute for surface hydroxyl groups of a metal hydroxide adjuvant particle (e.g. alum), thereby coupling or absorbing the antigen to the adjuvant.

Such a composition is referred to herein as an "antigen-adjuvant complex." This substitution occurs by a ligand exchange mechanism, and the substitution results in the formation of an inner-sphere surface complex, including the antigen and the metal hydroxide adjuvant, whereby the antigen is strongly adsorbed to the adjuvant particle. As used herein, the term "ligand exchange" is defined as a substitution, or exchange, of a surface hydroxyl by another ligand, in this case an antigen comprising a hydroxyl-replacement group.

As used herein, the term "metal hydroxide adjuvant" is used to refer to a substance that includes at least one hydroxyl group bound to a metal, that is capable of adsorbing an antigen having a hydroxyl-replacement a moiety, and that is capable of aiding the antigen in eliciting an immune response when delivered to a vertebrate. The metal hydroxide adjuvant also is selected to be one that is biocompatible for humans and non-humans. A preferred metal hydroxide adjuvant or use in accordance with the present invention is an aluminum-containing adjuvant. The term "aluminum-containing adjuvant" is defined as a substance that includes at least one hydroxyl group bound to aluminum. Examples of aluminum-containing adjuvants are aluminum hydroxide adjuvant and aluminum phosphate adjuvant.

A person skilled in the relevant field will appreciate that the term "aluminum hydroxide adjuvant" is used in this field to identify a crystalline aluminum oxyhydroxide compound. Aluminum hydroxide adjuvant has only hydroxyl groups at the surface, covalently bonded to aluminum. The term "aluminum phosphate adjuvant" is used in this field to identify amorphous aluminum hydroxyphosphate. Aluminum phosphate adjuvant has phosphate groups and hydroxyl groups at the surface, covalently bonded to aluminum. Although aluminum-containing adjuvant is the most commonly used vaccine adjuvant, and aluminum hydroxide adjuvant is the only adjuvant currently used in FDA-licensed vaccines for humans in the United States, the principles of the present invention are similarly applicable to metal hydroxide adjuvants other than aluminum-containing adjuvants. As further alternative, non-limiting examples of metal hydroxide adjuvants, the present invention contemplates that iron hydroxide adjuvant and calcium phosphate adjuvant are suitable for use in accordance with the invention.

The present invention also contemplates the use of modified metal hydroxide adjuvants, such as, for example, modified aluminum-containing adjuvants, in vaccine formulations for delivering modified, hydroxyl replacing antigen. As used herein, the term "modified metal hydroxide adjuvant" is used to refer to a metal hydroxide adjuvant in which a fraction of the surface hydroxyl groups have been replaced or modified such that the number of surface hydroxyl groups available for ligand exchange is reduced. One exemplary manner of modifying a metal hydroxide adjuvant in accordance with the invention is by contacting the adjuvant with a phosphate-containing solution for a period of time sufficient to cause phosphate substitution of surface hydroxyl groups to occur (also referred to herein as phosphorylating some of the surface hydroxyl groups). For example, when aluminum hydroxide adjuvant is exposed to phosphate, the phosphate can displace a surface hydroxyl and form an inner-sphere surface complex (covalent bond) with surface aluminum, thereby modifying the surface structure of the aluminum hydroxide adjuvant. Surface hydroxyl groups of aluminum phosphate adjuvant can be phosphorylated in a similar manner.

A metal hydroxide adjuvant can be modified as described in order to alter the density of hydroxyl groups on the surface of adjuvant particles that are available for ligand exchange. Alternatively or in addition, modification of a metal hydroxide adjuvant in this manner may be desirable for other reasons. For example, the disclosure contemplates that a modification in the density of hydroxyl groups on the surface of adjuvant particles will accordingly modify the degree of adsorption or coupling of an immunogenic composition.

Non-limiting examples of hydroxyl-replacement groups include, fluoride groups, citrate groups, phosphate groups, sulfate groups and carbonate groups. Aluminum has a high affinity for phosphate, which can replace surface hydroxyls in a ligand exchange reaction. In some embodiments, the hydroxyl-replacement group comprising an antigen-adjuvant coupling reagent is a phosphate group. Aluminum has even higher affinity for fluorine. In another embodiment, the hydroxyl-replacement group comprising an antigen-adjuvant coupling reagent is a fluorine group.

A antigen can be modified to adsorb, to increase adsorption, or to decrease release from, an adjuvant by providing an antigen that does not include a hydroxyl-replacement moiety and modifying the antigen by adding one or more hydroxyl replacing moieties, via covalent linkage of an antigen-adjuvant coupling reagent to the antigen, wherein, via the moiety, the antigen adsorbs to a metal hydroxide adjuvant by ligand exchange. One manner of achieving this modification, which is particularly well suited for modifying polypeptide antigens, is by inclusion of an amino acid into the antigen that provides a reactive moiety (e.g. cysteine, —SH) and by further contacting the modified antigen comprising a reactive moiety with an antigen-adjuvant coupling reagent.

In some embodiments, the antigens provided by the disclosure are modified to include one or more amino acids (e.g. cysteine) not present in the native form of the antigen for the purpose of creating or increasing the ability of the antigen to react with an antigen-adjuvant coupling reagent. In some embodiments, the disclosure contemplates a site-specific modification of the antigen to orient the antigen relative to the adjuvant surface. Thus, selectively presenting epitopes on the antigens while masking irrelevant epitopes oriented in apposition to the adjuvant surface.

In some embodiments, the disclosure contemplates that an antigen that includes one or more hydroxyl-replacement moieties in its native form can be modified in accordance with the invention to increase the rate of ligand exchange adsorption or to increase the strength of adsorption of the antigen to a metal hydroxide adjuvant.

Antigens

Antigens suitable for inclusion in the immunogenic compositions described herein may be derived from any pathogen (e.g., a bacterial pathogen, a viral pathogen, a fungal pathogen, a protozoan pathogen, a unicellular or a multicellular parasitic pathogen), allergen, or tumor. In some embodiments, the antigen is derived from a virus. Exemplary viruses comprising suitable antigens include, but are not limited to, e.g., respiratory syncytial virus (RSV), hepatitis B virus (HBV), hepatitis C virus (HCV), Dengue virus, herpes simplex virus (HSV; e.g., HSV-I, HSV-II), molluscum contagiosum virus, vaccinia virus, variola virus, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza virus (flu), para-influenza virus, mumps virus, measles virus, papovavirus, hepadnavirus, flavivirus, retrovirus, arenavirus (e.g., Lymphocytic Choriomeningitis Virus, Junin virus, Machupo virus, Guanarito virus, or Lassa virus), norovirus, yellow fever virus, rabies virus, Filovirus (e.g., Ebola virus or marbug virus), hepatitis C virus, hepatitis B virus, hepatitis A virus, Morbilliviruses (e.g., measles virus), Rubulaviruses (e.g., mumps virus), Rubiviruses (e.g., rubella virus), bovine viral diarrhea virus. For example, the antigen can be CMV glycoprotein gH, or gL; Parvovirus; HIV glycoprotein gp120 or gp140, HIV p55 gag, pol; or RSV-F antigen. In some embodiments, the antigen is a viral antigen. In some embodiments, the viral antigen is an HIV antigen comprising gp120 or gp140. In some engineered HIV antigen is an engineered variant of gp120 (engineered Outer Domain, eOD). In some embodiments, the engineered HIV antigen is an engineered variant of gp140 (SOSIP). Further description of eOD and/or SOSIP is provided by WO201605704A3, US20160185825A1, Georgiev et al., (2015) J Virol 89(10):5318-5329, all of which are incorporated herein by reference in their entirety.

In some embodiments, the antigen is derived from a parasite. In some embodiments, the antigen is derived from a species from within the *Plasmodium* genus, such as *P. falciparum*, *P. vivax*, *P. malariae* or *P. ovale*. Thus the immunogenic composition may be used for preparation of a vaccine for immunizing against malaria.

In some embodiments, the antigen is derived from a bacterial pathogen. Exemplary bacterial pathogens include, e.g., *Neisseria* spp, including *N. gonorrhea* and *N. meningitides*; *Streptococcus* spp, including *S. pneumoniae, S. pyogenes, S. agalactiae, S. mutans*; *Haemophilus* spp, including *H. influenzae* type B, non typeable *H. influenzae*, *H. ducreyi*; *Moraxella* spp, including *M. catarrhalis*, also known as *Branhamella catarrhalis*; *Bordetella* spp, including *B. pertussis, B. parapertussis* and *B. bronchiseptica*; *Mycobacterium* spp., including *M. tuberculosis, M. bovis, M. leprae, M. avium, M. paratuberculosis, M. smegmatis*; *Legionella* spp, including *L. pneumophila*; *Escherichia* spp, including enterotoxic *E. coli*, enterohemorragic *E. coli*, enteropathogenic *E. coli*; *Vibrio* spp, including *V. cholera*, *Shigella* spp, including *S. sonnei, S. dysenteriae, S. flexnerii*; *Yersinia* spp, including *Y. enterocolitica, Y. pestis, Y. pseudotuberculosis*, *Campylobacter* spp, including *C. jejuni* and *C. coli*; *Salmonella* spp, including *S. typhi, S. paratyphi, S. choleraesuis, S. enteritidis*; *Listeria* spp., including *L. monocytogenes*; *Helicobacter* spp, including *H pylori*; *Pseudomonas* spp, including *P. aeruginosa*, *Staphylococcus* spp., including *S. aureus, S. epidermidis*; *Enterococcus* spp., including *E. faecalis, E. faecium*; *Clostridium* spp., including *C. tetani, C. botulinum, C. difficile*; *Bacillus* spp., including *B. anthracis*; *Corynebacterium* spp., including *C. diphtheriae*; *Borrelia* spp., including *B. burgdorferi, B. garinii, B. afzelii, B. andersonii, B. hermsii*; *Ehrlichia* spp., including *E. equi* and the agent of the Human Granulocytic Ehrlichiosis; *Rickettsia* spp, including *R. rickettsii*; *Chlamydia* spp., including *C. trachomatis, C. neumoniae, C. psittaci*; *Leptsira* spp., including *L. interrogans*; *Treponema* spp., including *T. pallidum, T. denticola, T. hyodysenteriae*

In certain embodiments, the antigen is derived from a fungal pathogen. Exemplary fungal pathogens include, e.g., *Aspergillus fumigatus, A. flavus, A. niger, A. terreus, A. nidulans, Coccidioides immitis, Coccidioides posadasii, Cryptococcus neoformans, Histoplasma capsulatum, Candida albicans*, and *Pneumocystis jirovecii*.

In certain embodiments, the antigen is derived from a protozoan pathogen. Exemplary protozoan pathogens include, e.g., *Toxoplasma gondii* and *Strongyloides stercoralis*.

In certain embodiments, the antigen is derived from a multicellular parasitic pathogen. Exemplary multicellular parasitic pathogens include, e.g., trematodes (flukes), cestodes (tapeworms), nematodes (roundworms), and arthropods.

In some embodiments, the antigens is derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments, the antigen is derived from a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

In some embodiments, the antigen is oriented relative to the surface of the adjuvant, wherein the orientation of the antigen blocks or inhibits recognition of one or more epitopes by the immune system.

Adjuvants

Aluminium salts ("alum"; aluminum hydroxide, aluminum phosphate) and "Adjuvant System 04" (AS04) are two adjuvants used in commercially available vaccines in the United States. Alum is the most commonly used adjuvant in human vaccination. Additional adjuvants have been approved for use in Europe, and many others are being tested in clinical trials. Non-limiting examples of adjuvants include trehalose-6,6'-dimycolate (TDM), muramyl dipeptide (MDP), pluronic block copolymers, alum solution, aluminium hydroxide, ADJUMER® (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,2S-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methylpropyl)-1H-imidazol-4,5-c)quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-GCn-OCH₃); MURAPALMITINE™ and D-MURAPALMITINE™ (Nac-Mur-L-Thr-D-isoCln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and copolymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearoyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, ISCOMATRIX®, ISCOM; adjuvants suitable for co-stimulation including Tomatine, biopolymers, including PLG, PMM, Inulin; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Immunostimulatory oligonucleotides (such as those including a CpG motif or Poly(I:C) can be used as adjuvants (for example see U.S. Pat. Nos. 6,194,388; 6,207,646; 6,214,806; 6,218,371; 6,239,116; 6,339,068; 6,406,705; and 6,429,199). Exemplary adjuvants also may include biological molecules (a "biological adjuvant"), such as costimulatory molecules. Exemplary biological adjuvants include STING, IL-2, RANTES, GM-CSF, TNF-α, IFN-γ, G-CSF, LFA-3, CD72, B7-1, B7-2, OX-40L and 41 BBL. Adjuvants can be used in combination with the disclosed compositions.

Antigen-Adjuvant Complexes and Immunogenic Compositions

The antigen-adjuvant coupling reagents, antigens, optionally linkers, and adjuvants, described herein, are suitable for use in the antigen-adjuvant complexes and in immunogenic compositions or as components in vaccines. The immunogenic compositions disclosed herein may include an antigen-adjuvant complex, optionally a linker, a second adjuvant, or a combination thereof. Any of the immunogenic compositions described herein may be referred to as a vaccine. When administered to a subject in combination, antigen-adjuvant complex and the second adjuvant can be administered in separate pharmaceutical compositions, or they can be administered together in the same pharmaceutical composition.

An immunogenic composition suitable for use in the methods disclosed herein may include an antigen-adjuvant complex, administered alone, or in combination with one or more additional adjuvants. The adjuvant comprising the antigen-adjuvant complex and/or the one or more additional or second adjuvant may be any of the adjuvants described herein. Adjuvants may include, for example, without limitation, alum (e.g., aluminum hydroxide, aluminum phosphate); saponins purified from the bark of the Q. saponaria tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immuno stimulant, Seppic).

The antigen-adjuvant complex in the immunogenic composition may comprise particulate aggregates comprising nanoparticles or nanocrystals.

The adjuvant or adjuvants comprising an immunogenic composition may also include, for example, without limitation, TLR ligands, such as those discussed above. Adjuvants that act through TLR3 include, without limitation, double-stranded RNA. Adjuvants that act through TLR4 include, without limitation, derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include, without limitation, flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant or adjuvants comprising an immunogenic composition may also include, for example, without limitation, oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

The adjuvant or adjuvants comprising an immunogenic composition may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

Methods of Making an Antigen-Adjuvant Complexes and Immunogenic Compositions

In one aspect, the present disclosure provides antigen-adjuvant complexes and immunogenic compositions for use in vaccine formulations. Antigens provided by the disclosure may be modified or engineered to include, or are synthesized to include, a reactive group amenable to covalent linkage with an antigen-adjuvant coupling reagent provided by the disclosure. In some embodiments, the disclosure provides methods of making an immunogenic composition described herein, the method comprising providing a host cell comprising a nucleic acid sequence an antigen comprising a reactive group, described herein, maintaining the host cell under conditions in which the antigen is expressed, obtaining the antigen, contacting the antigen with an antigen-adjuvant reagent, described herein, under conditions wherein the reagent covalently links to the antigen, obtaining the antigen covalently linked to the reagent, optionally coupling or adsorbing the antigen to an adjuvant.

In some embodiments, the antigen-adjuvant coupling reagent is prepared using solid phase peptide synthesis. Solid phase peptide synthesis is a known process in which amino acid residues are added to peptides that have been immobilized on a solid support. Further description of solid phase peptide synthesis is found in Stawikowski and Fields (2002) Curr Protoc Protein Sci. CHAPTER:Unit-18.1 and Behrendt et al., (2016) J Pept Sci 22(1):4-27, both of which are incorporated herein by reference it their entirety.

In some embodiments, the polypeptides described herein for use as antigens are synthesized in transformed host cells using recombinant DNA techniques. To do so, a recombinant DNA molecule coding for the polypeptide is prepared. Methods of preparing such DNA molecules are well known in the art. For instance, sequences coding for the polypeptides could be excised from DNA using suitable restriction enzymes. Alternatively, the DNA molecule could be synthesized using chemical synthesis techniques, such as the phosphoramidate method. Also, a combination of these techniques could be used. In some embodiments, the antigen is engineered to comprise a non-naturally occurring amino acid comprising a reactive group (e.g. a solvent-exposed cysteine). Methods of engineering the antigen to comprise a non-naturally occurring amino acid include, but are not limited to, site-specific mutation and gene synthesis. Other methods of genetic engineering are generally known in the art to one of ordinary skill.

The methods of making polypeptides also include a vector capable of expressing the peptides in an appropriate host. The vector comprises the DNA molecule that codes for the peptides operatively linked to appropriate expression control sequences. Methods of affecting thisoperative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

The nucleic acid molecules described above can be contained within a vector that is capable of directing their expression in, for example, a cell that has been transduced with the vector. Accordingly, in addition to polypeptide mutants, expression vectors containing a nucleic acid molecule encoding a mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a polypeptide mutant are also suitable for use. A cell is a transfected cell, i.e., a cell into which a nucleic acid molecule, for example a nucleic acid molecule encoding a mutant polypeptide, has been introduced by means of recombinant DNA techniques. The progeny of such a cell are also considered suitable for use in the methods disclosed herein.

The precise components of the expression system are not critical. For example, a polypeptide mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., conjugated to a lipid, as described herein.

In some embodiments, the immunogenic composition disclosed herein comprise a vaccine. As will be appreciated by a person of ordinary skill in the art, a metal hydroxide adjuvant particle includes numerous surface hydroxyl groups that are available for ligand exchange. The disclosure contemplates that each metal hydroxide particle in a vaccine formulation is capable of forming multiple surface complex bonds with multiple antigens in accordance with the invention, thus providing highly potent antigenic particles that are effective for potentiating an immune response upon internalization of the particle by an antigen presenting cell, such as, for example, a dendritic cell. A metal hydroxide adjuvant-antigen complex is readily made by providing a metal hydroxide adjuvant and an antigen comprising a hydroxyl-replacement moiety and contacting the adjuvant to the antigen under conditions appropriate for achieving ligand exchange. The metal hydroxide adjuvant-antigen complex can then be advantageously used to prepare a pharmaceutical vaccine. As discussed above, inventive metal hydroxide adjuvant/antigen complexes can be prepared to have a large number of antigens per adjuvant particle. In one embodiment, the metal hydroxide adjuvant antigen complex can have a molar ratio of antigen to metal (of the metal hydroxide adjuvant) of from about 1:1 to about 1:10 or even greater.

In addition, as described in the Examples, antigens complexed with a metal hydroxide adjuvant via a multivalent antigen-adjuvant coupling reagent, are retained at the site of injection and provide higher anti-antigen antibody titers relative to non-complexed antigens or complexed antigens comprising a monovalent antigen-adjuvant coupling reagent. Therefore, it is expected that inventive vaccine formulations can be prepared to effectively potentiate an immune response with fewer antigen molecules and fewer adjuvant particles than vaccines previously known in the art.

To formulate a vaccine, an appropriate amount of metal hydroxide adjuvant-antigen complex can be combined with one or more additional components, such as, for example, diluents and excipients. One example of a diluent that can be included in an inventive vaccine formulation is a pH buffer. An example of a buffer that can be used is a combination of disodium hydrogen phosphate and sodium dihydrogen phosphate. Other examples include potassium salts of these buffers, or a mix of sodium acetate and acetic acid. When a phosphate buffer is used in connection with an inventive vaccine, it is important to recognize and account for the effect that the buffer has on the metal hydroxide adjuvant. In particular, use of a phosphate buffer results in phosphorylation of surface hydroxyl groups of the adjuvant, thereby potentially affecting the ligand exchange adsorption properties of the adjuvant. Thus, in an inventive protocol that includes pretreatment of an adjuvant, it will be appreciated that the pretreatment can be accomplished by placing the adjuvant in a phosphate buffer solution, and that the degree of modification achieved will depend upon the concentration of phosphate in the buffer. On the other hand, in a protocol that does not include pretreatment of an adjuvant, i.e., where maximum ligand exchange functionality, and thus maximum hydroxyl availability, is desired, the adjuvant should not be contacted with a phosphate buffer, or any other composition that will significantly reduce the number of available hydroxyl groups on the surface of the metal hydroxide adjuvant, prior to ligand exchange adsorption. Of course, the use of phosphate buffers after antigen adsorption by ligand exchange has occurred, and even post-treatment of the adjuvant with other phosphate-containing compositions, may be desired in some cases, for example to alter the isoelectric properties of the antigen/metal hydroxide adjuvant complex.

Pharmaceutical Composition and Modes of Administration

In some embodiments, a pharmaceutical composition comprising an immunogenic composition provided by the disclosure is administered. In some embodiments, an pharmaceutical composition comprising an immunogenic composition and a second or additional adjuvants are administered together (simultaneously or sequentially). In some embodiments, a pharmaceutical composition comprising an immunogenic composition and a second or additional adjuvants are administered separately.

In some embodiments, the disclosure provides for a pharmaceutical composition comprising an immunogenic composition with a pharmaceutically acceptable diluent, carrier, solubilizer, emulsifier, preservative and/or adjuvant.

In some embodiments, acceptable formulation materials preferably are nontoxic to recipients at the dosages and concentrations employed. In certain embodiments, the formulation material(s) are for s.c. and/or I.V. administration. In some embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In some embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In some embodiments, the optimal pharmaceutical composition will be determined by one skilled in the art depending upon, for example, the intended route of administration, delivery format and desired dosage. See, for example, Remington's Pharmaceutical Sciences, supra. In some embodiments, such compositions may influence the physical state, stability, rate of in vivo release and rate of in vivo clearance of the immunogenic composition.

In some embodiments, the primary vehicle or carrier in a pharmaceutical composition can be either aqueous or non-aqueous in nature. For example, in some embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In some embodiments, pharmaceutical compositions comprise Tris buffer of about pH 7.0-8.5, or acetate buffer of about pH 4.0-5.5, which can further include sorbitol or a suitable substitute therefore. In some embodiments, a immunogenic composition can be prepared for storage by mixing the selected composition having the desired degree of purity with optional formulation agents (Remington's Pharmaceutical Sciences, supra) in the form of a lyophilized cake or an aqueous solution. Further, in some embodiments, an immunogenic composition can be formulated as a lyophilizate using appropriate excipients such as sucrose.

In some embodiments, the pharmaceutical composition can be selected for parenteral delivery. In some embodiments, the compositions can be selected for inhalation or for delivery through the digestive tract, such as orally. The preparation of such pharmaceutically acceptable compositions is within the ability of one skilled in the art.

In some embodiments, the formulation components are present in concentrations that are acceptable to the site of administration. In some embodiments, buffers are used to maintain the composition at physiological pH or at a slightly lower pH, typically within a pH range of from about 5 to about 8.

In some embodiments, when parenteral administration is contemplated, a therapeutic composition can be in the form of a pyrogen-free, parenterally acceptable aqueous solution comprising an immunogenic composition, in a pharmaceutically acceptable vehicle. In some embodiments, a vehicle for parenteral injection is sterile distilled water in which an immunogenic composition is formulated as a sterile, isotonic solution, properly preserved. In some embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In some embodiments, hyaluronic acid can also be used, and can have the effect of promoting sustained duration in the circulation. In some embodiments, implantable drug delivery devices can be used to introduce the desired molecule.

In some embodiments, a pharmaceutical composition can be formulated for inhalation. In some embodiments, an immunogenic composition can be formulated as a dry powder for inhalation. In some embodiments, an inhalation solution comprising an immunogenic composition can be formulated with a propellant for aerosol delivery. In some embodiments, solutions can be nebulized. Pulmonary administration is further described in PCT application No. PCT/US94/001875, which describes pulmonary delivery of chemically modified proteins.

In some embodiments, it is contemplated that formulations can be administered orally. In some embodiments, an immunogenic composition that is administered in this fashion can be formulated with or without those carriers customarily used in the compounding of solid dosage forms such as tablets and capsules. In some embodiments, a capsule can be designed to release the active portion of the formulation at the point in the gastrointestinal tract when bioavailability is maximized and pre-systemic degradation is minimized. In some embodiments, at least one additional agent can be included to facilitate absorption of the immunogenic composition. In certain embodiments, diluents, flavorings, low melting point waxes, vegetable oils, lubricants, suspending agents, tablet disintegrating agents, and binders can also be employed.

In some embodiments, a pharmaceutical composition can involve an effective quantity of an immunogenic composition in a mixture with non-toxic excipients which are suitable for the manufacture of tablets. In some embodiments, by dissolving the tablets in sterile water, or another appropriate vehicle, solutions can be prepared in unit-dose form. In some embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an immunogenic composition in sustained- or controlled-delivery formulations. In some embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In some embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In some embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In some embodiments, this can be accomplished by filtration through sterile filtration membranes. In certain embodiments, where the composition is lyophilized, sterilization using this method can be conducted either prior to or following lyophilization and reconstitution. In some embodiments, the composition for parenteral administration can be stored in lyophilized form or in a solution. In some embodiments, parenteral compositions generally are placed into a container having a sterile access port, for example, an intravenous solution bag or vial having a stopper pierceable by a hypodermic injection needle.

In some embodiments, once the pharmaceutical composition has been formulated, it can be stored in sterile vials as a solution, suspension, gel, emulsion, solid, or as a dehydrated or lyophilized powder. In some embodiments, such formulations can be stored either in a ready-to-use form or in a form (e.g., lyophilized) that is reconstituted prior to administration.

In some embodiments, kits are provided for producing a single-dose administration unit. In some embodiments, the kit can contain both a first container having a dried protein and a second container having an aqueous formulation. In some embodiments, kits containing single and multi-chambered pre-filled syringes (e.g., liquid syringes and lyosyringes) are included.

In some embodiments, the effective amount of a pharmaceutical composition comprising an immunogenic composition to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an immunogenic composition is being used, the route of administration, and the size (body weight, body surface or organ size) and/or condition (the age and general health) of the patient. In some embodiments, the clinician can titer the dosage and modify the route of administration to obtain the optimal therapeutic effect.

In some embodiments, the frequency of dosing will take into account the pharmacokinetic parameters of the immunogenic composition, in the formulation used. In some embodiments, a clinician will administer the composition until a dosage is reached that achieves the desired effect. In some embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In some embodiments, appropriate dosages can be ascertained through use of appropriate dose-response data.

In some embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intraocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In some embodiments, the composition can be administered locally via implantation of a membrane, sponge or another appropriate material onto which the desired molecule has been absorbed or encapsulated. In some embodiments, where an implantation device is used, the device can be implanted into any suitable tissue or organ, and delivery of the desired molecule can be via diffusion, timed-release bolus, or continuous administration. In some embodiments, it can be desirable to use a pharmaceutical composition comprising an immunogenic composition in an ex vivo manner. In such instances, cells, tissues and/or organs that have been removed from the patient are exposed to a pharmaceutical composition comprising an immunogenic composition, after which the cells, tissues and/or organs are subsequently implanted back into the patient.

In some embodiments, an immunogenic composition can be delivered by implanting certain cells that have been genetically engineered, using methods such as those described herein, to express and secrete the polypeptides. In some embodiments, such cells can be animal or human cells, and can be autologous, heterologous, or xenogeneic. In some embodiments, the cells can be immortalized. In some embodiments, in order to decrease the chance of an immunological response, the cells can be encapsulated to avoid infiltration of surrounding tissues. In some embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Methods of Use

In some aspects, the disclosure contemplates that vaccines can be prepared in accordance with an immunogenic composition provided by the disclosure using any antigen that includes or is modified, engineered, or synthesized to include a reactive group capable of covalent linkage to the antigen-adjuvant coupling reagent.

In some embodiments, the disclosure provides methods for increasing the retention of an antigen in a subject at the site of administration, comprising administering a vaccine comprising an immunogenic composition described herein.

Methods for determining retention of an antigen in a subject are known to those of skill in the art. For example, in some embodiments, the retention of an antigen at the site of administration is evaluated using whole body IVIS scanning after immunization with a labeled antigen. In other embodiments, retention of antigen at the site of administration is verified by immunohistochemical staining or electron microscope studies of injection site tissue samples over time.

In some embodiments, the disclosure provides methods for the continuous release of an antigen to the draining lymph nodes of a subject, comprising administering a vaccine comprising an immunogenic composition described herein. Methods for assessing release of an antigen are known to those of skill in the art. For example, in some embodiments immunohistochemical staining of dLN biopsy collected at various time after immunization determines if an antigen-adjuvant complex is retained at the lymph node and continuously released to stimulate immune responses.

Standard methods of histology of the immune system are described (see, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, Pa.; Louis, et al. (2002) Basic Histology: Text and Atlas, McGraw-Hill, New York, N.Y.).

In some embodiments, the disclosure provides methods for increasing an immune response in a subject, comprising administering a vaccine comprising an immunogenic composition described herein. Upon introduction into a host, the vaccine provokes an immune response. The "immune response" refers to responses that induce, increase, or perpetuate the activation or efficiency of innate or adaptive immunity. The immune response includes, but is not limited to, the production of antibodies and/or cytokines and/or the activation of cytotoxic T cells, antigen presenting cells, helper T cells, dendritic cells and/or other cellular responses.

In some embodiments, the immunogenic compositions are administered as part of prophylactic vaccines or immunogenic compositions which confer resistance in a subject to subsequent exposure to infectious agents, or as part of therapeutic vaccines, which can be used to initiate or enhance a subject's immune response to a pre-existing antigen, such as a viral antigen in a subject infected with a with an infectious agent or neoplasm.

The desired outcome of a prophylactic or therapeutic immune response may vary according to the disease or condition to be treated, car according to principles well known in art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

Methods for analyzing an antibody response in a subject are known to those of skill in the art. For example, in some embodiments an increase in an immune response is measured by ELISA assays to determine antigen-specific antibody titers.

In some embodiments, the disclosure provides methods for increasing broadly neutralizing antibodies in a subject, comprising administering a vaccine comprising an immunogenic composition described herein. Methods for measuring neutralizing antibodies are known to those of ordinary skill in the art. In some embodiments, elicitation of neutralizing antibodies is measured in a neutralization assay.

Methods for identifying and measuring neutralizing antibodies are known to those of skill in the art. For example, in the HIV vaccine field, neutralizing antibodies has the ability to neutralize a majority of the field isolates tested. By majority it is meant that in a representative and diverse collection of field isolates, the antibody is capable of neutralizing at least 50% of the strains, and preferably at least 75% of the strains tested. In this context, "neutralizing" means an effect of reducing the HIV infectivity titre in an in vitro virus infectivity assay as described herein at the antibody concentrations described.

Neutralizing antibodies are an indicator of the protective efficacy of a vaccine, but direct protection from a sub-lethal or lethal challenge of virus unequivocally demonstrates the efficacy of the vaccine. In an exemplary animal model system, a bacterial or virus challenge is conducted wherein the subjects are immunized, optionally more than once, and challenged after immune response to the vaccine has developed. Elicitation of neutralization may be quantified by measurement of morbidity or mortality on the challenged subjects.

In some embodiments, the administration of the immunogenic composition induces an improved B-memory cell response in immunized subjects. An improved B-memory cell response is intended to mean an increased frequency of peripheral blood B lymphocytes capable of differentiation into antibody-secreting plasma cells upon antigen encounter as measured by stimulation of in vitro differentiation. In some embodiments, the disclosure provides methods for increasing the number of antibody secreting B cells. In some embodiments, the antibody secreting B cells are bone marrow plasma cells, or germinal center B cells. In some embodiments, methods for measuring the number of antibody secreting B cells, includes, but are not limited to, an antigen-specific ELISPOT assay and flow cytometric studies of plasma cells, or germinal center B cells collected at various time points post-immunization.

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Cancer and Cancer Immunotherapy

In some embodiments, an immunogenic composition or vaccine, described herein, is useful for treating a disorder associated with abnormal apoptosis or a differentiative process (e.g., cellular proliferative disorders (e.g., hyperproliferaetive disorders) or cellular differentiative disorders, such as cancer). Non-limiting examples of cancers that are amenable to treatment with the methods of the present invention are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising an immunogenic composition or vaccine, can be administered to a patient who has cancer.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The immunogenic composition can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts for an immunogenic composition or vaccine that is sufficient to reduce tumor growth and size, or a therapeutically effective amount, will vary not only on the particular composition or vaccine selected, but also with the route of administration, the nature of the condition being treated, and the age and condition of the patient, and will ultimately be at the discretion of the patient's physician or pharmacist. The length of time during which the compound used in the instant method will be given varies on an individual basis.

In some embodiments, the disclosure provides methods of reducing or decreasing the size of a tumor, or inhibiting a tumor growth in a subject in need thereof, comprising administering to the subject an immunogenic composition or vaccine described herein. In some embodiments, the disclosure provides methods for inducing an anti-tumor response in a subject with cancer, comprising administering to the subject an immunogenic composition or vaccine described herein In some embodiments, the disclosure provides methods for stimulating an immune response, comprising administering an immunogenic composition or vaccine described herein. In some embodiments, the immune response is a humoral immune response. In some embodiments, the immune response is an anti-tumor immune response.

It will be appreciated by those skilled in the art that reference herein to treatment extends to prophylaxis as well as the treatment of the noted cancers and symptoms.

Infectious Diseases

In some embodiments, an immunogenic composition or vaccine disclosed herein is useful for treating acute or chronic infectious diseases. Thus, in some embodiments an immunogenic composition or vaccine is administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. In some embodiments, pharmaceutical formulations including the immunogenic composition are administered topically to treat viral skin diseases such as herpes lesions or shingles, or genital warts. In some embodiments, an immunogenic composition or vaccine is administered to treat systemic viral diseases, including, but not limited to, AIDS, influenza, the common cold, or encephalitis.

In some embodiments, the disclosure provides methods of reducing a viral infection in a subject in need thereof, comprising administering to the subject an immunogenic composition or vaccine described herein. In some embodiments, the disclosure provides methods for inducing an anti-viral response in a subject with cancer, comprising administering to the subject an immunogenic composition or vaccine described herein.

It will be appreciated by those skilled in the art that reference herein to treatment extends to prophylaxis as well as the treatment of the noted infections and symptoms.

Kits

In some embodiments, the disclosure provides a kit comprising an immunogenic composition or vaccine, as disclosed herein, and instructions for use. The kits may comprise, in a suitable container, an immunogenic composition or vaccine, one or more controls, and various buffers, reagents, enzymes and other standard ingredients well known in the art. In some embodiments, the kits further comprise one or more adjuvants. Accordingly, in some embodiments, the immunogenic composition or vaccine and adjuvant are in the same vial. In some embodiments, the immunogenic composition and adjuvant or adjuvants are in separate vials.

The container can include at least one vial, well, test tube, flask, bottle, syringe, or other container means, into which an immunogenic composition or vaccine may be placed, and in some instances, suitably aliquoted. When an additional component is provided, the kit can contain additional containers into which this compound may be placed. The kits can also include a means for containing an immunogenic composition or vaccine, and any other reagent containers in close confinement for commercial sale. Such containers may include injection or blow-molded plastic containers into which the desired vials are retained. Containers and/or kits can include labeling with instructions for use and/or warnings.

In some embodiments, the disclosure provides a kit comprising a container comprising a vaccine comprising an immunogenic composition, an optional pharmaceutically acceptable carrier, and a package insert comprising instructions for administration of the vaccine for treating or delaying progression of cancer in an subject. In some embodiments, the kit further comprises an adjuvant and instructions for administration of the adjuvant for treating or delaying progression of cancer in a subject.

In some embodiments, the disclosure provides a kit comprising a container comprising a vaccine comprising an immunogenic composition, an optional pharmaceutically acceptable carrier, and a package insert comprising instructions for administration of the medicament alone or in combination with an adjuvant and an optional pharmaceutically acceptable carrier, for treating or delaying progression of an infection in a subject.

The present disclosure is further illustrated by the following examples, which should not be construed as further limiting. The contents of all figures and all references, patents and published patent applications cited throughout this application are expressly incorporated herein by reference.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure. Below are examples of specific embodiments for carrying out the present invention. The examples are offered for illustrative purposes only, and are not intended to limit the scope of the present invention in any way.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al, Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Materials and Methods
Antibodies and Reagents

For spleen histology sections, the tissues were stained for B220 (clone RA3-6B2, Biolegend), IgD (11-26c.2a, Biolegend), CD35 (clone 8C12, BD), Ki67 (clone SolA15, ThermoFisher). B220 (clone RA3-6B2, eBioscience), GL7 (Biolegend), CD3 (clone 17A2, Biolegend), and CD38 (clone 90, Biolegend) were used for germinal center staining. For ELISAs, anti-mouse Goat IgG-HRP (Bio-rad) was used. For staining of VRC01gHL B cells in the adoptive transfer model, cells were stained with CCR7 PE (4B12; Biolegend), CD86 BV605 (GL-1; Biolegend), and Streptavidin BV711 (Biolegend). Peptide coupling reagents were purchased from EMD Millipore (Novabiochem) unless otherwise noted. Aluminum hydroxide adjuvant (Al-Hydrogel) and aluminum phosphate (AdjuPhos) adjuvants were purchased from InvivoGen.

Phosphoserine Peptide Synthesis.

Peptides were synthesized manually by solid phase peptide synthesis. A low loading Tentagel Rink Amide resin (Peptides International, 0.2 meq/g) was used for the synthesis of all peptides. Peptide couplings were performed using 4 equivalents of Fmoc-Ser (PO(OBzl)OH)—OH with 3.95 equivalents HATU (Hexafluorophosphate Azabenzotriazole Tetramethyl Uronium) for 2 hr at 25° C. The phosphoserine residues, hereinafter "PS," were deprotected using 5% DBU (1,8-Diazabicyclo[5.4.0]undec-7-ene) in DMF, while all other residues were deprotected in 20% piperidine in DMF. Double couplings were performed for the addition of any PS monomers beyond the third. A 6 unit, Fmoc-protected oligoethylene glycol linker (Peptides International) was added following the addition of the PS monomers to serve as a spacer between the reactive linker and PS residues. For PS-linkers being reacted to proteins, maleoyl-β-alanine (MilliporeSigma) was coupled to the N-terminus of the peptides. Peptides were cleaved in 95% trifluoroacetic acid (TFA), 2.5% H2O, and 2.5% triisopropylsilane (TIPS), for 2.5 hr at 25° C. After precipitation in ice-cold diethyl ether, peptides were dried, resuspended in 0.1 M TEAA buffer (pH 7), and purified by HPLC on a C18 column using 0.1 M TEAA buffer in a gradient of acetonitrile. Peptide masses were confirmed by MALDI-TOF mass spectrometry.

Coupling PS Linkers to Protein Antigens

Antigens were modified with PS-linkers using a thiol-maleimide reaction. In a solution of PBS with 1 mM EDTA, protein antigens at 1 mg/mL were reduced for 15 minutes in 10 equivalents of tris(2-carboxyethyl)phosphpine (TCEP, ThermoFisher), and then TCEP was removed by centrifugal filtration using an Amicon spin filter (10 kDa MWCO). The antigens were then reacted with maleimide-PS conjugates. For coupling to eOD and cytochrome c, the antigen at 1 mg/mL was reacted with 2 molar equivalents of maleimide-PS overnight at 4° C. in PBS. For reaction to SOSIP trimer, 20 molar equivalents of maleimide-PS linker was added to 1 mg/mL SOSIP in PBS to ensure complete reaction to available thiols. Proteins were then separated from unreacted peptide linkers using centrifugal filters (10 kDa MWCO). Reactions were initially monitored using parallel reactions with analogous linkers containing spectroscopic handles (maleimide-dibenzyocyclooctyne linkers), and coupling of the phosphoserines to the antigens was confirmed using a malachite green assay (ThermoFisher). Malachite green assays were quantified using a standard curve derived prepared using known concentrations of the original PS linkers. Labeled proteins were prepared using NHS-AF647 (ThermoFisher) or NHS-IRDye 800CW (LI-COR) by reaction of 6 eq. fluorophore with eOD or SOSIP (1 mg/mL) in 50 mM sodium carbonate buffer for 2 hours, and purified using centrifugal filtration (10 kDa MWCO). Phycoerythrin (PE)-PS conjugates were prepared by reacting NHS-DBCO (Sigma Aldrich) heterobifunctional crosslinker to PE in sodium borate buffer (pH 8.0) at varying molar ratios (2, 4, 8, 16, and 32 equivalents) of linker to protein for 4 hours at room temperature. Unreacted linkers were removed by centrifugal filtration, and then DBCO-modified PE (1 mg/mL) was split into two reactions with 2 molar equivalents of azide-PS4 or azide-Ser3PS1 overnight at 4° C. in PBS. Unreacted PS linkers were then removed by centrifugal filtration.

HIV eOD and SOSIP Antigens

To evaluate PS modification of a vaccine antigen, a HIV envelope gp120 antigen, eOD-GT8, with site-specific introduction of a free N-terminal cysteine residue for peptide tag coupling was produced. eOD-GT8 (or "eOD") is a 21.5 kDa germline-targeting gp120 engineered outer domain antigen designed to initiate priming of human B cells capable of evolving toward an important set of CD4 binding site-specific broadly neutralizing antibodies (bnAbs) known as VRC01-class antibodies. Sok, D. et al., (2016) *Science* 353, 1557-1560; Jardine, J. G. et al. (2015) *Science* 349, 156-161; Jardine, J. et al. (2013) *Science* 340, 711-716. The amino acid sequence of eOD is depicted in SEQ ID NO:1.

```
                                              SEQ ID NO: 1
TGCHHHHHHGGDTITLPCRPAPPPHCSSNITGLILTRQGGYSNDNTVI

FRPSGGDWRDIARCQIAGTVVSTQLFLNGSLAEEEVVIRSEDWRDNAK

SICVQLNTSVEINCTGAGHCNISRAKWNNTLKQIASKLREQYGNKTII

FKPSSGGDPEFVNHSFNCGGEFFYCDSTQLFNSTWFNSTGSAFKVAAW

TLKAAA
```

In addition to the eOD antigen, a stabilized gp140 HIV Env trimer termed SOSIP, was modified with PS linkers at the C-terminus of each protomer. The amino acid sequence of the cysteine-modified SOSIP is shown in SEQ ID NO:2.

```
                                              SEQ ID NO: 2
TGAENLWVTVYYGVPVWKDAETTLFCASDAKAYETEKHNVWATHACVP

TDPNPQEIHLENVTEEFNMWKNNMVEQMHTDIISLWDQSLKPCVKLTP

LCVTLQCTNVTNNITDDMRGELKNCSFNMTTELRDKKQKVYSLFYRLD

VVQINENQGNRSNNSNKEYRLINCNTSAITQACPKVSFEPIPIHYCAP

AGFAILKCKDKKFNGTGPCPSVSTVQCTHGIKPVVSTQLLLNGSLAEE

EVMIRSENITNNAKNILVQFNTPVQINCTRPNNNTRKSIRIGPGQAFY

ATGDIIGDIRQAHCNVSKATWNETLGKVVKQLRKHFGNNTIIRFANSS

GGDLEVTTHSFNCGGEFFYCNTSGLFNSTWISNTSVQGSNSTGSNDSI

TLPCRIKQIINMWQRIGQAMYAPPIQGVIRCVSNITGLILTRDGGSTN

STTETFRPGGGDMRDNWRSELYKYKVVKIEPLGVAPTRCKRRVVGRRR

RRRAVGIGAVFLGFLGAAGSTMGAASMTLTVQARNLLSGIVQQQSNLL

RAPEAQQHLLKLTVWGIKQLQARVLAVERYLRDQQLLGIWGCSGKLIC
```
-continued
```
CTNVPWNSSWSNRNLSEIWDNMTWLQWDKEISNYTQIIYGLLEESQNQ

QEKNEQDLLALDGTKHHHHHHC
```

Vaccine Antigen Synthesis and PS Linker Conjugation eOD gp120 and SOSIP trimer antigens were synthesized as previously described. Jardine, J. et al. (2013) *Science* 340, 711-716; Kulp, D. W. et al. (2017) *Nature communications* 8, 1655. Briefly, eOD with an N-terminal cysteine was expressed in HEK cells, and purified on a Nickel affinity column followed by size exclusion chromatography on a Superdex 75 10/300 column (GE Healthcare). Briefly, trimer genes were synthesized and cloned into pHLsec by Genscript and then co-transfected with human furin on a pcDNA3.1 plasmid at a 2:1 trimer to furin DNA ratio using 293fectin into FreeStyle 293-F cells (ThermoFisher). Trimer supernatant was harvested five days post transfection by centrifugation and purified by affinity chromatography using HisTrap HP columns (GE Healthcare) followed by size-exclusion chromatography (SEC) using a S200 Increase column (GE Healthcare) in PBS at flow rate of 0.5 ml/min. The molecular weight of the trimer was confirmed by SEC multi-angle light-scattering (SECMALS) using DAWN HELEOS II and Optilab T-rEX instruments (Wyatt Technology).

Antigen-Alum Binding and Release

Alum binding experiments were performed using either fluorescently labeled proteins or by ELISA. A weight ratio of 10:1 alum:protein was used for all binding experiments and immunizations, unless otherwise noted. For binding assays, protein antigen was first incubated with Al-Hydrogel for 30 minutes in PBS at 25° C. to allow binding, then mouse serum was added for a final concentration of 10% (v/v). Protein, alum, and serum mixtures were incubated for 24 hours at 37° C., and solutions were centrifuged at 10K×g for 10 minutes to pellet alum. The concentration of unbound protein in the supernatant was then measured by fluorescence or ELISA. Fluorescence measurements were performed using a Tecan Infinite M200 Pro absorbance/fluorescence plate reader. The fluorescence intensity was normalized to the total fluorescence of a sample that underwent the same processing but lacked alum. For ELISA measurements, 96-well Nunc MaxiSorp plates (ThermoFisher) were coated with VRC01 antibody, blocked with 1% BSA, and serial dilutions of antigen were added to the plate with a maximum concentration of 2 μg/mL. Antigen was then detected using anti-His tag HRP (1:5000 dilution), washed, and developed with TMB substrate. The amount of antigen was then quantified by comparing absorbance values to control antigen with known concentrations.

B Cell Interactions with Alum-Antigen Conjugates.

In vitro experiments were performed using gl-VRC01 expressing Ramos B cells, kindly provided by Prof. Daniel Lingwood (Ragon Institute of MGH, MIT, and Harvard). Calcium flux measurements were performed using cells loaded with 10 uM Flou-4 dye (ThermoFisher) for 30 minutes at 37° C. in serum-free RPMI in the presence of calcium. B cells were washed once, and heated to 37° C. prior to activation. Antigen and alum were suspended in complete RPMI containing with 10% FBS prior to the addition to B cells. Baseline fluorescence was measured for 1 minute prior to the addition to the addition of antigen at a concentration of 1 μg/mL eOD. Alum was added to the B cells at 10 μg/mL. Fluo-4 fluorescence emission was normalized to baseline values prior to the addition of the antigen. For confocal and TEM imaging experiments, Ramos B cells expressing gl-VRC01 were incubated with eOD/alum formulations for 1 hour in RPMI media containing 10% FBS at 37° C. For confocal imaging, cells were then fixed in PBS 1% paraformaldehyde for 15 min, washed, stained with DAPI and phalloidin, mounted on a glass slide, and imaged using an inverted Olympus X71 microscope. Samples for TEM analysis were fixed in 0.1 M sodium cacodylate buffer (pH 7.0) with 3% paraformaldehyde, 2% glutamate, 5% sucrose, pelleted, and post fixed in 1% $OsO_4$ in veronal-acetate buffer. The cells were stained en block overnight with 0.5% uranyl acetate in veronal-acetate buffer (pH 6.0), then dehydrated and embedded in Embed-812 resin. Sections were cut on a Leica EM UC7 ultra microtome with a Diatome diamond knife at a thickness setting of 50 nm, stained with 2% uranyl acetate, and lead citrate. The sections were examined using a FEI Tecnai spirit at 80 KV and photographed with an AMT ccd camera.

For adoptive transfer experiments, B cells were purified using anti-mouse CD43 (Ly-48) MACS® MicroBeads (Miltenyi Biotec) from the spleen of homozygous VRC01gHL BCR knock-in mice per the manufacturer's protocol. In some experiments, purified B cells were subsequently labeled with 5 μM Cell-trace Violet (Thermo Fisher) in 0.1% BSA-DPBS for 9.5 minutes at 37° C. 106 eOD-specific B cells were retro-orbitally injected into recipient mice 1-3 days before immunization.

Animals and Immunizations.

Experiments and handling of mice were conducted under federal, state, and local guidelines under an IACUC approved protocol. Six to eight week old female BALB/c mice were purchased from the Jackson Laboratory. For imaging experiments, 10 μg eOD labeled with AF647 was injected with 100 μg alum in 100 μL PBS subcutaneously into the shaven tail base. Immunogenicity experiments with eOD and SOSIP used immunization formulations of 5 μg antigen mixed with 50 μg alum in 100 μL PBS, unless otherwise noted. In some formulations, saponin-containing nanoparticles were injected at a concentration of 10 μg/mL cholesterol. Unless otherwise noted, immune responses are measured after a single primary immunization. Sera were collected by retro-orbital bleeding every other week for ELISA measurements.

Whole Mouse Imaging and Lymph Node Trafficking.

Signals of antigens labeled with AF647 were measured using an IVIS fluorescence imaging system over time at the injection site. Total radiance was normalized to the initial IVIS signal at day 0, measured 30 minutes after injection. Antigen accumulation in lymph nodes was measured using a LI-COR Odyssey fluorescence imager. For these experiments, alum (50 μg) was labeled by addition of a mixture of 0.5 nmol PS4-680 and 5 μg IR800 dye-labeled eOD. The alum/eOD samples were mixed for 30 min at 25° C., and then injected s.c. into groups of BALB/c mice. Inguinal lymph nodes were excised at various time points, and whole-tissue fluorescence was measured by the LICOR imaging system at 700 nm and 800 nm wavelengths. Values represent the integrated fluorescence intensity. For histology experiments, mice were immunized by subcutaneous or intraperitoneal injections with 10 μg AF647-labeled antigen labeled and 100 μg alum.

ELISAs Analysis of Antibody Titers.

For ELISAs to measure anti-eOD titers, Nunc MaxiSorp plates were directly coated with unmodified, monomeric eOD (1 μg/mL) and blocked with PBS containing 1% BSA. For SOSIP ELISAs, plates were coated with an ST-II antibody (2 μg/mL), and SOSIP containing an ST-II tag was then added to the plates after blocking with 1% BSA in PBS. Responses against SOSIP gp120 were measured by coating ELISA plates with a rabbit anti-His tag antibody (Genscript), followed by blocking, and then addition of histagged SOSIP gp120 antigen (2 μg/mL). Serial dilutions of sera were added to the blocked plates for 2 hours at 25° C., washed in PBS with 0.05% Tween-20, and incubated with anti-mouse IgG-HRP (BioRad). ELISA plates were then developed with TMB substrate and absorbance values at 450 nm were measured. Base-blocking ELISAs were performed using plates coated with human VRC01 (2 μg/mL), followed by a blocking step with 1% BSA in PBS and then the addition of SOSIP (2 μg/mL) for 2 hr at 25° C. To obscure the base of trimer, 20 μg/mL base-binding antibody was added for 30 minutes before the addition of serum dilutions. Serum dilutions were added directly to the wells with the base-binding antibody still remaining, and absorbance values were compared to wells that were incubated with 1% BSA in PBS instead of the base-binding antibody. His-tag specific antibodies were measured using plates coated in streptavidin (2 μg/mL) followed by addition of biotin-H6 peptide (Genscript). Titers were determined at an absorbance cutoff of 0.1 OD and 0.3 OD for SOSIP and eOD immunizations, respectively.

Saponin Adjuvant Synthesis

An ISCOM-like nanoparticle comprised of self-assembled cholesterol, phospholipid, and Quillaja (Quil-A) saponin was prepared for some immunizations as previously described.[45] All synthesis was performed under sterile conditions with sterile reagents. Briefly, 10 mg each of cholesterol (Avanti Polar Lipids 700000) and DPPC (Avanti Polar Lipids 850355) were dissolved separately in 20% MEGA-10 (Sigma D6277) detergent at a final concentration of 20 mg/ml and 50 mg Quil-A saponin (InvivoGen vac-quil) was dissolved in MQ H2O at a final concentration of 100 mg/ml. Next, DPPC solution was added to cholesterol followed by addition of Quil-A saponin in rapid succession and the volume was brought up with PBS for a final concentration of 1 mg/ml cholesterol and 2% MEGA-10. The solution was allowed to equilibrate at 25° C. overnight, followed by 5 days of dialysis against PBS using a 10 k MWCO membrane. The adjuvant solution was then filter sterilized using a 0.2 μm Supor syringe filter, concentrated using 50 k MWCO centricon filters, and further purified by FPLC using a Sephacryl S-500 HR size exclusion column. Each adjuvant batch was finally characterized by negative stain TEM and DLS to confirm uniform morphology and size and validated for low endotoxin by Limulus Amebocyte Lystae assay (Lonza QCL-1000). Final adjuvant concentration was determined by cholesterol quantification (Sigma MAK043).

ELISPOT and Germinal Center Analysis.

Bone marrow ELISPOTs were performed 3 months after immunization according to manufacturer's instructions unless otherwise noted (MabTech). ELISPOT plates were coated with an anti-mouse IgG antibody, and isolated bone marrow cells were added to the plate for 4 hr at 37° C. in complete RPMI (500 k or 100 k cells per well for antigen-specific or total IgG responses, respectively). After washing the plates, antigen-specific responses were measured by the addition of biotinylated antigen (1 μg/mL) for 2 hr at 25° C., followed by streptavidin-HRP. Bone marrow cells isolated from each mouse were measured in triplicate. For measurement of germinal center responses, mice were sacrificed 9 days after immunization and lymph nodes were mechanically digested and passed through a 70-um filter. Cells were then stained with antibodies against CD3e, B220, CD38, and GL-7, as well as an AF647-labeled eOD 60mer nanoparticle, Jardine, J. et al. (2013) *Science* 340, 711-716. To identify eOD-specific B cells. Flow cytometric analysis was performed using a BD Canto.

Immunohistochemistry of Injection Sites, Lymph Nodes, and Spleens.

Mice were immunized by subcutaneous or intraperitoneal injections with 10 µg AF647-labeled antigen and 100 µg alum. Histology sections were prepared using skin from the injection site, spleen, or lymph node tissues that were fixed with 4% paraformaldehyde overnight, washed, and embedded in a 3 wt % low melting point agarose at 37° C. then allowed to cool and solidify on ice for 15 mins. 100-200 um sections were prepared using a Vibratome (Leica VT1000S) and suspended in ice cold PBS then transferred into a blocking solution containing 10% goat serum, 0.2% Triton-X100 and 0.05% sodium azide overnight at 37° C. prior to immunostaining. For the injection site sections, slices were stained in a solution of morin (1 uM) in 0.5% acetic acid in ethanol. For lymph node and spleen sections, the tissues were stained for B220 (clone RA3-6B2, Biolegend), IgD (11-26c.2a, Biolegend), CD35 (clone 8C12, BD), Ki67 (clone SolA15, ThermoFisher) and PS4-Cy3 (1:200 dilution, 1 uM). Antibodies were used at 1:100 dilution in blocking buffer overnight at 37° C., followed by washes with PBS 0.05% Tween and mounted on a glass slide with ProLong Diamond antifade mounting medium (Life Technologies). Images were then acquired using Leica SP8 laser scanning confocal microscope with a 10× or 25× water objective. Images were then processed with Fiji software.

ICP-MS of Aluminum in Lymph Nodes.

Inductively coupled plasma mass spectrometry (ICP-MS) measurements were performed using immunizations of 200 µg of alum mixed with eOD or PS4-eOD. Inguinal lymph nodes were excised at indicated timepoints, dissolved in nitric acid, digested at 200° C. for 20 min in a Milestone UltraWave microwave digestion system, diluted into water to 2% nitric acid, and analyzed by an Agilent 7900 ICP-MS. A standard curve of aluminum from 1 µg/ml to 1 ng/mL was used to quantify the samples, along with an internal standard of rhodium for every sample.

Antigenicity of Trimer Bound to Alum.

Antigenicity of SOSIP trimer bound to alum was measured using a modified sandwich ELISA protocol. An irrelevant protein (cytochrome-c from *Saccharomyces cerevisiae*, Sigma Aldrich) modified with a PS4 linker was first coated on ELISA plates overnight. Alum at 100 µg/mL was then added to the plates to bind to the exposed PS residues present on cytochrome-c. Control wells were coated with mouse VRC01 at 2 µg/mL. Plates were washed with PBS containing 0.05% Tween-20, and then incubated with solutions of 1% BSA containing SOSIP-PS (1 µg/mL) for 2 hr at 25° C. Broadly neutralizing antibodies or base-specific antibodies were added at 100 ng/mL, and detected with a secondary Ab-HRP conjugate, followed by development in TMB substrate.

Example 1: Adsorption of Protein Antigens to Alum Via a Multivalent Antigen-Adjuvant Coupling Reagent Short peptide/polymer linkers that would mediate binding to alum by ligand exchange between phosphate groups and hydroxyls at the surface of alum particles were designed. Peptides comprised of 1-12 consecutive phosphoserines (PS) followed by a short poly(ethylene glycol) spacer and N-terminal maleimide functional group were prepared by solid phase synthesis.

FIG. 1A shows the chemical structure of maleimide-phosphoserine coupling reagents comprising phosphoserine linkers and a schematic of a protein antigen comprising a solvent-exposed, free sulfhydryl group (—SH). FIG. 1B shows the chemical structure of the maleimide-phosphoserine coupling reagent, wherein the maleimide moiety is covalently linked to a thiol group comprising a protein antigen via a thioether linkage. The final coupling reagent-antigen conjugate was mixed with alum in buffered saline, whereby the antigen was coupled or adsorbed to alum via ligand exchange between the phosphate groups comprising the phosphoserines and surface hydroxyl groups present on the surface of alum. FIG. 1C generally depicts the binding and orientation of the coupling reagent-antigen conjugate when coupled or adsorbed to alum.

To evaluate the adsorption of protein antigens conjugated with monovalent vs. multivalent coupling reagents to alum, the adsorption of a model protein (yeast cytochrome c) to alum was determined. FIG. 1D shows the adsorption of cytochrome c onto alum as a function of protein concentration. Cytochrome c proteins were functionalized with coupling reagents that varied the number (n) of phosphoserine residues by reacting the maleimide on the coupling reagents to a solvent-exposed cysteine on the protein. The extent of functionalization of cytochrome c was equivalent for all coupling reagents (data not shown). The amount of protein bound to alum was determined by removing the alum and bound protein via centrifugation, and measuring the unbound protein in the supernatant. The amount of bound protein was then assumed to be the total amount of protein subtracted from the amount unbound protein. As shown in FIG. 1D, cytochrome binding to the alum adjuvant increases with increasing number of phosphoserine residues. These data demonstrate that proteins conjugated to multivalent coupling reagents comprising two or four phosphoserines bound alum to a greater extent that a monovalent coupling reagent comprising one phosphoserine.

Figure 2B:
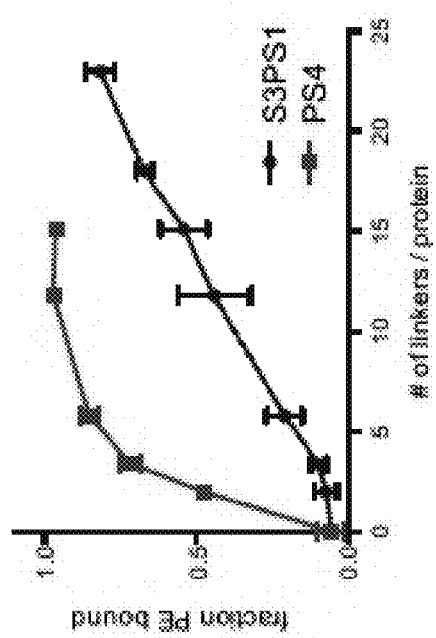
FIG. 2B provides a line graph depicting fluorescence spectroscopy of protein bound to alum. Peptides linkers were coupled to DBCO-modified phycoerythrin (PE) via copper-free click chemistry at a range of total linkers per protein. PS/Ser-conjugated PE (5 µg/mL) was mixed with alhydrogel (50 µg/mL) for 30 min, followed by addition of medium containing 10% mouse serum for 24 hr. Protein bound to alum after this incubation was assessed by fluorescence spectroscopy. (n=3 samples/group).

In vivo, PS-anchored proteins could be displaced from the alum surface by serum proteins or organic phosphate ions present in interstitial fluid. To evaluate the role of PS valency in achieving stable binding, 240 KDa fluorescent protein phycoerythrin (PE) were modified with 2-20 linkers, each of which contained either one or four PS residues, FIG. 2A. Imaging experiments using a dye-PS4 conjugate were prepared by a Cu-free click reaction between azide-PS4 and an DBCO-fluorophore, followed by HPLC purification. The azide-PS4 and azide-Ser3-PS1 peptides were prepared using the same methods described above for the phosphoserine portion of the peptide. An oligoethylene glycol linker was not included for these linkers. At the N-terminus of the peptide, Fmoc-5-azido-pentanoic acid (Anaspec) was used in place of the maleoyl-β-alanine, and the peptide was deprotected in 20% piperidine prior to cleavage in TFA. PS1- or PS4-modified PE was mixed with alum for 30 minutes to allow binding, followed by 24 hours of incubation in buffer containing 10% serum, and protein bound to alum after this two-step process was measured by fluorescence spectroscopy. As shown in FIG. 2B, unmodified PE showed almost no retention on alum, but PS linkers promoted a majority of the protein to be alum-bound, and only 2-4 PS4 linkers per protein were required to achieve the same level of binding as 10-20 linkers that had a single PS residue. Thus even for very large proteins, modification with a few multivalent PS linkers promotes stable binding to alum in the presence of serum.

Figure 3:
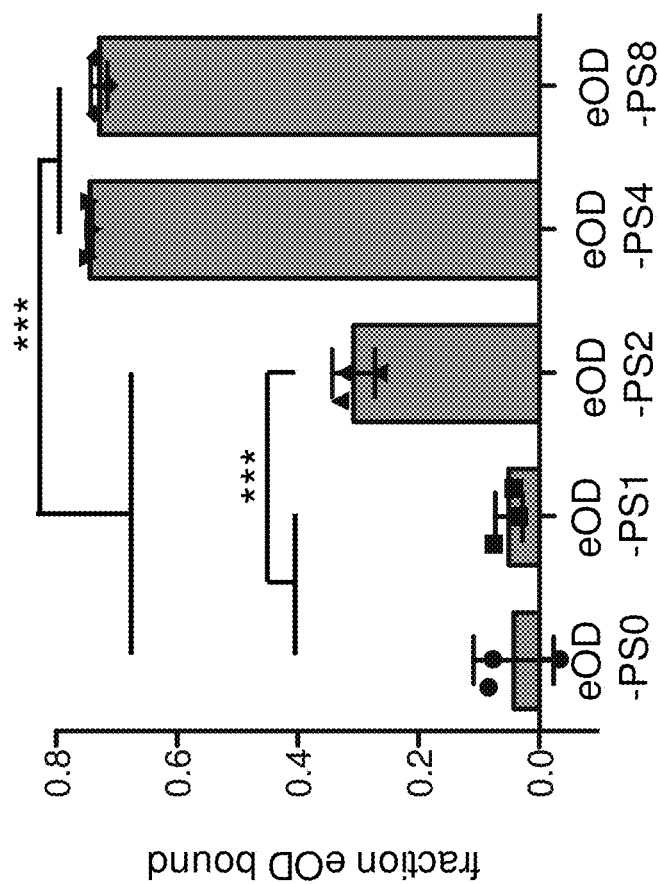
FIG. 3 provides a bar graph showing fluorescence spectroscopy to measure protein remaining bound to alum after unmodified or PS-conjugated fluorescent eOD protein (10 µg/mL) was mixed with alhydrogel (100 µg/mL) for 30 min, then incubated in PBS containing 10% mouse serum for 24 hr.

In the next experiment, eOD antigens were coupled with a single peptide linker containing 1-8 phosphoserines, or control linkers containing serine residues, and binding to alum was evaluated. In buffer, 90% of added eOD adsorbed to alum within 30 min irrespective of the peptide linker composition (data not shown). However, when alum with adsorbed eOD was incubated for 24 hours in 10% serum, only ~2% of unmodified or control serine-modified eOD remained bound, while PS-modified antigen showed increasing retention on alum with increasing PS valency, plateauing at ~75% retention for 4 or more phosphoserines in the affinity linker, FIG. 3. Thus, immunogen binding to alum could be readily tuned through the introduction of multivalent PS linkers.

Figure 4:
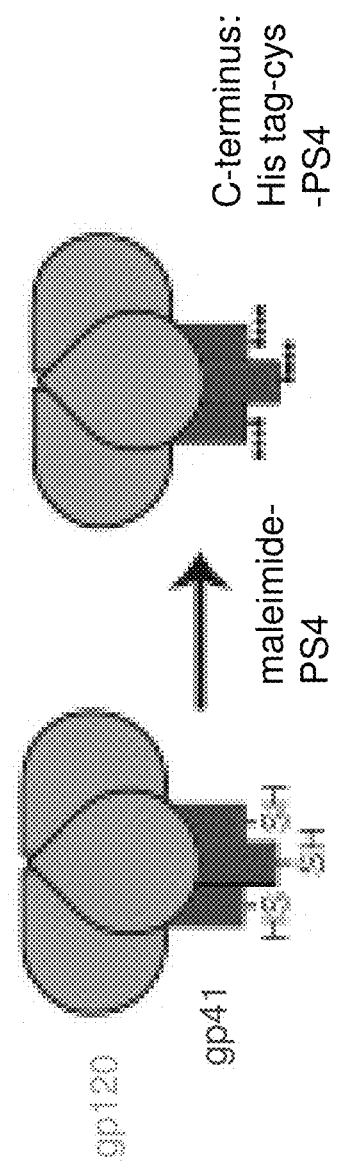
FIG. 4 provides a schematic depicting the SOSIP trimer conjugated at the base with a multivalent coupling reagent comprising phosphoserines.
Figure 5:
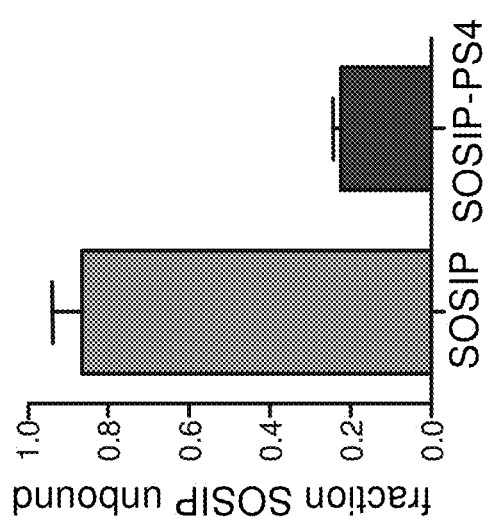
FIG. 5 provides a bar graph showing the fraction of SOSIP antigen released from alum in the presence of serum after 24 hours as determined by ELISA.

Another HIV antigen, SOSIP, was modified with a free cysteine at the C-terminal end of each protomer, to which three PS linkers could be conjugated at the base of each trimer, as illustrated in FIG. 4. Covalent binding of coupling reagents to engineered HIV antigens eOD and SOSIP was performed. FIG. 5 shows the fraction of SOSIP released from alum in the presence of 10% serum after 24 hours. Protein concentrations were measured by ELISA relative to a protein standard of a known concentration. These data demonstrate that, after exposure to serum, protein antigens coupled to alum via multivalent coupling agents are retained on alum to a greater extent than protein antigens alone or protein antigens coupled to alum via a monovalent coupling reagent.

Example 2: Antigen-Specific B Cells Engulf Alum/PS-Antigen Nanoparticles and Exhibit Enhanced Activation In Vitro Alum is not a monolithic solid but is made up of fibrous aggregates of aluminum hydroxide nanocrystals. Harris, J. R. et al. (2012) *Micron* 43, 192-200. In the setting of tight binding between the immunogen and alum particles, antigen delivery to lymph nodes over time could either be mediated by slow release of free antigen from alum surfaces at the site of injection, or antigen could be trafficked to lymph nodes still bound to aluminum hydroxide nanocrystals or nanocrystal aggregates, as shown in FIG. 6A. If the latter scenario were prevalent, this would have multiple implications for the immune response because (1) B cells are strongly triggered by multivalent particulate antigens, (2) alum particles might exert direct adjuvant activity on antigen-specific B cells, and (3) presentation of antigen from the particle surfaces could impact the epitope specificity of the humoral response.

In vitro impact of stimulating antigen-specific B cells with alum/PS-eOD conjugates vs. alum/eOD was first assessed. Human Ramos B cells expressing germline-inferred VRC01 IgM (glVRC01), representative of the B cells that are the desired targets of the eOD immunogen in humans, were stimulated in cell culture by eOD alone, eOD mixed with alum, or PS-eOD mixed with alum. Calcium signaling in the B cells was traced by the fluorescent reporter dye, Fluo-4. Consistent with prior reports that eOD must be multimerized for strong signaling through glVRC01 receptors[22], free monomeric eOD elicited a near-baseline response, as did eOD mixed with alum, as shown in FIG. 6B. By contrast, B cells stimulated by alum/PS-eOD showed steadily increasing calcium signaling with increasing phosphoserine valency, FIG. 6B. By confocal microscopy, B cells incubated for 1 hour with alum and eOD were observed to have bound alum particles but showed little or no eOD uptake, FIG. 6C. However, when the B cells were incubated with alum/PS8-eOD, alum particles were taken up with colocalized eOD, FIG. 6D. Higher resolution visualization of these cells by TEM imaging revealed that nanoscale alum aggregates were internalized by B cells when PS-eOD was bound to alum, as shown in FIG. 6E. These results suggest that when bound to alum via PS linkages, eOD can behave as a multivalent, particulate vaccine that is internalized by B cells.

Example 3: Antigens Coupled to Alum Via Multivalent Antigen-Adjuvant Coupling Reagents are Retained at Site of Administration and Enhance Anti-Antigen IgG Titers PS-mediated binding to alum slows antigen clearance in vivo. Alum is retained at injection sites for many weeks, Flarend, R. E. et al. (1997) *Vaccine* 15, 1314-1318, but clearance of antigens administered with alum is often much faster. Gupta, R. K., et al., (1996) *Vaccine* 14, 1412-1416; Noe, S. M., et al., (2010) *Vaccine* 28, 3588-3594.

Figures 7A, 7B:
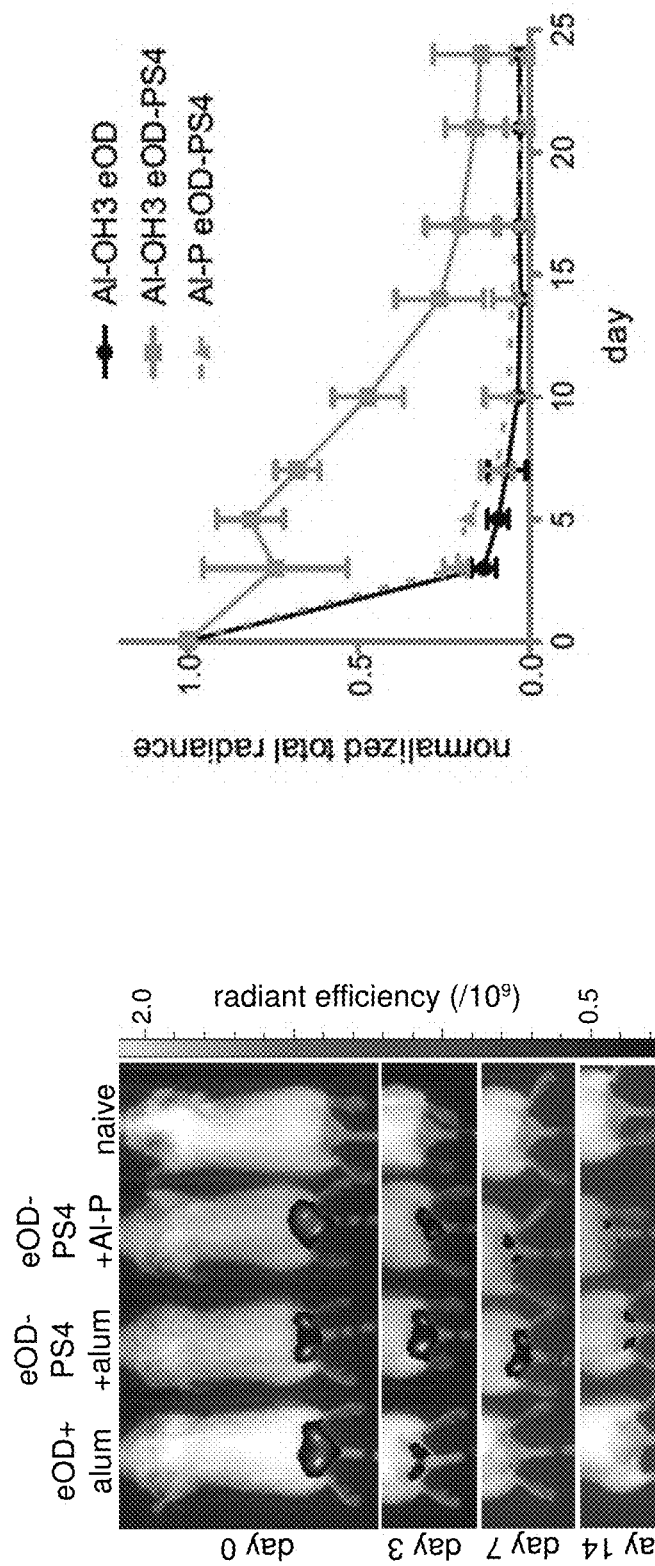
FIG. 7A provides a false-color image of mice following injection with fluorescently-labeled eOD antigens absorbed to adjuvant as determined by IVIS. Fluorophore-labeled eOD or PS4-eOD (10 µg protein) was mixed with either alhydrogel (alum, 100 µg) or aluminum phosphate adjuvant (alumP, 100 µg), and injected subcutaneously in BALB/c mice (n=4 animals/group) followed by longitudinal whole-animal IVIS imaging of fluorescence at the injection sites.
FIG. 7B provides a line graph showing the fluorescent signal from the mice followed for 24 days following injection of fluorescently-labeled eOD antigens absorbed to adjuvant, either alum (Al—OH3) or aluminum phosphate (Al—P), as determined by IVIS and expressed as normalized total radiance.

To test the effect of the coupling reagents in vivo, mice were administered AlexaFluor 647-labeled eOD antigen incubated with alum in the presence and absence of a multivalent coupling reagent comprising 4 phosphoserines (hereafter "PS4"). As a control, the eOD antigen and PS4 were incubated with Adju-Phos, an alternative aluminium-based adjuvant that does not bind to PS4. The fluorescent antigen-adjuvant formulations were injected subcutaneously at the tail base of BALB/c mice and monitored using an in vivo imaging system (IVIS). FIG. 7A shows a false-color IVIS image of mice that were injected with (1) Al-Hydrogel (alum; Al—OH3) with eOD conjugated with AlexaFluor 647, (2) Al-Hydrogel with eOD-PS4 conjugated with AlexaFluor 647, (3) Adju-Phos (Al—P) with eOD-PS4 conjugated with AlexaFluor 647, and (4) not injected, respectively, on day 0 (day of injection) and after day 3. The fluorescent signal from the mice was followed for 24 days following injection and the normalized fluorescent signal determined by IVIS as a function of time is shown in FIG. 7B.

Figure 8C:
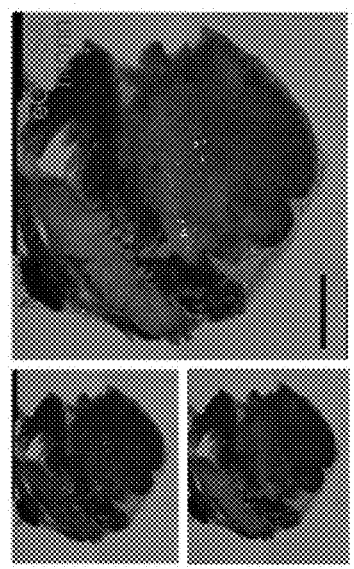
FIG. 8C provides a representative histology section from BALB/c mice injected with eOD/alum as in FIG. 7A. Shown are representative injection site cross sections from animals receiving eOD. Morin in purple, eOD-AF647 in cyan, and bright field in grey (scale bar: 1 mm).
Figure 8B:
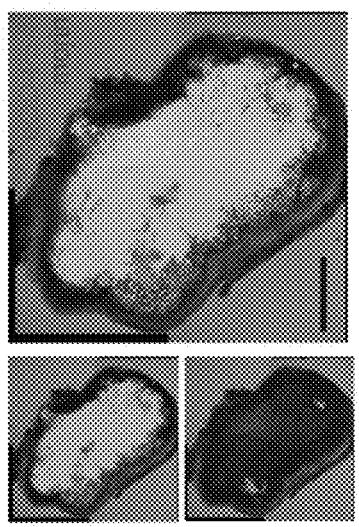
FIG. 8B provides a representative histology section from BALB/c mice (n=3 animals/group) injected with PS4-eOD/alum as in FIG. 7A. Mice were sacrificed 8 days after injection and immunization sites were analyzed by histology with morin staining to detect alum. Shown are representative injection site cross sections from animals receiving PS4-eOD. Morin in purple, eOD-AF647 in cyan, and bright field in grey (scale bar: 1 mm).
Figure 8A:
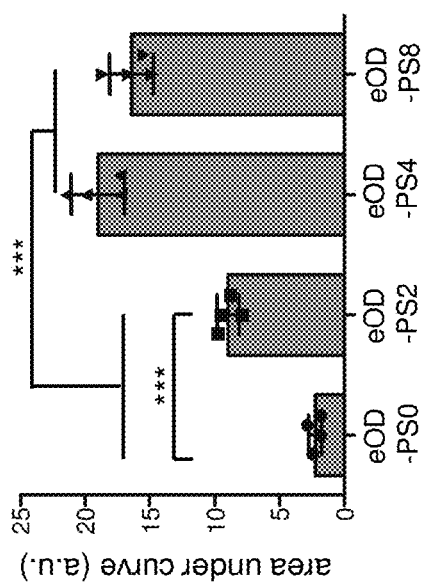
FIG. 8A provides a bar graph showing total fluorescence area under the curve measured over 25 days. Fluorophore-labeled eOD proteins conjugated with linkers containing 2-8 PS residues were mixed with alhydrogel and injected in BALB/c mice followed by IVIS imaging of injection sites over time as in FIG. 7A (n=4 animals/group). ***, p<0.001 by one-way ANOVA followed by Tukey's post test.

Unmodified eOD cleared from the injection site within 3 days, while PS4-eOD persisted for over 3 weeks; antigen signal decayed with a half life of ~9 days, FIG. 7B. As an additional control, PS4-eOD mixed with aluminum phosphate (alumP), an alternate clinical formulation of alum that is unable to undergo ligand exchange binding with the PS linker was injected. PS4-eOD cleared at the same rate as eOD in this case FIG. 7A, 7B. Varying PS linker valency, maximum antigen persistence was observed with four or more PS residues, as shown in FIG. 8A. Histology of alum nodules at the injection sites at day 8 post injection stained using morin dye to label alum, De Boni, U., et al., (1974) *Histochemistry* 40, 31-37, showed PS8-eOD colocalized with alum as shown in FIG. 8B, while unmodified eOD was undetectable FIG. 8C.

These results demonstrate that PS-antigens are cleared in vivo much more slowly than unmodified antigens adsorbed to alum. eOD-PS4 antigens coupled to alum are retained at the site of administration to a greater extent than eOD-PS4 antigens administered in combination with Adju-Phos (Al—P) or eOD antigens administered in combination with alum (Al—OH3). These results indicates that prolonged exposure of draining lymph nodes to the eOD-PS4 antigen via prolonged retention would enhance an immune response against the eOD antigen.

Figure 9A:
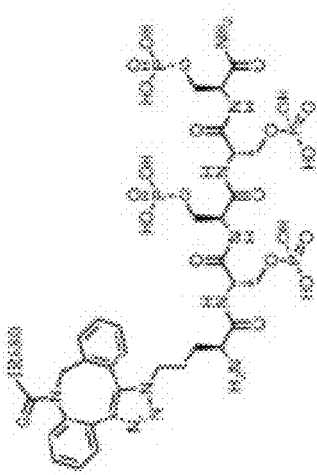
FIG. 9A provides the structure of IR680-PS4 conjugate, synthesized by Cu-free click chemistry.
Figure 9B:
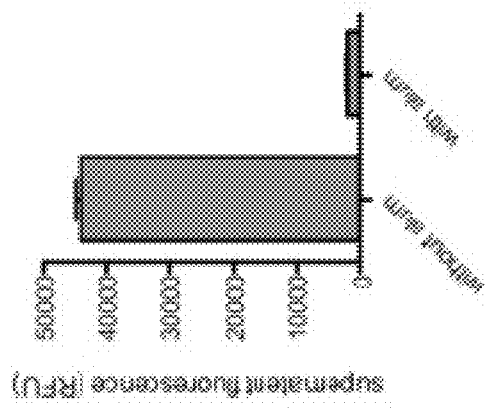
FIG. 9B shows a bar graph of supernatant fluorescence after IR680-PS4 conjugate was incubated either alone or with alum for 30 minutes, and then 10% mouse serum was added, and the solution was incubated at 37° C. for 72 hours. Data represents the fluorescence measurements of the supernatant after centrifugation to remove any dye remaining bound to alum. Other dyes (Cy3-DBCO and AlexaFluor488-DBCO) were conjugated in the same manner.
Figures 10A, 10B, 10C:
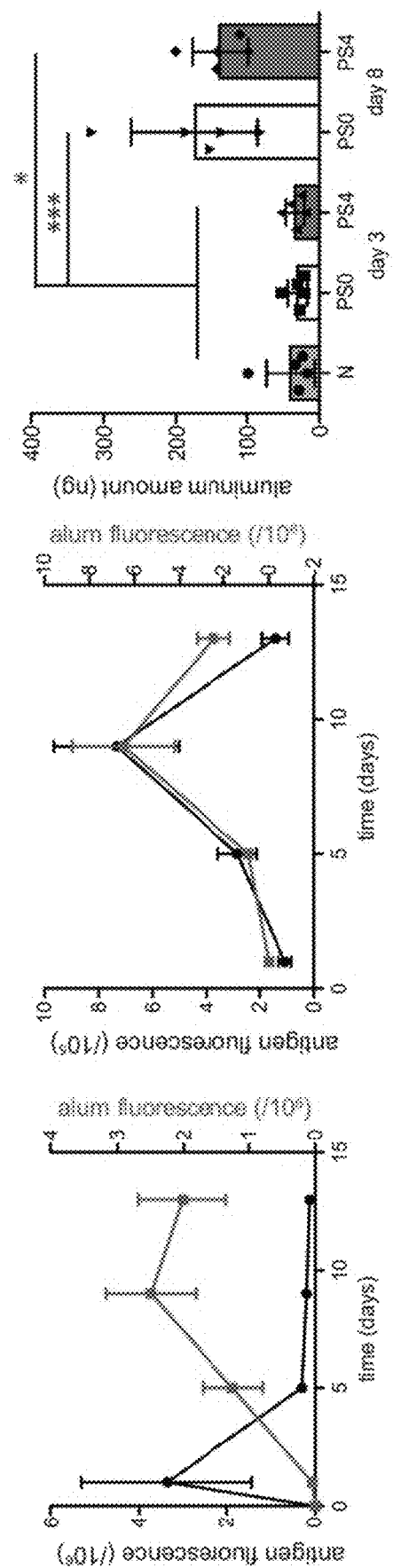
FIG. 10A provides a line graph showing total fluorescence measured in excised dLNs at serial time points. Groups of BALB/c mice (n=5/group) were immunized with 5 μg IR800 dye-labeled Ser4-eOD mixed with 50 μg IR680-labeled alum.
FIG. 10B provides a line graph showing total fluorescence measured in excised dLNs at serial time points. Groups of BALB/c mice (n=5/group) were immunized with 5 μg IR800 dye-labeled PS8-eOD mixed with 50 μg IR680-labeled alum.
FIG. 10C provides a bar graph reflecting ICP-MS measurements of aluminum in inguinal lymph nodes of naïve mice and mice that were immunized subcutaneously. Measurements were taken from lymph nodes collected at days 3 and 8 post-immunization.

Example 4: Alum and PS-Antigens Traffic Together In Vivo and Accumulates in Draining LNs In the next experiment, the in vivo progress of antigen-adjuvant complex post-administration was next assessed. An infrared dye (IR680)-PS4 conjugate as shown in FIG. 9A, was synthesized to simultaneously track antigen and alum. IR680-PS4 bound very tightly to alum, with minimal detectable dye released from alum following 72 hr incubation in serum, as shown in FIG. 9B. Alum was mixed with an equimolar amount of PS8-eOD (labeled with IR800 dye) and IR680-PS4, or dye-labeled Ser4-eOD and IR680-PS4 as a control. Total accumulation of each tracer in draining lymph nodes (dLNs) was measured by IR imaging of whole lymph nodes excised from animals at serial time points. Ser4-eOD levels in the LN peaked at 24 and rapidly decayed thereafter, while alum tracer slowly accumulated, FIG. 10A. By contrast, PS8-eOD and alum showed a matching pattern of slow accumulation in dLN, as shown in FIG. 10B. To confirm that alum particles were in fact trafficking to dLNs, aluminum levels in dLNs were directly quantified by inductively coupled plasma-mass spectrometry (ICP-MS). As shown in FIG. 10C, aluminum was readily detected in dLNs for both alum/PS8-eOD and alum/Ser4-eOD immunizations.

Example 5: Antigen-Specific B Cells Acquire PS-Antigen Bound to Alum Particles In Vivo In the next experiment, an in vivo adoptive transfer model which enables the tracking of eOD-specific B cells was employed to detect how alum particles functionalized with PS-antigens deliver antigen to B cells in the multivalent form. Abbott, R. K. et al. (2018) *Immunity* 48, 133-146. Mouse B cells expressing glVRC01 BCRs (VRC10$^{gHL}$) were adoptively transferred into wild-type mice to establish a defined antigen-specific B cell precursor frequency, Id., followed by intraperitoneal vaccination with eOD/alum combinations, FIG. 11A. The VRC10$^{gHL}$ cells expressed GFP and were labeled with CellTrace Violet (CTV). When mice were injected with labeled Ser-eOD or PS-eOD and alum, VRC01gHL B cells in both groups acquired antigen 1 day after immunization, but eOD uptake continued to rise in the PS-eOD/alum group at day 2, as shown in FIGS. 11B, 11C. When both the eOD and alum were fluorescently labeled (alum labeled with AF488-PS4), VRC01$^{gHL}$ B cells showed simultaneous uptake of the phosphoserine-linked antigen and alum on day 2, contrasting with low levels of either eOD or alum taken up by the antigen-specific cells in Ser-eOD/alum-immunized mice, FIGS. 11D to 11F.

Histology of sectioned spleens two days after intraperitoneal immunization with dye-labeled alum and eOD showed colocalization of alum and PS8-eOD around B cell follicles, but in the control group only alum and little or no Ser4-eOD was observed, FIGS. 12A, 12B. Antigen-specific B cells in animals immunized with alum/Ser-eOD showed no upregulation of activation marker CD86 nor signs of cell division, while robust activation and division of VRC01$^{gHL}$ cells was observed in the alum/PS8-eOD-immunized group, as shown in FIGS. 12C and 12D. As eOD has been engineered to bind with high affinity to VRC10$^{gHL}$ cells, Jardine, J. et al. (2013) *Science* 340, 711-716, this experiment was repeated by immunizing adoptively transferred mice with PS- or Ser-modified eOD-GT5, an alternate form of the eOD immunogen having a physiological (KD ~0.5 μM) affinity for the VRC01$^{gHL}$ BCR. The results were qualitatively similar (data not shown).

Figures 13A, 13B:
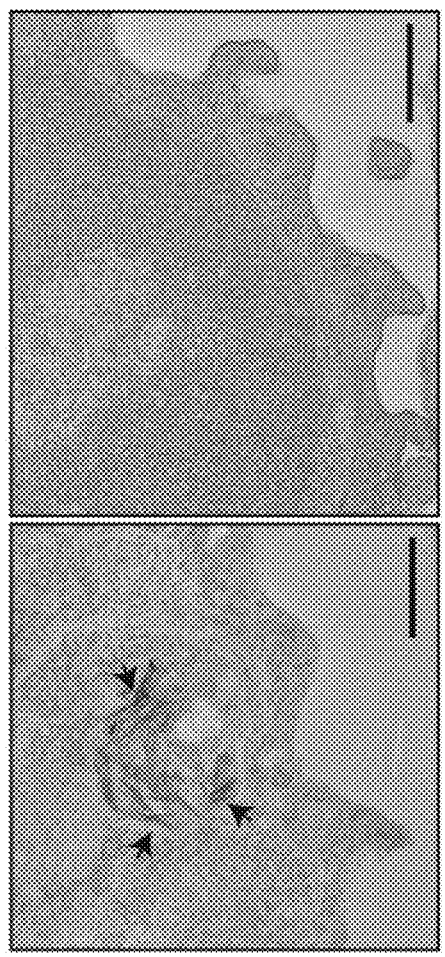
FIG. 13A provides TEM sections of splenic B cells on day 2 following intraperitoneal immunization with 10 μg AF$^{647}$-labelled PS8-eOD-GT8 with alum. GFP⁺ AF$^{647+}$ VRC01$^{gHL}$ B cells were sorted from the spleen, fixed, stained, and sectioned for TEM imaging. (Scale bars 200 nm). State number of experiments and cells analyzed.
FIG. 13B provides TEM sections of splenic B cells on day 2 following intraperitoneal immunization with 10 μg AF$^{647}$-labelled PS8-eOD-GT8 with alum. GFP⁻ AF$^{647-}$ endogenous B cells sorted from the spleen, fixed, stained, and sectioned for TEM imaging. (Scale bars 200 nm).

To determine if the antigen-specific B cells were taking up antigen bound to alum particles, animals were immunized with alum mixed with fluorescent PS-eOD. On Day 2 after immunization, spleens were harvested. Splenic cell suspensions were obtained and sorted for eOD+ antigen-specific B cells or control endogenous B cells, then fixed and sectioned for TEM imaging. As shown in FIGS. 13A and 13B, VRC01$^{gHL}$ B cells that had acquired antigen in vivo had readily detectable accumulations of alum particle aggregates in endosomal compartments (53% of 120 cell sections counted), while endogenous B cells showed no alum uptake (0% of 43 cell sections counted). These results demonstrate that by engineering tight binding to alum, PS-modified antigens are delivered in alum-bound form to B cells in vivo.

Figures 14A, 14B:
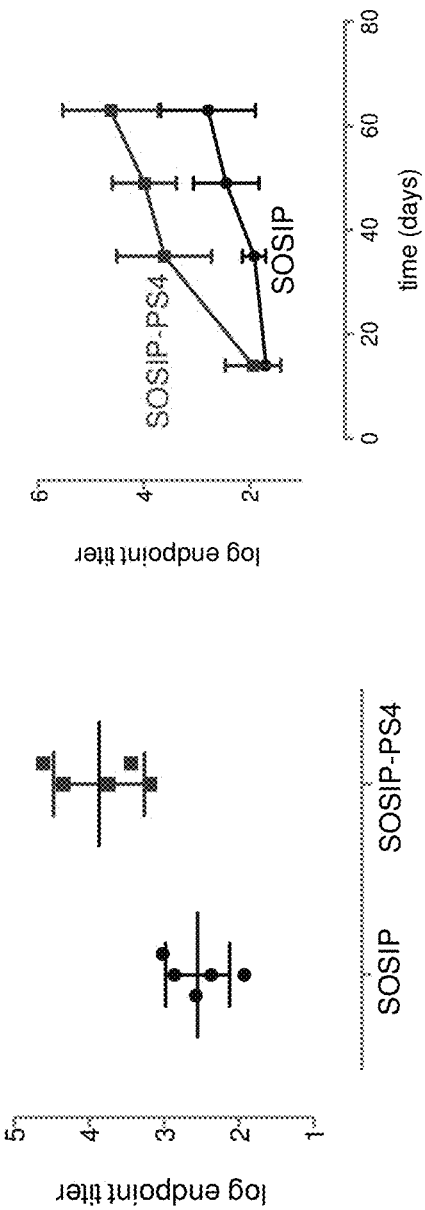
FIG. 14A provides a graph showing anti-SOSIP antibody titers in mice 63 days following primary injection on day 0 and secondary injection on day 21 with alum absorbed with SOSIP antigens alone or conjugated with coupling reagents comprising four phosphoserines (SOSIP-PS4) as determined by ELISA.
FIG. 14B provides a line graph showing anti-SOSIP antibody titers in mice following injections on day 0 and day 21 with alum absorbed with SOSIP antigens alone or conjugated with coupling reagents comprising four phosphoserines (SOSIP-PS4) over time as determined by ELISA.

Example 6: Antigens Coupled to Alum Via Multivalent Antigen-Adjuvant Coupling Reagents and Co-Administered with Additional Adjuvant are Retained at Site of Administration and Enhance Anti-Antigen IgG Titer To further characterize the relationship between the retention of antigen-adjuvant complexes comprising multivalent coupling reagents and antibody response, mice were administered 2 μg SOSIP in combination with 50 μg alum or 2 μg SOSIP-PS4 coupled to 50 μg alum on days 0 and day 21. FIG. 4 shows a schematic of the SOSIP trimer conjugated with a multivalent coupling reagent comprising phosphoserines. As shown in FIG. 14A, a significant increase in anti-SOSIP antibody titer was observed 63 days post-prime. Further, as shown in FIG. 14B, this increase in anti-SOSIP antibody titer persisted over time. Taken together, these data demonstrate that retention of antigens coupled to alum via multivalent coupling reagents induce a significantly enhanced humoral immune response relative to uncoupled antigens administered in combination with alum.

Figure 15A:
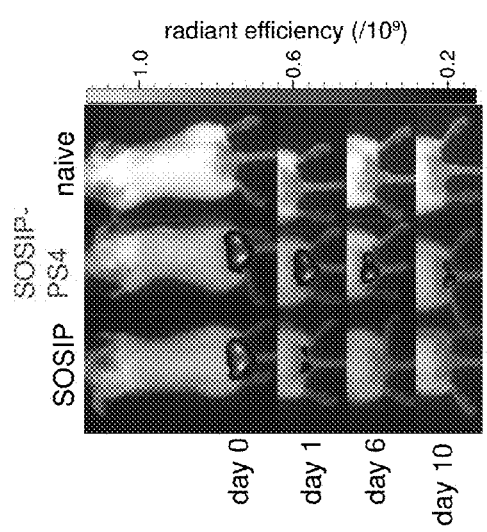
FIG. 15A provides a false-color image of mice following injection with fluorescently-labeled SOSIP antigens absorbed to adjuvant (alum) in combination with an additional adjuvant (ISCOMATRIX®) as determined by IVIS.
Figure 15C:
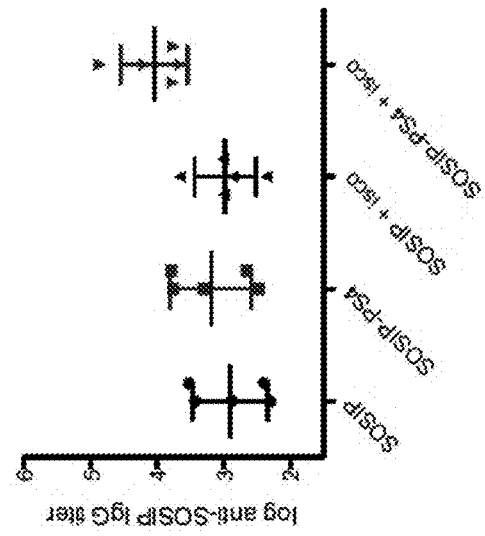
FIG. 15C provides a graph showing anti-SOSIP antibody titers in mice 56 days following a single primary injection with alum absorbed with SOSIP antigens alone or conjugated with coupling reagents comprising four phosphoserines (SOSIP-PS4) or in combination with an additional adjuvant (ISCOMATRIX®), as indicated, over time, as determined by ELISA.
Figure 15B:
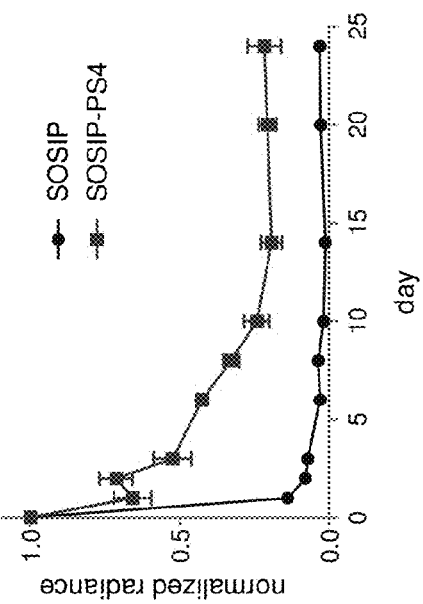
FIG. 15B provides a line graph showing the fluorescent signal from the mice followed for 25 days following injection of fluorescently-labeled SOSIP antigens absorbed to adjuvant as determined by IVIS and expressed as normalized total radiance.

To determine if the administration site retention and enhancement of anti-antigen IgG titers by alum-coupled antigens could be further enhanced by co-administration of an additional adjuvant, mice were immunized with 50 μg of al-hydrogel (alum), 5 μg of ISCOMATRIX® (an additional adjuvant), and 5 μg of either fluorescently-labeled SOSIP or fluorescently-labeled SOSIP-PS4 in the subcutaneous tissue of the tail base. SOSIP was labeled with the fluorophore AlexaFluor 647. FIG. 15A shows a false-color IVIS image of mice that were injected with a combination of ISCOMATRIX®, Al-Hydrogel (alum; Al—OH3), and SOSIP conjugated with AlexaFluor 647 (SOSIP), a combination of ISCOMATRIX®, Al-Hydrogel (alum; Al—OH3), and SOSIP-PS4 conjugated with AlexaFluor 647 (SOSIP-PS4), or not injected (naive), as indicated, on day 0 (day of injection) and after day 1, day 6 and day 10. The fluorescent signal from the mice was followed for 20 days following injection and the normalized fluorescent signal determined by IVIS as a function of time is shown in FIG. 15B. These data demonstrate that SOSIP-PS4 antigens coupled to alum and co-administered with ISCOMATRIX® are retained at the site of administration to a greater extent than SOSIP antigens administered in combination with alum and ISCOMATRIX®. In agreement with the results shown in FIGS. 14A-14B, these results indicates that prolonged exposure to the SOSIP-PS4 antigen via increased retention would enhance an immune response against the SOSIP-PS4 antigen. Quantification of fluorescence at injection site of mice show extended retention of SOSIP containing the phosphoserine linker.

To further characterize the relationship between the retention of antigen-adjuvant complexes comprising multivalent coupling reagents and antibody response, mice were administered 5 μg SOSIP in combination with 50 μg alum or 5 μg SOSIP-PS4 coupled to 50 μg alum. As indicated in FIG. 15C, mice labeled "+isco" also received 5 μg iscomatrix, an additional adjuvant that improves the immune response. In contrast to the administration of antigen described in FIGS. 14A and 14B, mice received a single immunization. The prolonged retention of alum-coupled SOSIP-PS4 antigen combined with the improved immune response from the additional adjuvant showed significantly enhanced anti-SOSIP IgG titers, as shown in FIG. 15C (SOSIP-P4+isco). This immunization combination of alum, ISCOMATRIX®, and an alum-binding antigen also potentially eliminates the need for a secondary immunization (boost).

Figure 16:
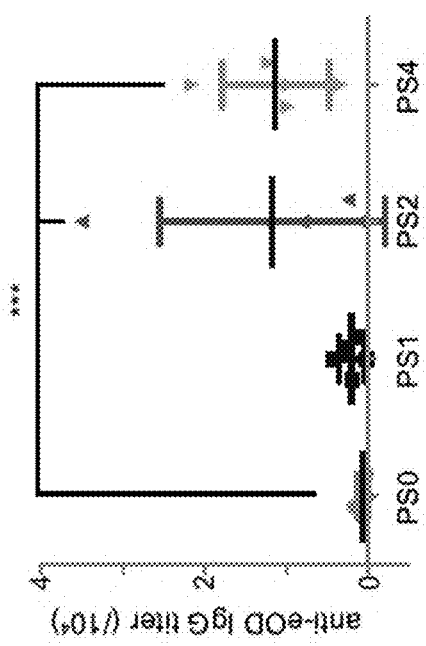
FIG. 16 provides a graph showing anti-eOD antibody titers in mice 4 weeks following injection with alum (Al—OH3) coupled to eOD antigens conjugated with coupling reagents comprising no phosphoserines (eOD-PS0), one phosphoserine (OD-PS1), two phosphoserines (eOD-PS2), and four phosphoserines (eOD-PS4) as determined by ELISA.
Figure 17:
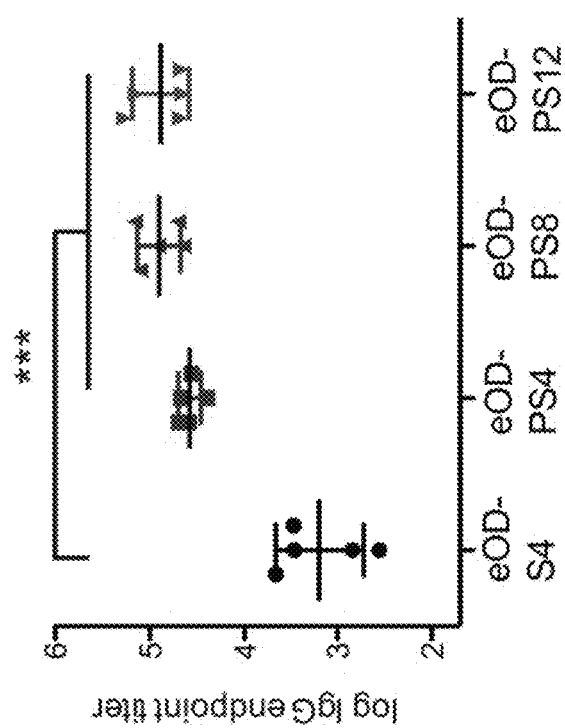
FIG. 17 provides a dot plot of serum IgG titers from BALB/c mice (n=5/group) that were immunized with 50 μg alum mixed with 5 μg eOD (with or without PS modification); serum IgG titers were analyzed by ELISA at 6 weeks.

Example 7: Alum/PS-eOD Immunization Enhances Multiple Facets of the Humoral Immune Response To determine if antigen retention at the site of administration correlates with an enhanced humoral immune response, the anti-eOD antibody titer in mice injected with 50 µg alum coupled to eOD antigens (2 µg) that were either unconjugated (eOD-PS0) or conjugated with coupling reagents comprising one phosphoserine (OD-PS1), two phosphoserines (eOD-PS2), and four phosphoserines (eOD-PS4) antigens, was determined 4 weeks following injection of the antigens. As shown in FIG. 16, the anti-eOD antibody titer increased significantly in mice administered alum-coupled eOD-PS2 or eOD-PS4 relative to alum-coupled eOD-PS0 and eOD-PS1. These results confirms that there is a correlation between antigen retention and antibody response.

Figure 18E:
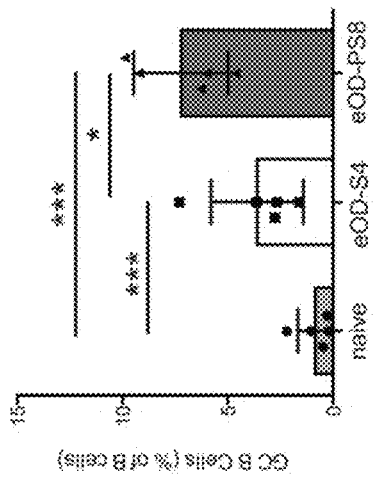
FIG. 18E provides a bar graph of mean GC B cell frequencies.

The impact of PS-antigen immunization on the immune response was characterized in FIGS. 17 and 18A-18G. Immunization of BALB/c mice with alum/Ser4-eOD or alum/PS-eOD revealed a clear trend of increasing serum IgG titers as the number of phosphoserines in the affinity linker increased; PS4-eOD elicited 63-fold higher serum IgG titers compared to the Ser4-eOD antigen FIG. 17. The next experiment tested whether the response to alum/PS-antigen could be further amplified by co-administration of the antigen and alum together with an ISCOM-like saponin nanoparticle adjuvant that very potently promotes humoral immunity in mice, non-human primates, and humans, Pauthner, M. et al. (2017) *Immunity* 46, 1073-1088; Drane, D. et al., (2007) *Expert Rev Vaccines* 6, 761-772. Saponin nanoparticles did not interfere with PS-antigen binding to alum (data not shown). Co-immunization with saponin and alum adjuvants in combination elicited durable IgG responses approximately 10-fold greater than alum alone FIG. 18A vs. FIG. 17. PS8 linkers increased titers only modestly over PS4 linkers, as shown in FIG. 18A and phosphoserine-antigen immunization was effective whether vaccines were administered subcutaneously or intramuscularly, as shown in FIG. 18B. Importantly, measurable antibody response to the phosphoserine linker itself was not detected (not shown). Consistent with the stable high levels of serum antibody detected over time, ELISPOT analysis of bone marrow plasma cells 3 months after a single alum/PS-antigen immunization showed 16-fold more antigen-specific plasma cells elicited by immunization with PS4-eOD immunization compared to control Ser4-eOD, FIG. 18C.

Figure 18F:
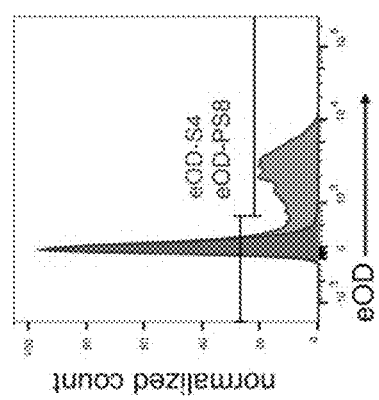
FIG. 18F provides a representative histograms of GC B cells that bind $AF^{647-}$ labeled eOD.
Figure 18G:
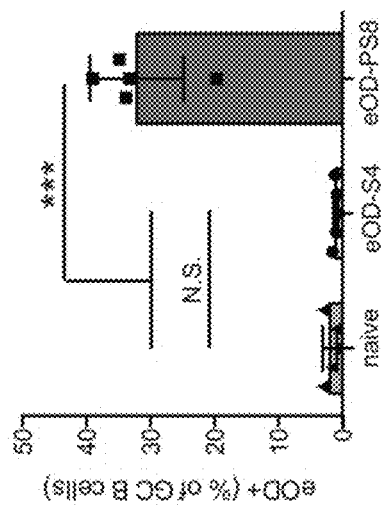
FIG. 18G provides bar graph reflecting the frequencies of GC B cells that bind $AF^{647}$-labeled eOD. , $p<0.01$; *, $p<0.001$ by one-way ANOVA followed by Tukey's post test.

Affinity maturation of the humoral response occurs in germinal centers, where B cells cyclically mutate their immunoglobulin genes to evolve higher affinity binders; strategies to promote germinal center (GC) responses are thus of great interest for HIV vaccines, Havenar-Daughton, et al. (2017) *Immunol Rev* 275, 49-61. While GC B cells were barely detectable above background following alum/Ser-eOD immunization, alum/PS-eOD primed a robust germinal center response, FIGS. 18D, 18E. Further, the percentage of eOD-binding GC B cells increased drastically from ~2% to ~45% in response to PS-antigen immunization, as shown in FIGS. 18F, 18G. Overall, these results indicate that vaccination with immunogens engineered for tight alum binding promotes both early and late events in the humoral immune response.

Example 8: Alum/PS-SOSIP Immunization Enhances Humoral Responses to Env Trimers

Figure 19A:
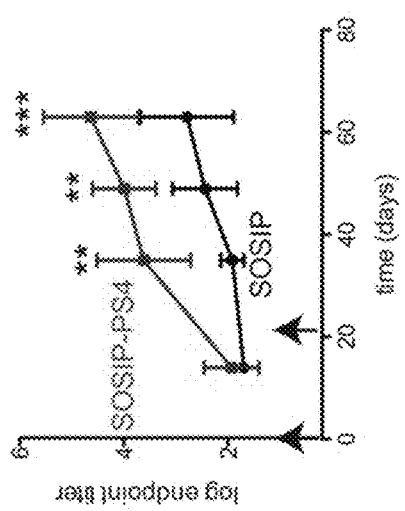
FIG. 19A provides serum IgG titers collected over time from BALB/c mice (n=5/group) that were immunized with 5 µg SOSIP (with or without PS modification) mixed with 50 µg alum at days 0 and 21. **$p<0.01$, *$p<0.05$ by two-way ANOVA followed by Bonferroni's post test.
Figure 19B:
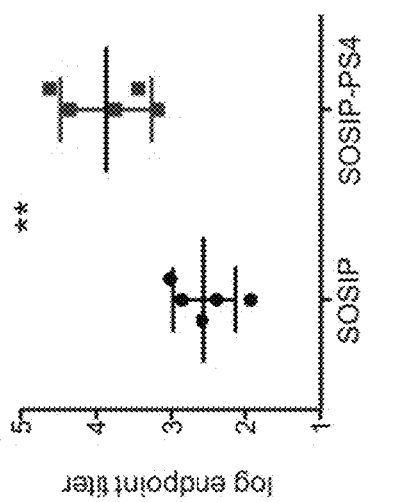
FIG. 19B provides day 63 titers from individual mice that were immunized as described in FIG. 19A. *, $p<0.05$; , $p<0.01$; *, $p<0.001$ by Student's t-test.
Figure 19C:
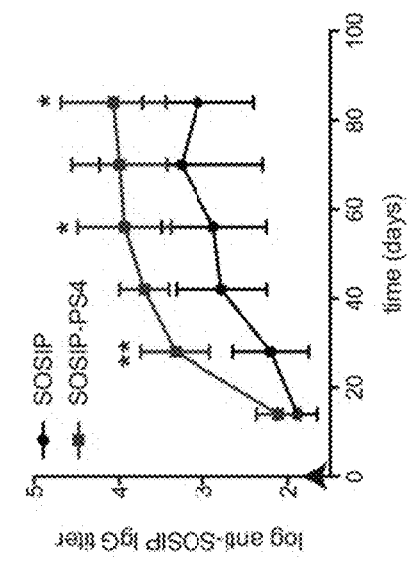
FIG. 19C provides serum IgG titers collected over time from BALB/c mice (n=10/group, pooled from two independent immunizations) that were immunized with 5 µg SOSIP or SOSIP-PS4 mixed with 50 µg alum and 5 µg saponin adjuvant. **$p<0.01$, *$p<0.05$ by two-way ANOVA followed by Bonferroni's post test.
Figure 19D:
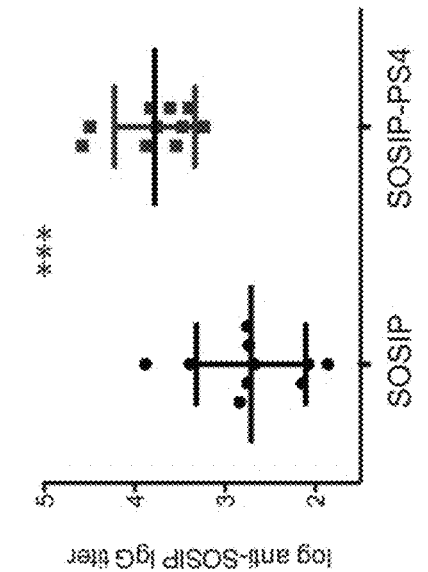
FIG. 19D provides week 6 titers from individual mice immunized as described in FIG. 19C. *, $p<0.05$; , $p<0.01$; *, $p<0.001$ by Student's t-test.
Figure 19E:
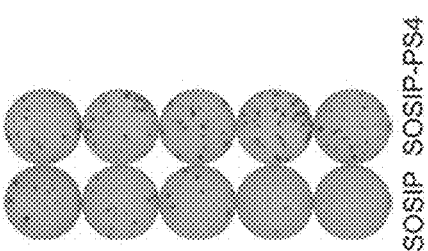
FIG. 19E provides exemplary ELISPOT wells from bone marrow ELISPOT analysis of antibody-secreting cells at 3 months from individual mice immunized as described in FIG. 19C.
Figure 19F:
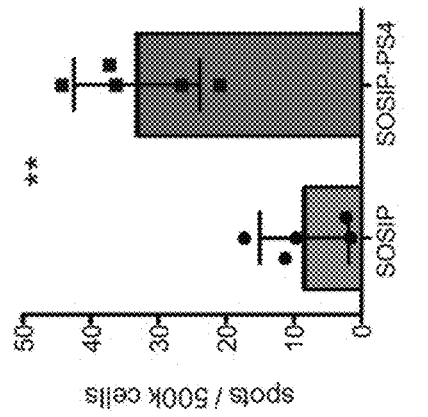
FIG. 19F provides individual and mean trimer-specific, IgG-producing cells from each immunization group. *, $p<0.05$; , $p<0.01$; *, $p<0.001$ by Student's t-test.

The impact of PS-mediated alum binding on overall humoral responses to SOSIP envelope trimers were evaluated. A prime and single boost of mice with SOSIP trimer mixed with alum elicited a weak trimer-specific IgG response, but SOSIP-PS4 administered in the same regimen led to ~20-fold higher titers by 7 days post-boost, as shown in FIGS. 19A, 19B. Co-administration of alum together with saponin adjuvant allows SOSIP trimers to prime measurable IgG responses following a single immunization, but alum/saponin vaccination with SOSIP-PS4 elicited substantially higher trimer-specific titers that were maintained over time, as shown in FIGS. 19C, 19D. Similar to the findings with eOD antigens, a significant increase in bone marrow plasma cells secreting trimer-specific IgG antibodies 3 months after immunization was were observed as shown in FIGS. 19E, 19F.

Example 9: Oriented, Site-Specific Immobilization Blocks the Base of Alum-Bound PS-Env Trimers and Enables Epitope Masking The discovery that PS modification promotes delivery of antigens to B cells still bound to alum particles opens up an additional strategy for shaping the B cell response, whereby undesirable epitopes are masked by immobilizing the antigen with undesired sites oriented in apposition to the alum particle surface. In animal models of HIV infection, antibody responses to the base of HIV trimer base are immunodominant but are irrelevant for neutralization of the virus, Havenar-Daughton, et al. (2017) *Immunol Rev* 275, 49-61. In an effort to minimize antibody responses against the trimer base, SOSIP was modified with a free cysteine at the C-terminal end of each protomer, to which three PS linkers could be conjugated at the base of each trimer, as illustrated in FIG. 4.

SOSIP-PS trimers showed increased retention on alum following serum exposure compared to unmodified SOSIP, as shown in FIG. 5B.

Figure 20B:
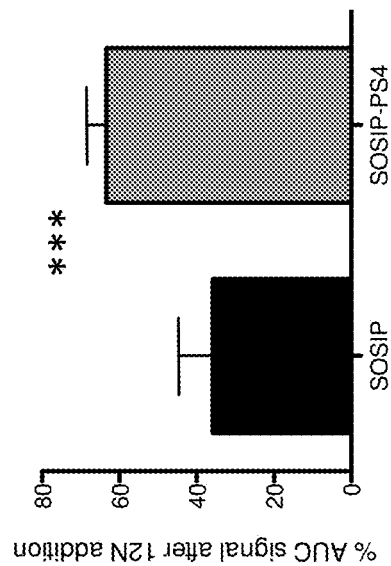
FIG. 20B provides a bar graph describing the percentage of ELISA signal remaining after addition of 12N antibody. Percentage of ELISA signal represents the ratio of the area under the curve (AUC) from the ELISA signal in FIG. 19A with 12N antibody to the AUC in the absence of 12N (*** signifies $p<0.001$).
Figure 20A:
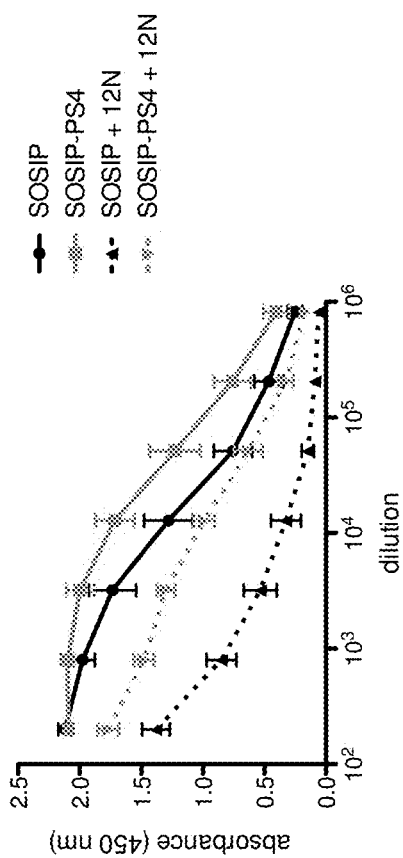
FIG. 20A provides a line graph showing absorbance values from an ELISA curve of SOSIP-specific IgG antibodies from immunized mouse sera in the presence and absence of SOSIP base-binding antibody, 12N. ELISA plates coated with SOSIP were incubated with 12N antibody prior to the addition of sera from immunized mice with dilutions as indicated on the x-axis. Sera were taken from mice on day 72 that received immunizations on day 0 and day 28 of alum, ISCOMATRIX®, and either SOSIP antigen alone or conjugated with coupling reagents comprising four phosphoserines (SOSIP-PS4).

To further characterize which portion of the protein antigen was bound by antibodies from immunized sera, a competition ELISA was performed using high affinity antibodies that bound to known locations on the protein antigen. A base-specific antibody, 12N, was used to obscure the base region of SOSIP and block serum antibodies from binding that portion of SOSIP. Sera were taken from mice on day 72 following primary (day 0) and secondary (day 28) immunizations, which consisted of 2 µg SOSIP in combination with 50 µg alum or 2 µg SOSIP-PS4 coupled to 50 µg alum. The absorbance values showed a decrease in ELISA signal measured in the presence of the competing base-specific antibody 12N for both types of immunization, as shown in FIG. 20A. However, the relative decrease in signal, as measured by the area under the curve of the ELISA, was significantly less for SOSIP-PS4 coupled to alum, as shown in FIG. 20B.

SOSIP and SOSIP-PS were recognized equivalently by both bNAbs and non-neutralizing base-specific mAbs when the free trimers were captured on ELISA plates, FIG. 21A groups 1 and 2. However, when base-modified SOSIP-PS was bound to alum coated on ELISA plates, non-neutralizing antibodies against the base of the trimer showed minimal binding, while bNAbs that recognize a variety of neutralizing sites on the trimer surface still bound, as shown in FIG. 21A.

Similar to the results obtained with eOD, IVIS imaging following administration of fluorescent SOSIP with alum revealed rapid clearance of unmodified SOSIP but slow decay of PS4-SOSIP from immunization sites, as shown in FIGS. 15A, 15B. Following immunization, ELISA analysis was carried out by assessing IgG binding to plate-bound SOSIP in the presence or absence of base-binding mAbs. Sera from mice immunized with alum/SOSIP showed a modest SOSIP-specific IgG response, and the binding was largely blocked by addition of a base-specific monoclonal antibody, FIG. 21B. By contrast, IgG responses in mice immunized with alum/SOSIP-PS4 were stronger and were only weakly reduced by addition of base-specific Ab, as shown in FIGS. 21B, 21C. Furthermore, alum/SOSIP-p54 immunization led to a significant decrease in responses to the His tag located at the base of the trimer when animals were immunized with SOSIP-PS4 and an increased response to the gp120 portion of the trimer, FIGS. 21D, 21E.

These data demonstrate that the site-specific coupling of SOSIP to alum directs immune attention away from the base and towards other portions of the protein when compared to the uncoupled SOSIP antigen. This controlled masking of portions of the antigen is the result of the site-specific conjugation of the antigen directly to the alum surface. These results thus suggest that directed orientation of immunogens with the PS-linker can alter the specificity of the immune response.

EQUIVALENTS

Those skilled in the art will recognize or be able to ascertain, using no more than routine experimentation, many equivalents of the specific embodiments described herein described herein. Such equivalents are intended to be encompassed by the following claims.

What is claimed is:

1. An antigen-adjuvant complex comprising:
   (a) an antigen covalently linked to an antigen-reactive moiety that is coupled, to a multivalent adjuvant-reactive moiety comprising two or more hydroxyl-replacement groups; and
   (b) a metal hydroxide adjuvant,
   wherein the antigen is conjugated to the metal hydroxide adjuvant via the hydroxyl replacement groups of the multivalent adjuvant-reactive moiety, thereby forming an antigen-adjuvant complex.

2. The antigen-adjuvant complex of claim 1, wherein the antigen-reactive moiety is a sulfhydryl-reactive moiety comprising maleimide.

3. The antigen-adjuvant complex of claim 1, wherein the multivalent adjuvant-reactive moiety comprises 3, 4, 5, 6, 7, 8, 9, 10, 11, 12, 13, 14, 15, 16, 17, 18, 19, 20 or more hydroxyl-replacement groups.

4. The antigen-adjuvant complex of claim 3, wherein the hydroxyl-replacement group is selected from the group consisting of a fluoride group, a citrate group, a phosphate group, a carbonate group, and a sulfate group.

5. The antigen-adjuvant complex of claim 4, wherein the hydroxyl-replacement group comprises at least one phosphorylated amino acid residue selected from phosphoserine, phosphotyrosine, and phosphothreonine.

6. The antigen-adjuvant complex of claim 5, wherein the metal hydroxide adjuvant is selected from aluminum hydroxide, aluminum phosphate, calcium hydroxide, calcium phosphate, iron hydroxide, magnesium hydroxide, barium hydroxide, calcium hydroxide, zinc hydroxide, and zirconium hydroxide.

7. An antigen-adjuvant complex comprising an antigen conjugated to alum, wherein the antigen comprises at least one linker comprising 2-12 phosphoserine residues, and wherein the antigen is conjugated via the phosphoserine residues to alum.

8. The antigen-adjuvant complex of claim 7, wherein the antigen is selected from a cancer antigen, a viral antigen, a bacterial antigen, a parasite antigen, and a fungal antigen.

9. The antigen-adjuvant complex of claim 8, wherein the antigen is a viral antigen.

10. The antigen-adjuvant complex of claim 9, wherein the viral antigen is an HIV antigen.

11. The antigen-adjuvant complex of claim 10, wherein the viral antigen is an engineered HIV antigen comprising an engineered HIV envelope protein or fragment thereof.

12. An immunogenic composition comprising the antigen-adjuvant complex according to claim 1, and optionally, an additional adjuvant.

13. An antigen-adjuvant complex comprising an HIV envelope protein or fragment thereof, conjugated to alum via at least one linker comprising 2-12 phosphoserine residues.

14. The antigen-adjuvant complex of claim 13, wherein the HIV envelope protein or fragment thereof is immobilized by site-specific conjugation of the HIV envelope protein or fragment thereof to the adjuvant surface, thus selectively presenting antigen epitopes to immune cells.

15. The antigen-adjuvant complex of claim 7, wherein the at least one linker is covalently linked to the antigen by site-specific conjugation to an antigen-reactive moiety.

16. The antigen-adjuvant complex of claim 15, wherein the antigen-reactive moiety is a sulfhydryl-reactive moiety, optionally a maleimide.

17. The antigen-adjuvant complex of claim 7, wherein the antigen is immobilized by adsorption of the phosphoserine residues to alum, thereby presenting epitopes to immune cells.

18. The antigen-adjuvant complex of claim 11, wherein the engineered HIV antigen comprises eOD or SOSIP.

19. The antigen-adjuvant complex of claim 13, wherein the at least one linker is covalently linked to the HIV envelope protein or fragment thereof through an antigen-reactive moiety.

20. The antigen-adjuvant complex of claim 19, wherein the antigen-reactive moiety is a sulfhydryl-reactive moiety, optionally a maleimide.

21. The antigen-adjuvant complex of claim 13, wherein the HIV envelope protein or fragment thereof comprises eOD or SOSIP.

22. The antigen-adjuvant complex of claim 1, wherein the antigen-reactive moiety is coupled to the multivalent adjuvant-reactive moiety via at least one linker.

23. An antigen-adjuvant complex comprising:
   (a) an antigen modified to be covalently linked to at least one amino acid not naturally occurring in the antigen, wherein the non-naturally occurring amino acid is covalently linked to an antigen-reactive moiety that is coupled to a multivalent adjuvant-reactive moiety comprising two or more hydroxyl-replacement groups; and
   (b) a metal hydroxide adjuvant,
   wherein the antigen is conjugated to the metal hydroxide adjuvant via the hydroxyl replacement groups of the multivalent adjuvant-reactive moiety, thereby forming an antigen-adjuvant complex.

24. The antigen-adjuvant complex of claim 23, wherein the non-naturally occurring amino acid is cystine.

25. The antigen-adjuvant complex of claim 23, wherein the antigen is modified to include the non-naturally occurring amino acid at a predetermined site thereof.

26. The antigen-adjuvant complex of claim 25, wherein the predetermined site is selected to orient the antigen relative to the metal hydroxide adjuvant surface to mask at least one irrelevant epitope present on the antigen.

* * * * *